(12) United States Patent
Acharya et al.

(10) Patent No.: US 9,575,037 B2
(45) Date of Patent: Feb. 21, 2017

(54) DETECTION OF GAS-PHASE ANALYTES USING LIQUID CRYSTALS

(71) Applicant: Platypus Technologies, LLC, Madison, WI (US)

(72) Inventors: Bharat R. Acharya, Madison, WI (US); Kurt A. Kupcho, Madison, WI (US); Bart A. Grinwald, Verona, WI (US); Sheila E. Robinson, Fitchburg, WI (US); Avijit Sen, Madison, WI (US); Nicholas Abbott, Madison, WI (US)

(73) Assignee: PLATYPUS TECHNOLOGIES, LLC, Madison, WI (US)

( * ) Notice: Subject to any disclaimer, the term of this patent is extended or adjusted under 35 U.S.C. 154(b) by 0 days.

(21) Appl. No.: 14/774,964

(22) PCT Filed: Mar. 12, 2014

(86) PCT No.: PCT/US2014/024735
§ 371 (c)(1),
(2) Date: Sep. 11, 2015

(87) PCT Pub. No.: WO2014/165196
PCT Pub. Date: Oct. 9, 2014

(65) Prior Publication Data
US 2016/0018371 A1    Jan. 21, 2016

Related U.S. Application Data

(60) Provisional application No. 61/779,569, filed on Mar. 13, 2013, provisional application No. 61/779,561, filed on Mar. 13, 2013.

(51) Int. Cl.
| | | |
|---|---|---|
| *G01N 33/00* | (2006.01) | |
| *G01N 33/497* | (2006.01) | |
| *B82Y 30/00* | (2011.01) | |

(52) U.S. Cl.
CPC .......... *G01N 33/0004* (2013.01); *B82Y 30/00* (2013.01); *G01N 33/0037* (2013.01); *G01N 33/0044* (2013.01); *G01N 33/497* (2013.01); *Y10T 436/177692* (2015.01); *Y10T 436/184* (2015.01); *Y10T 436/202499* (2015.01); *Y10T 436/25875* (2015.01)

(58) Field of Classification Search
CPC ... B82Y 30/00; G01N 33/0004; G01N 33/497; G01N 33/0037; G01N 33/0044; Y10T 436/17; Y10T 436/173076; Y10T 436/177692; Y10T 436/18; Y10T 436/184; Y10T 436/20; Y10T 436/200833; Y10T 436/202499; Y10T 436/25875
USPC ........ 436/106, 110, 116, 118, 121, 127, 128, 436/130, 164, 165, 167, 181; 422/50, 422/68.1, 82.05, 82.09, 83, 88
See application file for complete search history.

(56) References Cited

U.S. PATENT DOCUMENTS

| | | | |
|---|---|---|---|
| 4,772,376 A | * | 9/1988 | Yukawa ............... G01N 27/417 204/410 |
| 6,284,197 B1 | | 9/2001 | Abbott et al. |
| 6,858,423 B1 | * | 2/2005 | Abbott .................. B82Y 15/00 435/287.2 |
| 7,135,143 B2 | | 11/2006 | Abbott et al. |
| 2010/0093096 A1 | * | 4/2010 | Acharya ............... B82Y 30/00 436/4 |
| 2012/0288951 A1 | | 11/2012 | Acharya et al. |

FOREIGN PATENT DOCUMENTS

| | | |
|---|---|---|
| WO | 99/63329 | 12/1999 |
| WO | 01/61325 | 8/2001 |
| WO | 01/61357 | 8/2001 |

OTHER PUBLICATIONS

Jerome et al. "Anchoring of nematic liquid crystals on mica in the presence of volatile molecules" Physical Review E., 1993, vol. 48, No. 6, pp. 4556-4571.
Shah et al. "Principles for measurement of chemical exposure based on recognition-driven anchoring transitions in liquid crystals" Science, 2001, vol. 293, pp. 1296-1299.
Janzen et al. "Colorimetric sensor arrays for volatile organic compounds" Analytical Chemistry, 2006, vol. 78, No. 11, pp. 3591-3600.

\* cited by examiner

*Primary Examiner* — Maureen Wallenhorst
(74) *Attorney, Agent, or Firm* — Casimir Jones S.C.

(57) ABSTRACT

Provided herein is technology relating to detecting gaseous analytes and particularly, but not exclusively, to devices and methods related to detecting gaseous analytes by monitoring changes in liquid crystals upon exposure to the gaseous analytes.

19 Claims, 65 Drawing Sheets

Octadecane ($C_{18}$)

Eicosane ($C_{20}$)

Docosane ($C_{22}$)

Tetracosane ($C_{24}$)

Before exposure　　　　After exposure

DETECTION OF GAS-PHASE ANALYTES USING LIQUID CRYSTALS

CROSS-REFERENCE TO RELATED APPLICATIONS

This application is a 371 U.S. National Phase Entry of pending International Application No. PCT/US2014/024735, filed Mar. 12, 2014, which claims priority to U.S. Prov. Pat. Appl. Ser. No. 61/779,561, filed Mar. 13, 2013, and U.S. Prov. Pat. Appl. Ser. No. 61/779,569, filed Mar. 13, 2013, the contents of which are incorporated herein by reference in their entireties.

FIELD OF TECHNOLOGY

Provided herein is technology relating to detecting volatile organic compounds and gaseous analytes and particularly, but not exclusively, to devices and methods related to detecting volatile organic compounds and gaseous analytes by measuring changes in the physical properties of liquid crystals upon exposure to the volatile organic compounds and gaseous analytes.

BACKGROUND

The types and concentrations of synthetic chemicals that are in our environment are of greater concern to government, businesses, and society in general than in any time in history. Multiple factors contribute to this heightened concern, such as national security issues related to the use of deadly chemicals as weapons, the risk of an intentional or accidental chemical spill, environmental awareness, and increased understanding of the potential impacts of such chemicals on human health. The range of applications for sensors that can accurately measure volatile gases is wide.

For example, the Department of Homeland Security needs sensors to detect the presence of chemical weapons, such as chemical warfare agents and explosives. These sensors can be integrated into traffic lights in large cities, as components of air-intake valves in municipal buildings, and used as on-board devices for unmanned aerial vehicles or robotic vehicles that are used to explore hazardous situations. Similar sensors can be used to detect natural gas leaks for home and business owners and to monitor outdoor air in local communities, school playgrounds, or agricultural settings.

Approximately 70,000 illnesses and deaths occur annually as a result of occupational exposure to toxic gases, at a cost of more than $100 billion from lost wages and medical expenses. Millions of US workers in various industries are exposed to vapors from various organic chemicals that are recognized by the National Institute of Occupational Safety and Hygiene (NIOSH) as carcinogens, reproductive hazards, and/or neurotoxins. As such, industrial manufacturers need sensors to monitor facility air during production, survey product off-gassing, and assist with maintaining safe levels of permissible exposure limits (PELs) to protect workers against the health effects of exposure to hazardous substances including toxic industrial chemicals. NIOSH and other governmental agencies such as the Environmental Protection Agency, Occupational Safety and Health Agency, Housing and Urban Development, and the Federal Emergency Management Agency are tasked with reducing the risk, and therefore the healthcare burden, of exposure to toxic gases, while attempting to minimize the impact on industry operations and revenues.

For example, volatile organic compounds (VOCs) are a class of widely used organic chemicals that present significant long-term and short-term health risks. These compounds have a high vapor pressure in ambient conditions and thus are readily outgassed from products that contain them. For example, VOCs are present in a wide array of products such as paints and lacquers, paint strippers, cleaning supplies, pesticides, building materials and furnishings, office equipment such as copiers and printers, correction fluids and carbonless copy paper, graphics and craft materials including glues and adhesives, permanent markers, and photographic solutions. Consequently, many people are exposed to VOCs daily.

To protect these people from dangerous exposure to hazardous environments, there is a need for inexpensive devices that measure the concentration of these harmful compounds. Existing devices for measurement of VOCs rely mainly on the photoionization detector-based technology and require high power to operate and are expensive for wide applications. The devices based on colorimetric detection of VOCs, on the other hand, are ambiguous and do not provide quantitative measurement. Therefore, there is an unmet need for a simple technology that enables development of an inexpensive sensor device for quantitative detection of VOCs for a number of applications including HazMat/Homeland Security, industrial hygiene, indoor air quality, military applications, and biomedical applications.

In addition to applications related to monitoring exposure to dangerous gas-phase chemicals and protecting the health of individuals, detection of gas-phase analytes finds uses in industrial and commercial settings. For example, some industrial applications include monitoring product performance such as interrogating vehicle emissions for release of volatile gases. Additional applications include assessing fruit ripeness and/or spoilage based on volatile gas emissions.

There is also broad potential for use of sensors of gas-phase analytes in biomedical applications. For example, sensors have been used to monitor the composition of gas mixtures used for anesthesia during surgical procedures or to monitor exhaled gases related to metabolic activities. Recently, analysis of human breath has emerged as a non-invasive technique for diagnosis of disease. The exhaled human breath contains a number of volatile gases such as oxygen, carbon dioxide, nitrogen, carbon monoxide, acetone, ammonia, hydrogen sulfide, amines, oxides of nitrogen, etc. (Manolis, 1983; Smith et al, 1999; and Diskin et al, 2003) and measurements of analytes in exhaled breath have been applied to a wide range of disease states, including diabetes (Henderson et al, 1952; Sulway et al, 1970; Crofford et al, 1977; and Novak et al, 2007), gastrointestinal disorders (Perman, 1991; Bauer et al, 2000; and Nieminen et al, 2000), and asthma (Alving et al, 1993).

While current technologies exist to measure gaseous analytes (e.g., volatile organic compounds and other compounds), these technologies do not provide timely information regarding gas levels to inform immediate actions for minimizing risks, e.g., taking appropriate measures in the medical, defense, and industrial settings to protect human health. For example, many direct-read dosimeters lack sensitivity and reproducibility and do not meet regulatory monitoring requirements. Alternatively, many indirect read technologies are shipped to an accredited laboratory for analysis, introducing a long lag-time of typically many weeks between sample collection and data retrieval. In addition, conventional technologies are also subject to substantial positive or negative interference from other pollutants and inaccuracies resulting from low air flow. There exists, therefore, an unmet need for technology that accurately measures gases and that can be read on-site to provide actionable information.

In some situations described above, it is necessary to know the concentration of the chemical environment as quickly as possible in order to minimize exposure to the chemical. In such situations a detector of the instantaneous concentration of the gas is needed. In other situations, such as but not limit to when measuring personal exposure to a vapor, it is necessary to know the cumulative exposure to the chemical that occurs of a given interval of time, such as but not limited to a workday. In this situation, a dosimeter that measures the cumulative level of exposure over a set period of time is needed.

SUMMARY

Provided herein is technology related to sensors and analyte detection associated with the use of liquid crystal (LC) materials. In some embodiments, the technology relates to detecting volatile organic compounds and particularly, but not exclusively, to methods and compositions for detecting volatile organic compounds by measuring changes in the physical properties of liquid crystals. In some embodiments, the LC materials that find use in the technology comprise rod-shaped organic molecules that form condensed phases. These materials possess long-range orientational ordering (and are thus in some aspects crystal-like) but lack positional ordering (and are thus in some aspects liquid-like). The long-range ordering of molecules within the LC gives rise to anisotropic optical properties and optical birefringence. The interaction of gas-phase analytes with particular LC materials and or with the surface supporting it modifies the long-range order or orientation of the LCs and produces distinct changes in the optical appearance of the LC, thus providing a measurable indicator associated with the analyte.

Accordingly, some embodiments of the technology provide methods for detecting an analyte (e.g., a VOC) in a gaseous phase, the method comprising providing a liquid crystal assay device; exposing the liquid crystal assay device to a sample suspected of comprising an analyte; and interrogating the liquid crystal assay device to detect the analyte, wherein a change in a property of the liquid crystal composition in the liquid crystal assay device caused by an interaction of the analyte with the liquid crystal assay device is indicative of the presence of the analyte. In some embodiments the liquid crystal assay device comprises a first surface contacting a composition comprising a liquid crystal; a second surface; and a headspace between the composition comprising the liquid crystal and the second surface. In some embodiments, the first surface comprises a functional group and an interaction of the analyte with the functional group causes the change in the property of the liquid crystal composition. For example, some embodiments provide that the functional group is specific for the analyte. In some embodiments, detection of the analyte is cumulative. In some embodiments, the change in a property of the liquid crystal composition is detectable in real-time. In some embodiments, the presence of said analyte is detected in real-time. The headspace is related to the rate of exposure of the device to the analyte and, as such, provides a functionality to control the rate of exposure of the device to the analyte. In some embodiments, the headspace is 1 to 100 microns, 5 to 50 microns, or, in some embodiments, 10 to 25 microns. In some embodiments, the headspace is variable. In some embodiments, the first and second surfaces form a compartment having first and second open ends, wherein the headspace at the first end is from 1 to 20 microns and the headspace at the second end is from 21 to 100 microns.

The thickness of the liquid crystal film is related to the response of the device to the analyte, e.g., by controlling the rate at which the analyte reaches a functionalized surface upon which the liquid crystal has been deposited. Embodiments are provided in which micro-pillar features on a surface control the thickness of the liquid crystal film. Accordingly, in some embodiments the first surface further comprises micro-pillars. The surfaces are not limited in the materials from which they are made. For instance, some embodiments provide that the first surface and/or the second surface comprises a substrate of glass, silicon, or gold. In some embodiments, the second surface is functionalized with an intert substance. In some embodiments, the second surface is functionalized with (Tridecafluoro-1,1,2,2-tetrahydrooctyl)-trichlorosilane.

Some embodiments provide a device in which the analyte interacts directly with the liquid crystal to effect a phase in the liquid crystal. Some embodiments provide a device in which the liquid crystal contacts a surface (e.g., a functionalized surface) and the interaction of the analyte with the functionalized surface effects an orientation of the liquid crystal. In some embodiments, the functionalized surface comprises a functional group that is 4-aminothiophenol. In some embodiments, the functionalized surface comprises a functional group that is lead perchlorate.

The technology is not limited in the liquid crystal that is used to indicate the presence of the analyte. For example, some exemplary liquid crystals that find use in the technology are MBBA, MLC-2080, MLC-2081, and E7, and mixtures thereof. Various liquid crystal compositions find use in embodiments of the technology. For instance, in some embodiments the liquid crystal composition comprises a cyanobiphenyl compound.

Particular exemplary embodiments of the technology detect the analytes $H_2S$, HCHO, $NO_2$, toluene, benzene, xylene, nitrobenzene, hexane, alcohol, gasoline, and components of gasoline (e.g., octane, etc.).

A phase change in a liquid crystal can be associated with a change in the optical anisotropy, magnetic anisotropy, dielectric anisotropy, and/or the presence of a phase transition temperature. Accordingly, some embodiments provide methods wherein the interrogation comprises measuring a change in a property selected from the group consisting of optical appearance, optical anisotropy, magnetic anisotropy, dielectric anisotropy, rheology, optical absorbance, and phase transition temperature. In some embodiments, exposing the liquid crystal assay device to a sample suspected of comprising an analyte causes a phase transition in the liquid crystal composition from a first phase selected from the group consisting of an isotropic phase, a nematic phase, or a smectic phase to a second phase selected from the group consisting of an isotropic phase, a nematic phase, and a smectic phase. In some embodiments, the liquid crystal composition undergoes an orientational transition in the presence of the analyte, such as a change in the orientation of the optical axis of the liquid crystal (e.g., a change in the tilt of the liquid crystal from the surface normal). In some exemplary embodiments, the orientational transition is selected from the group consisting of a homeotropic alignment changing to a planar alignment, a random planar alignment changing to a uniform planar alignment, a uniform planar alignment changing to a random planar alignment, and a planar alignment changing to a homeotropic alignment.

Embodiments are provided in which a headspace provides a channel for access of the analyte to the device and liquid crystal. As such, some embodiments provide that the second surface does not contact the composition comprising the liquid crystal.

In some embodiments, the concentration or accumulated exposure to an analyte is related to the size of an area of the device in which the liquid crystal has undergone a phase change (a "reacted area" of the device). Consequently, embodiments are provided in which method comprise quantifying an analyte concentration by measuring a size of a LC responded area. For instance, in some embodiments the methods comprise quantifying an analyte concentration by measuring a distance of a birefringent front from a site of exposure of the liquid crystal assay device to the sample suspected of comprising the analyte. In some embodiments, measuring an anisotropy provides an observable property to differentiate the phases (e.g., the "unreacted area" and the "reacted area") and thus assess the size (e.g., the length) of the reacted area. In some embodiments, the anisotropy is an optical anisotropy and the interrogation comprises measuring a reflection or a transmission of polarized light. In some embodiments, measurement of the rate of increase in the reacted area is used to indicate the concentration of the analyte present around the device.

In some embodiments, methods are provided detecting an analyte in a gaseous phase, the methods comprising providing a liquid crystal assay device comprising a surface in a channel; exposing the liquid crystal assay device to a sample suspected of comprising an analyte; contacting the surface with a liquid crystal; and interrogating the liquid crystal assay device to detect the analyte, wherein a change in a property of the liquid crystal composition in the liquid crystal assay device caused by an interaction of the analyte with the liquid crystal assay device is indicative of the presence of the analyte. In these embodiments, the surface is reacted with the analyte and the liquid crystal is applied to "read" the reacted portion of the surface. For instance, in some embodiments the surface comprises a functional group and an interaction of the analyte with the functional group causes the change in the property of the liquid crystal composition. Particular embodiments provide that the functional group is specific for the analyte.

The surfaces are not limited in the materials from which they are made. For instance, some embodiments provide that the first surface and/or the second surface comprises a substrate of glass, silicon, or gold.

Some embodiments provide a device in which the liquid crystal contacts a surface (e.g., a functionalized surface) and the interaction of the analyte with the functionalized surface effects a phase change in the liquid crystal. In some embodiments, the functionalized surface comprises a functional group that is 4-aminothiophenol. In some embodiments, the functionalized surface comprises a functional group that is lead perchlorate.

A phase change in a liquid crystal causes a change in a composition comprising the liquid crystal such as a change in the optical anisotropy, magnetic anisotropy, dielectric anisotropy, and/or phase transition temperature. Accordingly, some embodiments provide methods wherein the interrogation comprises measuring a change in a property selected from the group consisting of optical anisotropy, magnetic anisotropy, dielectric anisotropy, and phase transition temperature. In some embodiments, exposing the liquid crystal assay device to a sample suspected of comprising an analyte causes a phase transition in the liquid crystal composition from a first phase selected from the group consisting of an isotropic phase, a nematic phase, a liquid crystal phase rich in chiral dopants, a frustrated phase, a blue phase, a ferroelectric phase, a twisted grain boundary phase, or a smectic phase to a second phase selected from the group consisting of an isotropic phase, a nematic phase, and a smectic phase, a liquid crystal phase rich in chiral dopants, a frustrated phase, a blue phase, a ferroelectric phase, a twisted grain boundary phase. In some embodiments, the liquid crystal composition undergoes an orientational transition in the presence of the analyte, wherein the orientational is a change in the orientation of the optical axis of the liquid crystal. In some exemplary embodiments, the orientational change is selected from the group consisting of a homeotropic alignment changing to a planar alignment, a random planar alignment changing to a uniform planar alignment, a uniform planar alignment changing to a random planar alignment, and a planar alignment changing to a homeotropic alignment. In other embodiments, the orientational transition involves a change in the tilt of the liquid crystal away from the surface normal.

In some embodiments, the concentration or accumulated exposure to an analyte is related to the size of an area of the device in which the liquid crystal has undergone a phase or orientational change (a "reacted area" of the device). Consequently, embodiments are provided in which method comprise quantifying an analyte concentration by measuring a size of a reacted area. For instance, in some embodiments the methods comprise quantifying an analyte concentration by measuring a distance of a birefringent front from a site of exposure of the liquid crystal assay device to the sample suspected of comprising the analyte. In some embodiments, measuring an anisotropy provides an observable property to differentiate the phases (e.g., the "unreacted area" and the "reacted area") and thus assess the size (e.g., the length) of the reacted area. In some embodiments, the anisotropy is an optical anisotropy and the interrogation comprises measuring a reflection or a transmission of polarized light.

In some embodiments, the size of the reacted area is on the order of 1, 10, 100, or 1000 mm$^2$. For example, in some embodiments the distance measured for a reacted area is from about 1 micron about 200 mm, for example, from about 1 micron to 1 mm, 1 micron to 10 mm, 1 micron to 50 mm, 1 micron to 100 mm, 1 micron to 200 mm, 1 mm to 10 mm, 1 mm to 50 mm, 1 mm to 100 mm, 1 mm to 200 mm, 10 mm to 100 mm or 10 mm to 200 mm.

The technology finds use in monitoring exposure (e.g., of a person) to a gaseous analyte such as a toxic gas. Accordingly, embodiments of methods are provided for monitoring a subject's exposure to a toxic gas, the methods comprising providing to the subject a dosimeter badge comprising a liquid crystal assay device; measuring a change in a property of a liquid crystal composition in the liquid crystal assay device caused by an interaction of the toxic gas with the liquid crystal composition; and reporting an exposure to the toxic gas. Monitoring methods comprise use of embodiments of devices provided herein. In some embodiments the devices report exposure in real-time to provide an immediate signal of exposure. In some embodiments, the devices report a cumulative exposure over an amount of time (e.g., 1 to 100 minutes; 1 to 10 days; 1 to 10 weeks; or more). In some embodiments, detection of the analyte is in real-time. Embodiments comprise methods relate to a liquid crystal assay device that comprises a first surface contacting a composition comprising a liquid crystal; a second surface;

and a headspace between the composition comprising the liquid crystal and the second surface. Further embodiments are provided wherein the liquid crystal assay device comprises a surface in a channel and the method further comprises contacting the surface with a liquid crystal.

In some embodiments, the devices are distinguishable from other dosimeter devices, such as electrochemical devices, based on the mass of the device. In some preferred embodiments, the devices of the present invention have a mass of from about 5 to 50 grams, preferably from about 10 to 30 grams or from 10 to 20 grams.

In some embodiments, the present invention provides a sensor device comprising a first substrate having a surface modified with an amine moiety, said surface having disposed thereon a liquid crystal composition that is homeotropically aligned in the presence of the amine moiety. In some embodiments, the substrate comprises a gold film disposed on an underlying base substrate. In some embodiments, the substrate further comprises an intervening layer between the base substrate and said gold film. In some embodiments, the intervening layer is a metallic adhesion layer selected from the group consisting of titanium and chromium. In some embodiments, the amine moiety is 4-aminothiophenol. In some embodiments, the substrate is a glass substrate. In some embodiments, the amine moiety is p-aminophenyltrimethoxysilane. In some embodiments, the liquid crystal composition comprises MBBA. In some embodiments, the sensor devices further comprise a second substrate oriented opposite of the first substrate to define a compartment. In some embodiments, the compartment has a headspace between the liquid crystal composition disposed on said first substrate and said second substrate. In some embodiments, the headspace is 1 to 100 microns. In some embodiments, the headspace is 5 to 50 microns. In some embodiments, the headspace is 10 to 25 microns. In some embodiments, the headspace is variable. In some embodiments, the first and second surfaces form a compartment having first and second open ends, wherein the headspace at the first end is from 1 to 20 microns and the headspace at the second end is from 21 to 100 microns.

In some embodiments, the technology provides a method for detecting a volatile organic compound in a gaseous phase, the method comprising providing a liquid crystal assay device comprising a surface in contact with a liquid crystal composition; exposing the liquid crystal assay device to a sample suspected of comprising a volatile organic compound; and interrogating the liquid crystal assay device to detect the volatile organic compound, wherein a change in a property of the liquid crystal composition in the liquid crystal assay device caused by an interaction of the volatile organic compound with the liquid crystal assay device is indicative of the presence of the volatile organic compound. In some embodiments, the surface comprises a substrate of glass, gold, or silicon and in some embodiments the surface comprises micro-pillars.

Various liquid crystal compositions find use in embodiments of the technology. For instance, in some embodiments the liquid crystal composition comprises a cyanobiphenyl compound. Furthermore, the technology is directed toward detecting various volatile organic compounds, e.g., in some embodiments the volatile organic compound is toluene, benzene, xylene, nitrobenzene, hexane, or an alcohol. In other embodiments, the volatile organic compound is octane, gasoline, painer thinner or stove alcohol.

In some embodiments, the surface is a polymer deposited on a substrate. The technology is not limited in the polymer that is deposited. For example, in some embodiments the polymer is a polystyrene, a polyvinyl acetate, or a fluoroalcohol polycarbosilane. Furthermore, in some embodiments the polymer is mechanically rubbed.

In some embodiments the surface is a hydrocarbon film deposited on a substrate. For example, some embodiments provide that the hydrocarbon film comprises a long chain aliphatic hydrocarbon, for instance in some embodiments a hydrocarbon film that is solid at room temperature and is soluble in the volatile organic compound or is plasticized by the volatile organic compound. In some embodiments the hydrocarbon comprises an aliphatic chain of 18 or more carbons.

The methods detect volatile organic compounds over a range of concentrations. Exemplary embodiments are provided wherein the method detects a volatile organic compound of at least approximately 50 ppm.

In some embodiments, the liquid crystal composition is utilized in the form of polymer dispersed liquid crystal and in some particular embodiments the polymer dispersed liquid crystal is formed in the liquid crystal assay device in a strained configuration.

In some embodiments, the surface comprises a cavity and the liquid crystal composition is confined in the cavity.

In some embodiments the liquid crystal composition is confined in a polymer matrix. In some embodiments, the liquid crystal composition is a polymer dispersed liquid crystal deposited on a rubbed polymer film. In some embodiments, the polymer dispersed liquid crystal comprises droplets having a diameter of less than 2 microns.

In some embodiments, the surface comprises an ionic salt. For example, in some embodiments the surface comprises a first ionic salt that is soluble in the volatile organic compound and a second ionic salt that is not soluble in the volatile organic compound. Exemplary ionic salts include a quaternary ammonium, a tetraphenylborate, or a metal perchlorate salt.

In some embodiments, the liquid crystal comprises a polymer bead.

Volatile organic compounds induce changes in a variety of physical characteristics of the liquid crystal compositions. For example, in some embodiments exposing the liquid crystal assay device to a sample suspected of comprising a volatile organic compound causes a phase transition in the liquid crystal composition. In some embodiments exposing the liquid crystal assay device to a sample suspected of comprising a volatile organic compound causes a structural change of the liquid crystal composition confined in a microstructure. In some embodiments exposing the liquid crystal assay device to a sample suspected of comprising a volatile organic compound causes a dewetting of a polymer film on the substrate. In some embodiments exposing the liquid crystal assay device to a sample suspected of comprising a volatile organic compound causes a structural change in a polymer film supporting the liquid crystal composition. In some embodiments exposing the liquid crystal assay device to a sample suspected of comprising a volatile organic compound causes dissolution of an ionic salt into the liquid crystal composition. In some embodiments exposing the liquid crystal assay device to a sample suspected of comprising a volatile organic compound causes swelling of a polymer bead suspended in the liquid crystal composition.

Changes in physical characteristics of the liquid crystal composition are monitored or interrogated by various methods. In some embodiments the interrogation comprises measuring a change in a property such as optical anisotropy, magnetic anisotropy, rheology, optical absorbance, dielectric anisotropy, or phase transition temperature. In some embodiments the change in the property of the liquid crystal composition in the liquid crystal assay device caused by interaction of the volatile organic compound with the liquid crystal assay device is a change in transmission of polarized light.

In some embodiments the liquid crystal assay device comprises an array of discrete assay areas and an internal calibration area and wherein the interrogation comprises comparing the response of an assay area to the internal calibration area.

In some embodiments the surface has a form selected from the group consisting of planar, spherical, and cylindrical. In some embodiments the surface is a patterned surface, for example, a patterned surface that comprises a feature such as a grid, a channel, a pillar, or an assay area, or a combination thereof. In some embodiments, the features are 1 to 50 microns high, 1 to 200 microns wide, and spaced 1 to 200 micron apart. Moreover, in some embodiments the pillars have a form that is circular, triangular, square, or hexagonal.

In some embodiments, exposing the liquid crystal assay device to a sample suspected of comprising a volatile organic compound causes a phase transition in the liquid crystal composition from a first phase that is an isotropic phase, a nematic phase, or a smectic phase to a second phase that is an isotropic phase, a nematic phase, and a smectic phase. In some embodiments the liquid crystal composition undergoes an orientational transition in the presence of the volatile organic compound, wherein the orientational transition is a homeotropic alignment changing to a planar alignment, a random planar alignment changing to a uniform planar alignment, a uniform planar alignment changing to a random planar alignment, or a planar alignment changing to a homeotropic alignment. In some embodiments, the liquid crystal undergoes an orientational transition that changes the tilt of the liquid crystal from the normal. In some embodiments the liquid crystal composition comprises a dopant.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 8 is a series of images acquired of cumulative analyte sensors.

FIG. 16a shows a depiction of formaldehyde vapor diffusing into the headspace and into the LC film, thus generating a lateral concentration gradient that is seen as a dark front on each side of the badge (FIG. 16b). FIG. 16c is a plot showing the measured light intensity decreasing linearly with exposure time.

FIG. 26B shows a linear relationship between the length of the bright channel and the NO₂ concentration.

FIG. 27A, FIG. 27B, and FIG. 27C shows the alignment of the liquid crystals MBBA, MLC-2080, and MLC-2081, respectively.

FIG. 53A shows PDLC droplets before incubation at 50° C. for 2 minutes. FIG. 53B shows PDLC droplets after incubation at 50° C. for 2 minutes and FIG. 53C shows PDLC droplets after exposure to 8600 ppm toluene. The images were taken with a polarizing microscope with 50× magnification objective.

Figure 1A:
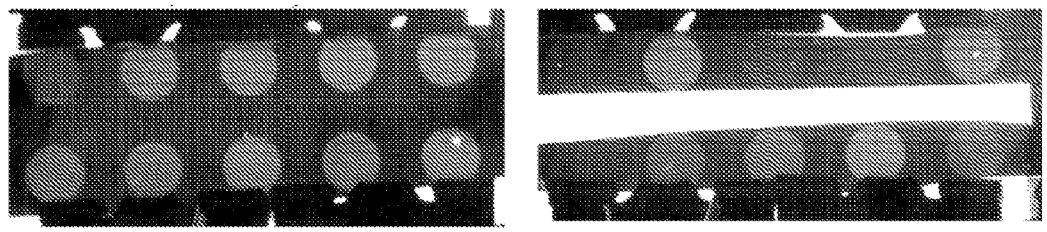
FIG. 1 shows images of 2×5 sensors before exposure to $H_2S$ (FIG. 1A), long sensors #1 to #4 before exposure to $H_2S$ (FIG. 1B), and sandwich cells comprising mylar of 25 microns and 50 microns before exposure to $H_2S$ (FIG. 1C). The bright stripe at the middle of the FIG. 1A right side is duel to the mylar strip.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to detecting gaseous analytes and particularly, but not exclusively, to devices and methods related to detecting gaseous analytes by monitoring changes in liquid crystals upon exposure to the gaseous analytes.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "wavefront" refers to a line of demarcation that is observable between a region of ordered liquid crystal and a region of disordered liquid crystal. In many cases, the wavefront is visually detectable. However, the location of the wavefront can also be detected by image analysis procedures.

As used herein, the term "ligand" refers to any molecules that bind to or can be bound by another molecule.

As used herein, the term "detection region" refers to a discreet area that is designated for detection of an analyte in a sample.

As used herein, the terms "material" and "materials" refer to, in their broadest sense, any composition of matter.

As used herein, the term "field testing" refers to testing that occurs outside of a laboratory environment. Such testing can occur indoors or outdoors at, for example, a worksite, a place of business, public or private land, or in a vehicle.

As used herein, the term "nanostructure" refers to a microscopic structure, typically measured on a nanometer scale. Such structures include various three-dimensional assemblies including, but not limited to, liposomes; films; multilayers; braided, lamellar, helical, tubular, and fiber-like shapes; and combinations thereof. Such structures can, in some embodiments, exist as solvated polymers in aggregate forms such as rods and coils. Such structures can also be formed from inorganic materials, such as prepared by the physical deposition of a gold film onto the surface of a solid, proteins immobilized on surfaces that have been mechanically rubbed, and polymeric materials that have been molded or imprinted with topography by using a silicon template prepared by electron beam lithography.

As used herein, the term "self-assembling monomers" refers to molecules that spontaneously associate to form molecular assemblies. In one sense, this can refer to surfactant molecules that associate to form surfactant molecular assemblies. The term "self-assembling monomers" includes single molecules and small molecular assemblies, whereby the individual small molecular assemblies can be further aggregated (e.g., assembled and polymerized) into larger molecular assemblies.

As used herein, the term "linker" or "spacer molecule" refers to material that links one entity to another. In one sense, a molecule or molecular group can be a linker that is covalent attached to two or more other molecules (e.g., linking a ligand to a self-assembling monomer).

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., C—C). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds. As used herein the terms "amine bond," "thiol bond," and "aldehyde bond" refer to any bond formed between an amine group (e.g., a chemical group derived from ammonia by replacement of one or more of its hydrogen atoms by hydrocarbon groups), a thiol group (e.g., sulfur analogs of alcohols), and an aldehyde group (e.g., the chemical group —CHO joined directly onto another carbon atom), respectively, and another atom or molecule.

As used herein, the term "covalent bond" refers to the linkage of two atoms by the sharing of two electrons, one contributed by each of the atoms.

As used herein, the terms "optical anisotropy" and "birefringence" refer to the optical property of having a refractive index that depends on the polarization and propagation direction of light. Optically anisotropic materials are said to be birefringent. The anisotropy in optical properties of liquid crystals gives rise to optical birefringence, that is, different refractive indices when measured with different polarization directions.

As used herein, the term "magnetic anisotropy" refers to having different magnetic properties for different directions of magnetic fields. Magnetic anisotropy produces different magnetic susceptibilities in a material when measured with different magnetic field directions.

As used herein, the term "dielectric anisotropy" refers to having different dielectric properties for different directions of electric fields. Dielectric anisotropy produces different dielectric constants in a material when measured with different electric field directions.

As used herein, the term "spectrum" refers to the distribution of electromagnetic (e.g., light) energies arranged in order of wavelength.

As used the term "visible spectrum" refers to light radiation that contains wavelengths from approximately 360 nm to approximately 800 nm.

As used herein, the term "substrate" refers to a solid object or surface upon which another material is layered or attached. Solid supports include, but are not limited to, glass, metals, gels, and filter paper, among others.

As used herein, the terms "array" and "patterned array" refer to an arrangement of elements (e.g., entities) onto or into a material or device. For example, depositing several types of liquid crystals into discrete regions on an analyte-detecting device would constitute an array.

As used herein, the term "in situ" refers to processes, events, objects, or information that are present or take place within the context of their natural environment.

As used herein, the term "sample" is used in its broadest sense. In one sense it can refer to a biopolymeric material. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals, and industrial samples. These examples are not to be construed as limiting the sample types applicable to the present technology.

As used herein, the term "liquid crystal" refers to a thermodynamic stable phase characterized by anisotropy of properties without the existence of a three-dimensional crystal lattice, generally lying in the temperature range between the solid and isotropic liquid phase.

As used herein, the term "mesogen" refers to compounds that form liquid crystals, including rod-like or disc-like molecules that are components of liquid crystalline materials.

As used herein, "thermotropic liquid crystal" refers to liquid crystals that result from the melting of mesogenic solids due to an increase in temperature. Both pure substances and mixtures form thermotropic liquid crystals.

"Lyotropic," as used herein, refers to molecules that form phases with orientational and/or positional order in a solvent. Lyotropic liquid crystals can be formed using amphiphilic molecules (e.g., sodium laurate, phosphatidylethanolamine, lecithin). The solvent can be water.

"Metallotropic," as used herein, refers to metal complexes of organic ligands that exhibit liquid crystalline character. Thermotropic metallomesogens have been made that incorporate many metals. They can be rodlike (calamitic) and disklike (discotic). The ligand can be monodentate (e.g., 4-substituted pyridines), bidentate (e.g., beta-diketonates, dithiolenes, carboxylates, cyclometalated aromatic amines), or polydentate (e.g., phthalocyanines, porphyrins). The ligands influence the mesophase character based on molecular shape and intermolecular forces. The metallomesogens provide a rigid core, which is typically unsaturated and either rod- or disklike in shape, and several long hydrocarbon tails where the metal atom is usually at or near the center of gravity of the molecule. Metallotropic liquid crystals, acting through the metal moiety, can be tuned to capture different target analytes by different methods including but not limited to displacement, redox reactions, and ligand formation.

As used herein, the term "heterogenous surface" refers to a surface that orients liquid crystals in at least two separate planes or directions, such as across a gradient.

As used herein, "nematic" refers to liquid crystals in which the long axes of the molecules remain substantially parallel, but the positions of the centers of mass are randomly distributed. Nematic liquid crystals can be substantially oriented by a nearby surface.

"Chiral nematic," as used herein refers to liquid crystals in which the mesogens are optically active. Instead of the director being held locally constant as is the case for nematics, the director rotates in a helical fashion throughout the sample. Chiral nematic crystals show a strong optical activity that is much greater than can be explained solely on the bases of the rotatory power of the individual mesogens. When light equal in wavelength to the pitch of the director impinges on the liquid crystal, the director acts like a diffraction grating, reflecting most and sometimes all light incident on it. If white light is incident on such a material, only one color of light is reflected and it is circularly polarized. This phenomenon is known as selective reflection and is responsible for the iridescent colors produced by chiral nematic crystals.

"Smectic," as used herein, refers to liquid crystals that are distinguished from "nematics" by the presence of a greater degree of positional order in addition to orientational order. In a smectic phase the molecules spend more time in planes and layers than they do between these planes and layers. "Polar smectic" layers occur when the mesogens have permanent dipole moments. In the smectic A2 phase, for example, successive layers show anti ferroelectric order, with the direction of the permanent dipole alternating from layer to layer. If the molecule contains a permanent dipole moment transverse to the long molecular axis, then the chiral smectic phase is ferroelectric. A device utilizing this phase can be intrinsically bistable.

"Frustrated phases," as used herein, refers to another class of phases formed by chiral molecules. These phases are not chiral; however, twist is introduced into the phase by an array of grain boundaries. A cubic lattice of defects (where the director is not defined) exists in a complicated, orientationally ordered twisted structure. The distance between these defects is hundreds of nanometers, so these phases reflect light just as crystals reflect X-rays.

"Discotic phases" are formed from molecules that are disc shaped rather than elongated. Usually these molecules have aromatic cores and six lateral substituents. If the molecules are chiral or a chiral dopant is added to a discotic liquid crystal, a chiral nematic discotic phase can form.

Embodiments of the Technology

The present technology relates to detecting gaseous compounds using a liquid crystal assay format and a device utilizing liquid crystals as part of a reporting system. Liquid crystal-based assay systems and devices (LC assays) are described, e.g., in U.S. Pat. No. 6,284,197; Int'l App. Pub. Nos. WO 2001/061357; WO 2001/061325; WO 1999/063329; Gupta et al. (1998) *Science* 279:2077-2080; Kim et al. (2000) "Orientations of Liquid Crystals on Mechanically Rubbed Films of Bovine Serum Albumin: A Possible Substrate for Biomolecular Assays Based on Liquid Crystals" *Analytical Chemistry* 72: 4646-4653; Skaife et al. (2000) "Quantitative Interpretation of the Optical Textures of Liquid Crystals Caused by Specific Binding of Immunoglobulins to Surface-Bound Antigens" *Langmuir* 16: 3529-3536; Gupta et al. (1999) "Using Droplets of Nematic Liquid Crystal To Probe the Microscopic and Mesoscopic Structure of Organic Surfaces" *Langmuir* 15: 7213-7223; and Shah et al. (2001) "Principals for Measurement of Chemical Exposure Based on Recognition-Driven Anchoring Transitions in Liquid Crystals" *Science* 293: 1296-99, all of which are incorporated herein by reference.

U.S. Pat. No. 6,284,197 and Shah et al, supra, describe the detection of chemical molecules with a liquid crystal assay format that relies on an orientational change in the LC following the interaction of the chemical molecules with a functionalized surface on which the LC has been overlaid. Moreover, liquid crystal assays are also used for detecting gaseous compounds that interact directly or indirectly with the LC itself to produce a phase transition of the LC material. The use of different LCs that provide different functional moieties and/or reactive groups, or the use of LC compositions comprising a dopant, in the assays provide materials that identify gaseous compounds through the interaction of the gaseous compound with the functional moieties on the LC and/or the dopant. Furthermore, the liquid crystal assay devices of the present technology find use to quantify gaseous compounds.

In some embodiments, the detection of analytes or their derivatives in gas phase is accomplished through a direct interaction of the analyte with the LC. Depending upon the target analyte, some embodiments provide LCs that are synthesized to have a functional group that specifically interacts or reacts with the analyte. The liquid crystal can either be supported on a surface or in a small bulk amount through which the analyte is passed. The present technology is not limited to the detection of any particular analyte in gas phase. Indeed, the detection of a variety of analytes is contemplated. Exemplary analytes are nitric oxide, formaldehyde, and hydrogen sulfide. A number of LCs with different functional moieties is commercially available. Some of these LCs have suitable reactive moieties that are selective for some target analytes. For example, MBBA (N-(4-methoxybenzylidene)-4-butylaniline and EBBA (N-(4-ethoxybenzylidene)-4-butylaniline) have functional groups similar to the aniline group that can be used for detecting nitrate-based gases. A number of azomethine-type LCs (see, e.g., Hioki et al. (2004) *Tetrahedron Letters* 45: 7591-7594), polyaniline-based polymers (*J. Phys. Chem. B* 108: 8894-8899), and polyaniline-based moieties and polyimides (*Journal of Polymer Science: Part A: Polymer Chemistry* 40: 1583-1593) have been synthesized. The interaction between the analyte and the LC can be physical in nature or based on a chemical reaction. The interaction of the target analyte with the LC can manifest as a change in a physical property of the LC (e.g., a change in the phase transition temperature, optical birefringence, dielectric anisotropy, magnetic anisotropy, or a change in the orientation of the LC on a surface) that can be detected using a variety of instruments capable of detecting these physical changes.

In some embodiments, the LC molecules are oriented on a chemically functionalized surface having a surface chemistry that is known to interact with the target analytes. When the sensor surface is exposed to a test environment, the analyte diffuses through the LC film and interacts with the surface chemistry. As a result, the orientation of the LC on the modified surface changes, thus leading to a change in the optical properties of the LC film.

In some embodiments, the LC sensor comprises an LC film that is supported by a single chemically functionalized surface and the whole LC film is exposed to the test environment. Upon exposure, the analyte molecules diffuse through the LC film and bind to the surface chemistry and the LC molecules change orientation. As a result, the optical properties and appearance of the LC film change in real time. Depending on the surface chemistry/analyte combination, the response can be reversible or irreversible. This embodiment allows for the sensitive detection of analytes. In some embodiments, the dynamic response of the sensor is monitored by measuring the response time (e.g., the time it takes for the sensor to respond). The response time is a function of the concentration of the analyte and is used as a parameter to assess the quantitative response of the sensor.

Some embodiments utilize a thin film of LC supported between two chemically functionalized surfaces with openings from one or more sides of the sensor. When the monitor is exposed to the test environment, the analyte now will have to diffuse from the side of the sensor (as opposed to from the top of the LC film). Therefore, only the cross-section of the LC film is exposed to the test environment. As the analyte diffuses across the film, it interacts with the surface chemistry, thereby inducing a change in the orientation of the LC. This change appears as a bright front on the sides of the sensor open to the test environment that propagates inward into the LC film as the exposure time increases. Because of the macroscopic diffusion dimension involved, the response is irreversible and it provides a cumulative measure of the analyte. A measurable response is obtained after macroscopic lateral diffusion of the analytes through the LC film.

In some embodiments, the technology is related to detecting VOCs using materials and structures in conjunction with liquid crystals (LCs) that find use in simple, inexpensive sensors for unambiguous detection of VOCs. In particular, changes in physical properties of a LC material in contact with these materials and structures, upon exposure to VOCs, are detected visually, by simple light intensity measurement, or by measuring other measurable physical parameters (such as dielectric anisotropy, light scattering, etc.) associated with the state of LC material.

I. Liquid Crystals

The technology is related to sensors comprising a liquid crystal (LC). The technology is not limited in the liquid crystal used and, further, the technology provides various embodiments in which any known or yet discovered LC is used according to the technology as it is described herein. Any compound or mixture of compounds that forms a mesogenic layer can be used in conjunction with the present technology. The mesogens can form thermotropic or lyotropic liquid crystals. The mesogenic layer can be either continuous or it can be patterned. In some embodiments, the LC comprises a compound comprising a Schiff base. In some embodiments, the compound is a diazo compound, an azoxy compound, a nitrone, a stilbene, a tolan, an ester, or a biphenyl. For example, in some embodiments, the LC comprises a compound according to the structure:

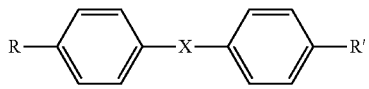

wherein R and R' are independently selected from alkyl, lower alkyl, substituted alkyl, aryl groups, acyl, halogens, hydroxy, cyano, amino, alkoxy, alkylamino, acylamino, thioamido, acyloxy, aryloxy, aryloxyalkyl, mercapto, thia, aza, oxo, saturated cyclic hydrocarbon, unsaturated cyclic hydrocarbons, heterocycle, arylalkyl, substituted aryl, alkylhalo, acylamino, mercapto, substituted arylalkyl, heteroaryl, heteroarylalkyl, substituted heteroaryl, substituted heteroarylalkyl, substituted heterocyclic, and heterocyclicalkyl. In some embodiments, X is selected from C1 to C10, —C≡N—, —N═N—, —N═N(O)—, —C═N(O)═N(O)—, —CH═NO—, —HC═CH—, —C≡C—, and —OC(O)—.

In some embodiments the LC is a nematic LC (e.g., E7) and in some embodiments the LC is a smectic liquid crystal (e.g., 8CB). In some embodiments, the LC is a thermotropic LC and in some embodiments the LC is a lyotropic LC. Additional examples of liquid crystals, include, but are not limited to, 4-cyano-4'-pentylbiphenyl (5CB) and 7CB. A large listing of suitable liquid crystals is presented in "Handbook of Liquid Crystal Research" by Peter J. Collings and Jay S. Patel, Oxford University Press, 1997, ISBN 0-19-508442-X, incorporated herein by reference.

The technology comprises use of polymeric liquid crystals in some embodiments. In some embodiments, the LC is a cholesteric liquid crystal and in some embodiments the LC is a ferroelectric liquid crystal. In some embodiments, the LC is smectic C, smectic C*, a blue phase, and/or a smectic A LC. It is further envisioned that LCs useful in the invention may further include additions of dopants such as, but not limited to, chiral dopants as described by shitara H, et al. (Chemistry Letters 3: 261-262 (1998)) and Pape, M., et al. (Molecular Crystals and Liquid Crystals 307: 155-173 (1997)). The introduction of a dopant permits manipulation of the liquid crystal's characteristics including, but not limited to, the torque transmitted by the liquid crystal to an underlying surface. Other dopants, such as salts, permit manipulation of the electrical double layers that form at the interfaces of the liquid crystals and thus permit manipulation of the strength of anchoring of the liquid crystal at the interface. A number of methods for preparing interfaces between liquid crystals and aqueous phases lie within the scope of the present invention. An approximately planar interface can be prepared by a film of liquid crystal in contact with an aqueous phase, or alternatively a curved interface can be prepared by using a droplet of liquid crystal dispersed in an aqueous phase. The scope of the invention is not limited by the methods by which interfaces between aqueous phases and liquid crystals can be prepared by those skilled in the art.

In some embodiments, the liquid crystals may preferably be selected from MBBA, EBBA, E7, MLC-6812, MLC 12200, 5CB (4-n-pentyl-4'-cyanobiphenyl), 8CB (4-cyano-4'octylbiphenyl) and 4-(trans-4-heptylcyclohexyl)-aniline.

II Devices

Devices Comprising a Defined Headspace (i.e., Microfluidic Cells)

In some embodiments, the devices according to the technology comprise a headspace to control diffusion of analytes above the LC. In this embodiment, the device comprises a substrate having a micropillared area that is chemically functionalized with a surface chemistry that is specific for the target analytes. The micropillared area is filled with the LC using capillary action to form a thin (e.g., approximately 1 to 20 microns, e.g., 5 microns) film. This sensor substrate is then paired with a glass substrate with a headspace (e.g., having a height of 1 to 100 microns, e.g., 20 microns) to allow controlled diffusion of the targeted analytes above the LC film. In some embodiments, the headspace is variable. In some embodiments, the first and second surfaces form a compartment having first and second open ends, wherein the headspace at the first end is from 1 to 20 microns and the headspace at the second end is from 21 to 100 microns. In some embodiments, the top surface is functionalized with (Tridecafluoro-1,1,2,2-tetrahydrooctyl)-trichlorosilane (OTS) on which the LC film does not spread. This minimizes or eliminates the forming and spreading of small LC droplets that could touch the top surface and obstruct the diffusion of gas across the head space. This embodiment of the device provides sensitive detection of analytes in real-time and provides a cumulative detection of analytes. Additionally, in this embodiment, varying the thickness of the headspace between the LC film and the OTS coated surface provides control of the dynamic range of the device. In some embodiments, a spacer is placed between the two halves of a sandwich type of a cell. In some embodiments, the spacer comprises a material such as mylar or some polymer material having a defined thickness.

Devices Comprising a Channel

In some embodiments, devices according to the technology comprise a channel (e.g., a microfluidic channel) having a functionalized surface. In contrast to these embodiments of the technology, some conventional LC sensors are fabricated by supporting a thin film of LC on a chemically functionalized surface. When these sensors are exposed to the environment to be tested, the analyte diffuses through the LC film and then interacts with the surface chemistry to change the LC orientation. However, in these configurations (e.g., with the LC film in place), the analyte has to diffuse through the LC film to reach the surface chemistry. In some cases, problems arise, especially with the sensitivity of the sensors. For example, since the analyte has to diffuse through the LC film, the LC acts as a diffusion barrier that consequently reduces the sensitivity of the device. As such, the sensitivity of detection is limited by the partition of the gas through the LC film. Additionally, if the analyte reacts with the LC, some analyte is consumed before it reaches the active surface.

Accordingly, provided herein are embodiments that address sensor sensitivity using a two-step process in which the chemically functionalized surface is first exposed to the analyte and then the LC is added to contact the modified surface. The region that had been exposed to the analyte exhibits a different LC orientation relative to the unexposed regions. This approach is, in particular, very effective if the analyte irreversibly reacts with the surface chemistry.

In some embodiments, the technology is related to a microfluidic device. Embodiments of the device according to the technology comprise well defined microchannels formed on a PDMS (polydimethylsiloxane) slab that is paired with a chemically functionalized surface. The gas sample containing the analyte is flowed through the microfluidic channel defined between the PDMS slab and the chemically functionalized surface. After a predefined time, the PDMS channels are removed and a thin film of LC is overlaid between an OTS coated slide and the now-reacted chemically functionalized surface. The length of the channel that reacted with the analyte shows a different LC orientation (and thus appears different when interrogated by, e.g., polarized light) compared with the background or with an unreacted region of a channel. For a fixed flow rate and exposure time, the length of the channel having a changed LC orientation is a function of concentration of the analyte. Thus, by measuring the length of the channel having a different LC orientation the concentration of the analyte is determined. This approach not only allows a sensitive detection of analytes, but also provides a quantitative method to determine an unknown concentration of an analyte. Moreover, this approach provides efficient sampling of analytes by increasing the number of analyte molecules that come in contact with the chemically functionalized surface, thereby significantly improving the sensitivity of detection of gases.

Dosimeters

In some embodiments, the sensors find use in a dosimeter for, e.g., personal monitoring of a person to an analyte such as a toxic gas (e.g., formaldehyde (HCHO), $H_2S$, $NO_2$, organic compounds, etc.). For example, it is contemplated that some embodiments of the technology allow detection of a concentration range of an analyte when exposed for a particular amount of time, e.g., 0.15 to 10 ppm HCHO after an 8-hour exposure. Devices are constructed and verified by exposing the dosimeters to analyte (e.g., HCHO gas) inside an exposure chamber by delivering the analyte at a known concentration and flow rate (e.g., HCHO at a nominal flow rate of 200 ml/minute) to minimize the linear velocity (<1 cm/minute) at the dosimeter surface and thus mimic a static exposure. After exposure, optical images of the dosimeter are captured using a digital camera and analyzed using image processing software to measure the response, e.g., by the decrease in light intensity (brightness) between the crossed polarizers or by the increase in the width of the dark front.

While an understanding of the mechanism is not required to practice the technology, in some embodiments the sensitivity of detection depends, for example, on the chemical functionality of the LC composition and/or the thickness of the LC film. For example, data collected during the development of particular embodiments of the technology demonstrated a selectivity of MBBA, a LC known to significant concentrations of 4-methoxybenzaldehyde and 4-butylaniline, for selective detection of HCHO. The specificity of the response of the MBBA-based LC to HCHO is consistent with the response being caused by a reaction between the 4-butylaniline present in MBBA. This reaction, driven by mass action in the presence of HCHO results in a Schiff's base compound that causes LC to undergo phase transition and the LC film appears dark when viewed between crossed polars. Accordingly, it is contemplated that other LCs having different compositions and chemical functionalities, when mixed with different amines provide sensitive detection of HCHO (Table 1).

TABLE 1

Properties of LCs and amines

| Liquid Crystals | Source | Composition | Functional Group | $T_{NI}$ (° C.) |
|---|---|---|---|---|
| MBBA | Aldrich | schiff's base | imine, ether | 45 |

TABLE 1-continued

Properties of LCs and amines

| Liquid Crystals | Source | Composition | Functional Group | $T_{NI}$ (° C.) |
|---|---|---|---|---|
| 5CB | Merck | cyano biphenyl | nitrile | 35 |
| E7 | Merck | cyano bi & terphenyls | nitrile | 65 |
| TL 205 | Merck | fluorinated bi & terphenyls | fluorine | 87 |

Amines (Aldrich)

Aniline o-Toluidine

4-Butylaniline 2,4 Dinitrophenylhydrazine

Exemplary properties of some mesogens are provided in Table 2 (phase transition temperatures $T_N$ are provided in degrees Celsius).

Moreover, it is contemplated that the response to analyte varies with the thickness of the LC film. Accordingly, in some embodiments the devices comprise a micropillared substrate (as described herein) that determines the thickness of the LC film. For example, some embodiments comprise micro-pillars having heights of 2, 5, or 10 microns as produced using conventional photolithography. As described for the technology provided, substrates are filled with an LCs (e.g., as provided in Tables 1 or 2) using capillary action and the LC-filled substrates are paired with a clean glass substrate with a fixed head-space (e.g., 25 or 45 microns) to form a dosimeter badge.

Various combinations of LC composition and film thickness are contemplated to provide various sensitivities to a number of analytes. In particular, different functional groups (e.g., for those embodiments that comprise a functional group) provide for the specific detection of different analytes. The thickness of the LC is related to the rate of interaction of the analyte with the functional groups and the size of the headspace is related to the rate of exposure of the device to the analyte.

The evolution of a dark front results in a decrease in the measured brightness. In some embodiments a change of at least 10% from an initial unexposed value is a response to analyte exposure. For example, as applied to the detection of HCHO, preferred embodiments detect 0.15 ppm of HCHO after an 8-hour exposure. Fabricating embodiments comprising various combinations of LC, film thickness, and a defined headspace provide for control of the dynamic range of the devices. For example, some embodiments provide a dynamic range of 0.15 to 10 ppm (e.g., as for some embodiments that detect HCHO) and some embodiments provide a dynamic range of 0.1 to 15 ppm (e.g., as for some embodiments that detect $H_2S$). In some embodiments, the device (e.g., a dosimeter) is exposed to sample on 1, 2, 3, 4, or more edges while the remaining edges are sealed to prevent or minimize the entrance of analyte through those edges. The total surface area of the LC exposed to a sample possibly comprising an analyte is related to the response of the device to the analyte. In some embodiments, the distance the dark front travels in to the dosimeter is related to the response of the device to the analyte.

By testing embodiments of the devices using known amounts of analyte, a dose-response curve is produced that correlate a measured response to an analyte concentration. After measuring the device response to an unknown concentration of analyte, the dose-response curve provides for the calculation of the unknown concentration from the measured response. Statistical analysis of the response to known concentrations of analyte provides an estimate of the error in a measurement of an unknown.

Testing the device response to potentially interfering compounds verifies the specificity of the response. For example, devices specific for a particular analyte do not respond or have a minimal response to other substances that are not the analyte. In some embodiments, an LC and/or functional group is chosen that shows a maximal response to the target analyte and a minimal or no response to non-target substances. Some embodiments comprise a filter (e.g., a membrane, adsorbent, zeolite, etc.) to prevent or minimize the response of the device to particular non-analyte substances. In addition, dosimeters are tested to verify that temperature changes and gas flow rate do not adversely affect the device performance. For example, some embodiments provide a housing for the device that controls the flow rate of the sampled environment to the sensing surface. The shape and configuration as well as the size of the aperture that allows the passage of sample gas to access the LC device are related to the control of the flow rate.

Some embodiments provide a device that is responsive to several substances, e.g., a class of compounds (e.g., organic, aliphatic, aromatic, halogen, etc.) or particular functional groups.

III Detection

Detection Based on Phase Transition

Figure 33:
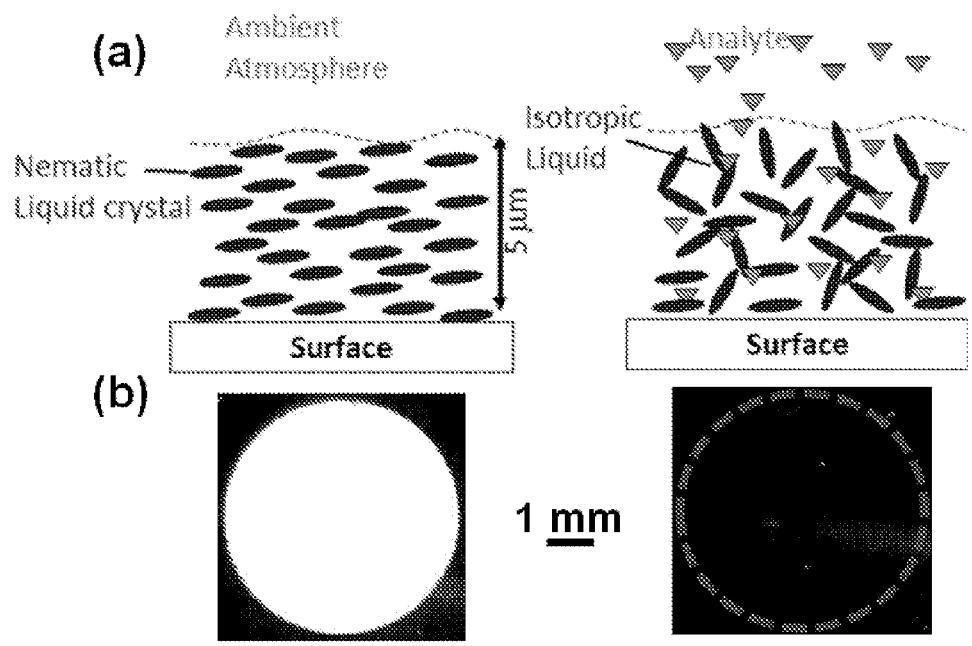
FIG. 33 is schematic showing a principle of detection of organic vapors using liquid crystals (LCs) using phase transition. The initial and post exposure appearance of the LC sensor depends on the surface the LC is laid onto. (A) A sensor consists of a thin film of LC supported on a substrate with polymeric micropillars and (B) initially appears bright (left). When the sensor is exposed to analyte (e.g., toluene), the LC material turns into an isotropic material and appears dark (right) between crossed polarizers.

LC materials typically comprise rod-shaped organic molecules. These molecules form anisotropic condensed phases that possess long-range orientational ordering (crystal-like) but lack positional ordering (liquid-like). The long-range ordering of molecules within an LC gives rise to anisotropic optical properties—so-called optical birefringence. Absorption of analytes (e.g., VOCs) into the LC phase disrupts the long-range order of the LC, thus giving rise to a phase transition to an isotropic material. This phase transition, in turn, leads to distinct changes in the optical appearance of the LC. FIG. 33 illustrates the principles underlying the LC sensor for detection of analytes using a phase transition. The sensor comprises a micrometer-thick film of LC supported on a solid substrate decorated with polymeric micro-pillars (5 μm diameter, 10 μm center-to-center spacing). The micro-pillars are used to form mechanically robust thin films of the LC. Prior to exposure to toluene, the LC possesses a bright visual appearance between crossed polarizers. When the sensor is exposed to the test environment containing analytes, analyte molecules rapidly diffuse into the LC film (FIG. 33a) to induce a nematic-to-isotropic phase transition. The process of diffusion into the LC is rapid, predictable, and the phase transition in LC is denoted by a striking change in optical appearance of the sensor (FIG. 33b). In other embodiments of the invention, the VOC causes a change from one liquid crystalline phase into another liquid crystalline phase. It is not necessary that the phase transition involve an isotropic phase.

Detection Based on Structural Change of LC Confined in Micro/Nano Structures

Figure 34:
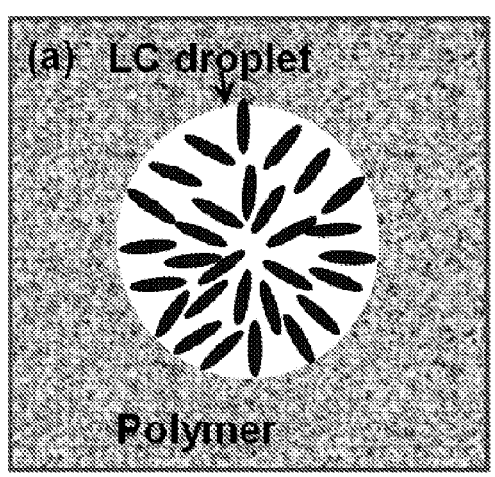
FIG. 34 is a schematic showing a principle of detection of VOCs using confined LCs. (a) A LC droplet is encapsulated in a micro/nano structure formed in a polymeric material that absorbs VOCs. Upon exposure to VOCs, the polymer structure changes to an anisotropic shape due to the constrained boundary conditions. (b) As a result, the LC undergoes change in orientation inside the modified structure.
Figure 34:
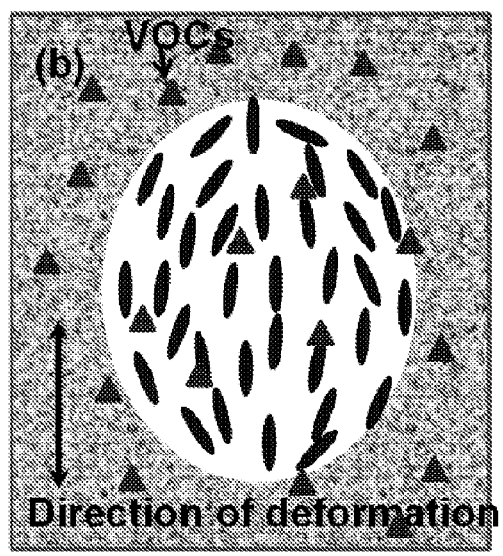

When a LC droplet is confined by a micro and/or a nano structure, the LC molecules inside the droplet assume a well-defined configuration that is determined by the properties of the material forming the structure, the dimensions of the structure, and the LC materials. The absorption of analyte molecules induces a change in the structure and dimensions of the confining structure. The structural changes in the confining material, in turn, induce a change in the ordering of the LC inside the cavity. By appropriate selection of the materials for confinement, structures for encapsulating LCs, and LC materials, the selectivity and sensitivity of detection is tuned. FIG. 34 shows a basic principle behind this approach of detection where a LC droplet is confined inside a polymer matrix that is known to adsorb target analytes. In this example, the polymer material provides LC alignment perpendicular to the LC-polymer interface. The polymer matrix is confined between two rigid structures so that it can deform only along the one direction (indicated by the arrow). Upon exposure to analyte, the polymer deforms to an anisotropic shape inducing an ordering transition in the LC droplet. Various embodiments of the same basic principle are envisioned. For example, one embodiment involves fabrication of well-defined polymer dispersed LC structures that deform/change upon exposure to an analyte such as a VOC.

Detection Based on Dewetting of Film Supporting LCs

Figure 35:
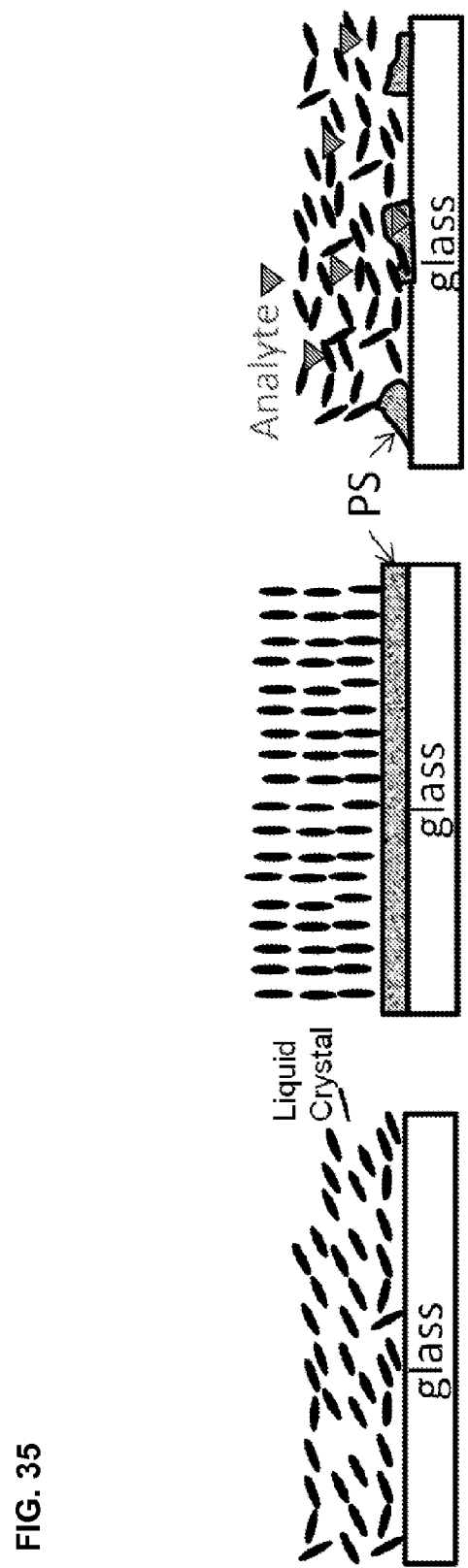
FIG. 35 is a schematic showing a basic principle of detection of VOCs using dewetting-induced orientational transition of LCs. A glass substrate is coated with polymer (PS) and a film of LC is supported on the polymer film. When the film is exposed to VOCs, the film dewets the surface and the orientation of LC changes.

The stability of a thin film of material deposited on a solid substrate depends on a number of parameters such as the surface energy of the substrate, the physical and chemical structure of the deposited material, the thickness of the film, etc. Some polymeric materials such as polystyrene form a stable film on glass or silicon. The PS film has been shown to dewet if the thickness of the film is lower than a critical value or if the temperature of the film is raised above a critical value. Since the effect of exposing a polymer film to analytes (e.g., a VOC such as toluene) is very similar to heating (e.g., exposure to toluene lowers the glass transition of polymer), it is anticipated that exposure to some analytes will induce the dewetting of the film. If the underlying substrate and the polymer materials are selected so that the orientation of LC on the substrate relative to the orientation of LC on the substrate coated with polymer is different, exposure to analyte will lead to a change in the orientation of the LC. The sensitivity of detection can be enhanced by selecting polymer material that has a high absorption of analytes of interest. The basic principle behind the dewetting-induced orientational transition is schematically shown in FIG. 35. The main difference between the analyte-induced orientational transition and the dewetting approach is that in an analyte-induced orientational transition the LCs remain in contact with the chemically functionalized surface before and after exposure. In this approach, the chemically functionalized surface (in this case polymer) is modified and physically dewets the substrate. As a result, the LC comes in contact with the underlying surface. The film that undergoes the dewetting transition can be formed from a number of organic or inorganic materials.

Figure 36:
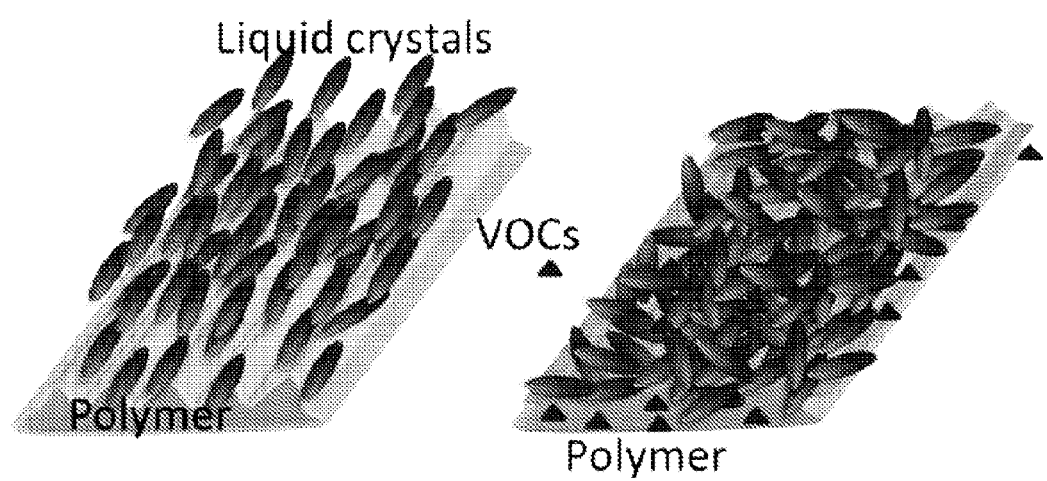
FIG. 36 is a schematic showing a basic principle of detection of VOCs based on structural changes on the surface supporting a LC film. A polymer film that is known to absorb target analyte is deposited and mechanically sheared to generate micro-structures on the surface. These microstructures align LC in a pre-defined direction. Absorption of VOCs into the polymer film erases the microstructures inducing a change in orientation of LCs film.

Detection Based on Changes on Microscopic Structures on a Polymer Film Supporting LC Film The orientation of an LC at the LC-substrate interface is extremely sensitive to changes in physical and chemical properties of the LC-substrate interface. Rubbed polymer (such as polyimide) films have been widely used in LC display industries to achieve uniform planar alignment of LCs. Although the exact mechanism for the rubbing-induced LC alignment is not fully understood, it is believed that anisotropic physical interactions related to anisotropy in surface morphology are responsible for uniform alignment of LCs on rubbed polymer surfaces. However, an understanding of the mechanism is not required to practice the technology. Polymer materials, that are known to cause swelling as a result of VOC absorption, can be deposited on a solid substrate and mechanically sheared to generate micro-structures similar to those used for LCD displays. These surfaces initially promote uniform alignment of LCs. Absorption of analytes such as, e.g., VOCs, induces structural changes at the LC-surface interface. This structural change leads to a change in the orientation of the LC film. This principle was used (see FIG. 36) to achieve a uniform alignment of LC on surfaces coated with polymer films, e.g., films formed from poly(vinyl acetate) (PVAc) and polystyrene (PS). It is contemplated that a polymeric or liquid crystalline polymeric film can be stabilized (e.g., thermally, electrically, or mechanically) in a thermodynamic non-equilibrium state. In such a state, the film, upon exposure to analyte, relaxes to a lower energy state by releasing the stored energy. As a result, the LC film supported on this film undergoes orientational transition.

Detection Based on Dissolution of Ionic Compounds

Figure 37:
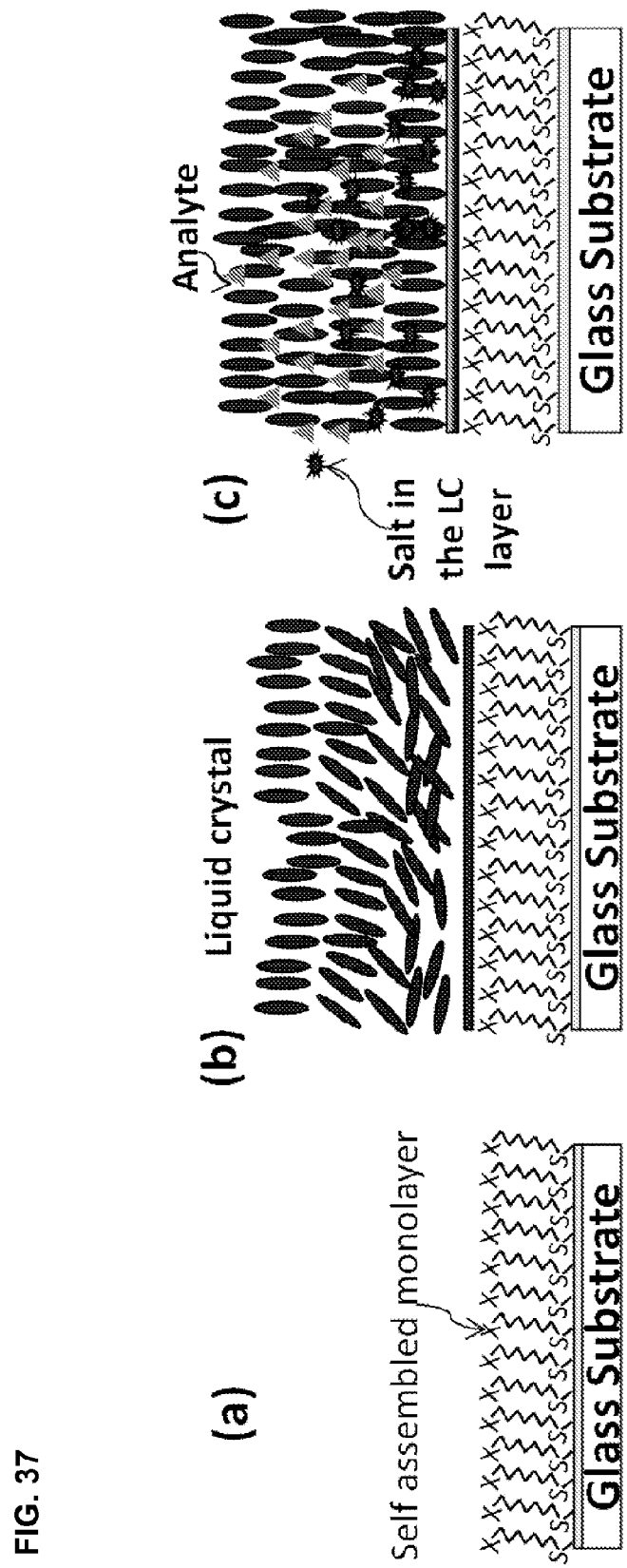
FIGS. 37A, 37B, and 37C are a schematic showing a basic principle of detection of VOCs using orientation transition induced by dissolution of ionic salt into LC film. A thin film of ionic salt is deposited on self-assembled monolayer formed on a gold coated surface. When the LC film is exposed to target VOC, the ionic salt radially dissolves into the LC film thereby inducing orientational transition in the LC film.

Controlling the presence of ionic compounds in an LC provides a functionality to detect analytes. Two approaches are contemplated. First, in some embodiments, the presence of certain ionic compounds in the LC induces a LC orientation change at the LC-surface interface. For example, a surface prepared with tetrabutylammonium perchlorate was shown to induce a homeotropic alignment as it dissolved into the LC layer. As the molecular weight and chain lengths of the quaternary ammonium compounds increases, their solubility in non-polar solvents (e.g., toluene) increases. An LC film supported on an appropriate quaternary ammonium salt coated surface is thus anticipated to dissolve this salt upon toluene exposure and produce a change in the LC orientation. Second, in some embodiments, a cyanobiphenyl LCs (e.g., 5CB, E7) aligns perpendicularly on surfaces decorated with bivalent and trivalent metal perchlorate salts. Besides perchlorate salts, only a few other metal salts, such as tetraphenylborate (a metal salt compressing a bulky anion), align LC perpendicular to the surface. In addition, these salts with large anions possess high solubility in toluene or other non-polar organic solvents. In contrast to the metal perchlorate salts, bivalent and trivalent metals with anions such as acetate, chloride, nitrate, etc. are insoluble in non-polar solvents and are known to align LCs parallel to the surface. Thus, a surface can be prepared from a mixture of metal tetraphenylborate and a metal acetate salt in an adequate ratio to induce a homeotropic alignment initially. As the surface is exposed to analytes such as a VOC the tetraphenylborate is anticipated to enter into the LC layer followed by a LC orientation change due to a change in the surface composition. A schematic of the principle is shown in FIG. 37.

Figure 38:
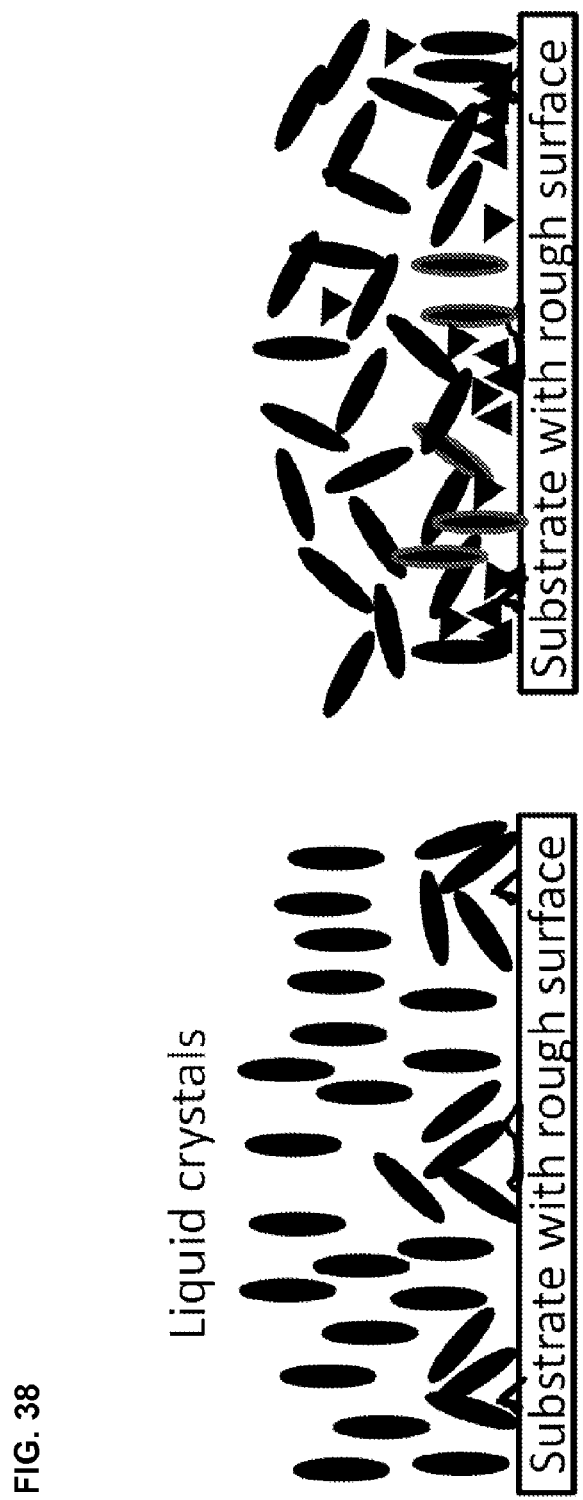
FIG. 38 is a schematic showing a basic principle of detection of VOCs using orientation transition induced by localized concentration at defect sites in LC. A thin film of LC is supported on a rough surface that generates local defects in the LC at the microscopic level, yet providing uniform alignment on macroscopic level. When the surface is exposed to VOCs, the microscopic defects locally concentrate the VOC molecules at the defect sites leading to ordering transition in the LC film

Detection Based on Orientational Transition Induced by Localized Concentration at Defect Sites in LC In some embodiments, a thin film of LC is supported on a locally rough surface (for example etched silicon dioxide) that possesses sharp defects while promoting well defined orientation (for example, an orientation that is substantially perpendicular to the surface) of the LC. When this film of LC is exposed to an environment containing an analyte (e.g., VOCs), the analyte molecules diffuse through the film of LC and concentrate locally at the defect sites. When the local concentration of analyte at the defect site is greater than the threshold needed to induce an orientational transition, the LC film undergoes the orientational transition (FIG. 38). Related embodiments involve the use of a blue phase of a LC that is known have defect states in the film itself (as opposed to the defect being in the surface supporting the film). These defect states concentrate the analyte molecules locally to induce melting at these defect sites.

Detection Based on Swelling of Polymer Beads Dispersed in LC

Figure 39:
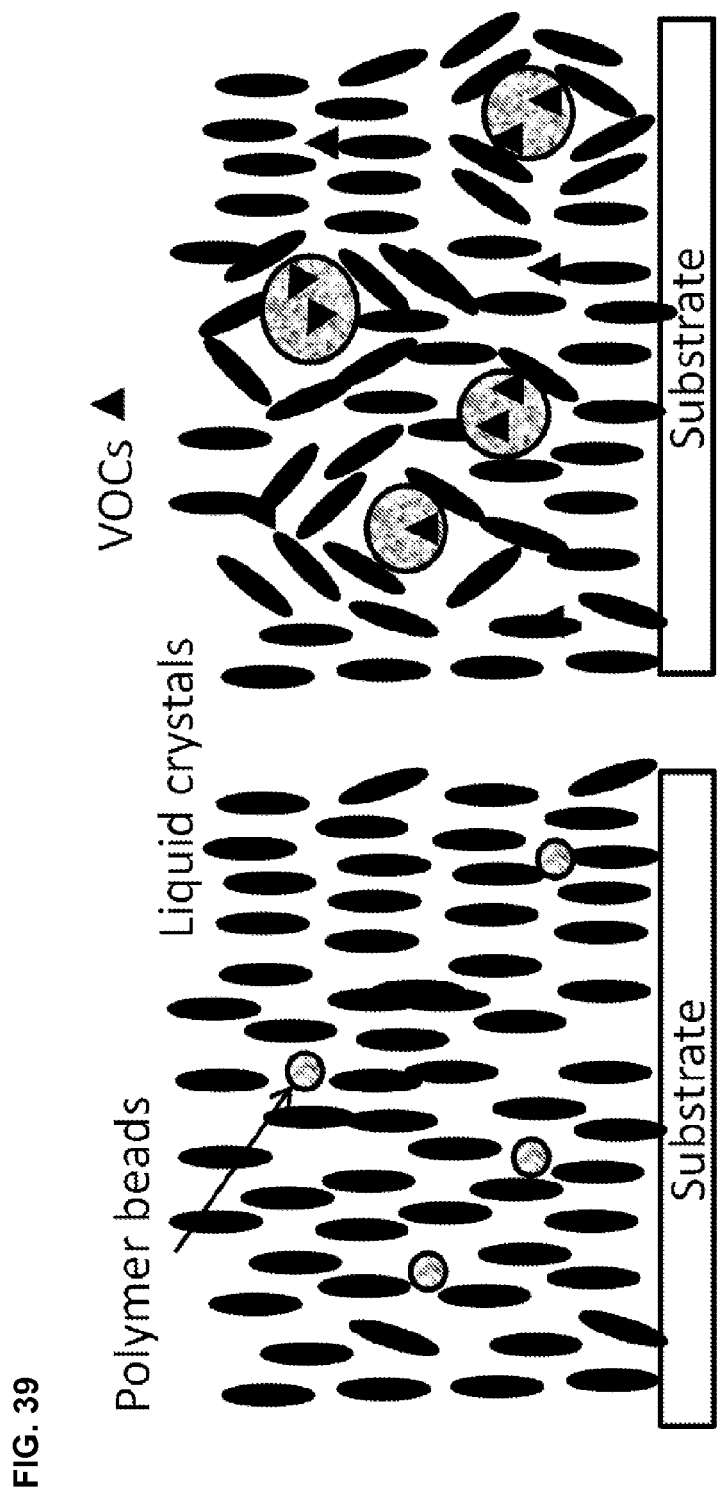
FIG. 39 is a schematic showing a basic principle of detection of VOCs utilizing swelling of polymer beads suspended in LC. Polymer beads are suspended in a LC film that is supported on a surface providing uniform alignment of LC. Absorption of VOC in the polymer beads swells the beads and induces distortion in the LC alignment around the beads. The distorted LC around these beads scatters light.

In some embodiments, micro and/or nano scale polymer beads composed of materials that are known to swell by absorbing certain analytes (e.g., VOCs) are suspended in the LC matrix. The dimension of the beads is small enough not to distort the LC director when they are suspended. The LC is uniformly aligned and the LC film does not scatter light. When this film is exposed to an environment containing analyte, the beads swell significantly due to absorption of analyte molecules. Once a dimension of the beads exceeds a critical value the beads distort the director distribution in the LC matrix. As a result of distortion in the director configuration, the LC film scatters light (FIG. 39). An extension of this approach is to use beads that are randomly distributed in the LC matrix. When the LC film with beads is exposed to an analyte, the density of the beads decreases (they become lighter) and they subsequently float on the top of the LC surface. If the beads are chosen to be opaque they will block the light transmitted through the LC film.

Detection of Gas Phase Compounds

The present technology provides methods and devices for the detection of gas phase compounds in a sample. The only limitations on size and shape are those that arise from the situation in which the device is used or the purpose for which it is intended. In some embodiments, the devices comprise a single substrate that is open to the environment on one surface. The device can be planar or non-planar. The device can be cylindrical in shape and in a linear or coiled format, and with one or two ends of the device open to the environment. Furthermore, it is within the scope of the present technology to use any number of polarizers, lenses, filters, lights, and the like to practice the present technology.

In some embodiments, devices comprise a mesogen. The present technology is not limited to any particular mechanism of action. Indeed, an understanding of the mechanism of action is not necessary to practice the present technology. Nevertheless, it is contemplated that the in some embodiments the mesogens forming the liquid crystal of the devices of the present technology have an affinity for the targeted compound. This affinity causes a phase transition of the liquid crystal in the presence of the target. Particular mesogens will transition from a higher order to a lower order following interaction with different molecules. The devices of the present technology are designed so that when gas phase compounds are present in a sample, the gas can enter detection regions of the device where mesogens are arrayed and cause a change in the phase order of the mesogen by interacting with the mesogen. This phase transition may be from one phase selected from the group consisting of an isotropic phase, a nematic phase, and a smectic phase to another phase selected from the group consisting of an isotropic phase, a nematic phase, and a smectic phase. The phase transition induces a change in the liquid crystal (e.g., a nematic region as opposed to an isotropic region) that can be detected in a variety of ways.

In some embodiments, the present technology provides substrates overlaid with mesogens into which the gas phase compound diffuses leading to a phase transition of the mesogen. In other embodiments, the gas phase compound interacts directly with a reactive moiety of the mesogen to induce the phase change of the mesogen. In still other embodiments, the gas phase compound diffuses into a mesogen composition containing a dopant and interacts with a reactive moiety on the dopant leading to a phase transition of the mesogen. In some embodiments, the gas phase compound interacts with a surface (e.g., a functional group attached to the surface) supporting the mesogen such that the interaction of the gas phase compound with the surface produces a change in orientation of the mesogen.

Accordingly, in some embodiments, the present technology provides substrates comprising at least one detection region comprising a mesogen composition comprising a reactive moiety that binds to or otherwise interacts with a gas phase compound. In some embodiments, the detection regions are discrete and created by arraying at least one reactive moiety on the surface of the substrate. In some embodiments, a plurality of mesogens with various reactive moieties is arrayed on the surface of the substrate so that multiplexed assays for a variety of gas phase compounds can be conducted or so that different interactions with a variety of reactive moieties can be used as a signature for a particular gas phase compound. In some embodiments, a liquid handler is used to deposit the mesogen composition in the detection region.

In some embodiments, a second substrate is provided that is configured opposite the first substrate so that a cell is formed. In some embodiments, the second substrate is also arrayed with a mesogen composition comprising a reactive moiety, while in other embodiments, the second substrate is free of reactive moieties. In some embodiments, the mesogen compositions comprising a reactive moiety are arrayed on the first and second substrates so that when the first and second substrates are placed opposite each other the arrays match to form discrete detection regions.

In some embodiments, the cell that is formed by the first and second substrates includes a space between the first and second substrates. In some embodiments, the space is formed by placing a spacer (e.g., in some embodiments made of mylar) between the first and second substrates. In some embodiments, the space is then filled with the desired liquid crystal. In still other embodiments, the substrates are arranged so that a sample can interact with or enter into the detection regions. In some embodiments, the substrates are fixed (e.g., permanently or removably) to one another. The present technology is not limited to any particular mode of fixation. Indeed, a variety of modes of fixation are contemplated. In some embodiments, the substrates are fixed to one another via adhesive tape. In preferred embodiments, the adhesive tape is 8141 pressure sensitive adhesive (3M, Minneapolis, Minn.). In other embodiments, the substrates are fixed to one another via a UV curable adhesive. In some preferred embodiments, the UV curable adhesive is PHO-TOLEC® A704 or A720 (Sekisui, Hong Kong). In some embodiments, glass spacer rods are utilized with the UV curable adhesive to provide spacing between the two substrates. In some embodiments, the glass spacer rods range from about 5 µM to about 100 µM, preferably about 25 µM, in thickness. It has been found that UV-curable adhesives are preferable as in some instances the adhesive tape reacts with the liquid crystal.

In further embodiments, the substrates are arranged in a housing. The housing can comprise any suitable material, and is preferably made of polymeric material, for example, a plastic. In preferred embodiments, the housing is sealed to the environment except for an opening adjacent to the detection region or regions. The opening preferably allows diffusion of air to the detection region. In some embodiments, the opening allows introduction of a liquid sample wherein gas emitted from a constituent in the sample impinges on the substrates and can be interrogated. In some embodiments, the opening is covered with a filter material that allows diffusion of air to the detection region, but does not allow entry of particulate matter such as dust, dirt, liquid, and insects into the detection region. In some embodiments, the filter is an aerosol filter that substantially prevents the introduction of aerosols into the detection region, but allows an analyte in vapor form to enter the detection region. In still more preferred embodiments, the devices comprise two or more filters positioned so as to allow air exchange though the device, and in particular, through the detection region. For example, the filters can be arranged at either end of the detection region. In further embodiments, the housing is moveable between an exposure mode and a reading mode. In the exposure mode, the detection regions are exposed to the environment, while in the reading mode, exposure to the environment is substantially or completely eliminated. It is envisioned that after the device has been exposed to the environment, the housing can be moved to the reading mode to prevent further exposure to the environment prior to readout.

In still further embodiments, the devices of the present technology comprise a unique identifier. In some embodiments, the unique identifier is a bar code. In other embodiments, the unique identifier is an RFID chip. It is contemplated that the unique identifier can provide information such as a serial number, user identification, source identification, and the like.

In use, the device is placed in an area where the gas phase compounds are suspected of being present. The device is allowed to remain in place for a period of time (the exposure period, e.g., from one or more minutes to one or more hours to one or more days to one or more weeks or more).

In other uses, a liquid sample that is biological or pharmaceutical in nature and suspected of containing bacteria is introduced into the device. The sample is allowed to incubate for a period of time (e.g., for the exposure period, e.g., from 15 minutes to 4 days). In a preferred use, the device receives a liquid sample and is incubated at 37° C. for 1 hour with shaking to permit replication of bacteria that leads to release of metabolic gases.

Following the exposure period, the cell is assayed for whether a change in the liquid crystal phase has occurred over one or more of the detection regions. Although many changes in the mesogenic layer can be detected by visual observation under ambient light, any means for detecting the change in the mesogenic layer can be incorporated into, or used in conjunction with, the device. Thus, it is within the scope of the present technology to use lights, microscopes, spectrometry, electrical techniques and the like to aid in the detection of a change in the mesogenic layer. In some embodiments, the presence of gas phase compounds is detected by a change in the color and texture of the liquid crystal.

Accordingly, in those embodiments utilizing light in the visible region of the spectrum, the light can be used to simply illuminate details of the mesogenic layer. Alternatively, the light can be passed through the mesogenic layer and the amount of light transmitted, absorbed, or reflected can be measured. The device can utilize a backlighting device such as that described in U.S. Pat. No. 5,739,879, incorporated herein by reference. Light in the ultraviolet and infrared regions is also of use in the present technology. In other embodiments, the device, and in particular the detection region, is illuminated with a monochromatic light source (e.g., 660-nm LEDs). In some embodiments, the cell is placed in between cross-polarized lenses and light is passed though the lenses and the cell. In still other embodiments, the detection region is masked off from the rest of the device by a template or mask that is placed over the device.

The devices of the present technology are useful for measuring cumulative exposure to gas phase compounds. In some embodiments, cumulative exposure is assayed by determining the advancement of a wavefront in the detection region. It is contemplated that the wavefront advances from an opening associated with the detection region. The distance of advancement correlates to the degree of exposure to gas phase compounds and is thus quantitative. In particular, it is contemplated that the rate of progress of the wavefront into the detection region depends on the concentration of gas phase compound to which the device is exposed. In some embodiments, the front movement in millimeters is plotted against elapsed time in hours. The resulting plot obeys a linear fit (preferably with a coefficient of correlation of greater than 0.95) that is characteristic of the concentration of a gas phase compound in the sample (e.g., local atmosphere). In some embodiments, wavefront advancement is measured by capturing a digital image or video in real time of the detection region and determining the area and length (e.g., in pixels) of the wavefront relative to the opening. In some preferred embodiments, the image is analyzed with an image manipulation and analysis program such as ImageJ (NIH). The pixels can then be converted into a distance in millimeters if necessary. In other embodiments, the image is analyzed by converting the image with a % white command so that the area in which the liquid crystal has been disrupted by the gas phase compound appears white. The degree of advancement of the wavefront can be determined by measuring pixel intensity and determining the point of image drop-off from high intensity (white) to low intensity (black).

The devices of the present technology can also be used to identify particular gas phase compounds. In some embodiments, the detection region of the device comprises an array of at least two different mesogens. The pattern of response to the at least two different mesogens can be used to identify particular compounds.

In some embodiments, gasoline vapor, or a component of gasoline vapor such as octane, is detected by phase transition of a liquid crystal. In some preferred embodiments, devices for detecting gasoline vapor comprise at least one surface in contact with a liquid crystal composition, wherein the liquid crystal composition. In some embodiments, the liquid crystal composition comprises a mesogen selected from the group consisting of MBBA, EBBA, E7, MLC-6812, MLC 12200, 5CB (4-n-pentyl-4'-cyanobiphenyl), 8CB (4-cyano-4'octylbiphenyl) and 4-(trans-4-heptylcyclohexyl)-aniline. In some embodiments, the device is exposed to a sample suspected of containing gasoline vapor, for example an atmospheric sample, or is exposed to an area suspected of containing or susceptible to containing gasoline vapor. The presence of gasoline vapor is indicated by a phase transition of the liquid crystal in the device. The phase transition may be observed visually or detected by a method such as measurement of change in optical anisotropy, magnetic anisotropy, dielectric anisotropy, and measurement of phase transition temperature.

Reflection-Based Probing

Some embodiments of devices according to the technology comprise a Fabry-Perot filter. The present technology is not limited to a particular mechanism. Indeed, an understanding of the mechanism of the present technology is not needed to practice the technology. Nevertheless, when electromagnetic radiation propagates through an interface between two dielectric media it undergoes reflection at the interface. If a dielectric material is sandwiched between two highly reflecting mirrors forming a cavity, multiple reflection of radiation occurs in the cavity. For a given thickness and dielectric properties of the cavity, the reflected electromagnetic radiation interferes constructively and shows a maximum at a particular wavelength. The wavelength at which the reflected radiation shows a peak in intensity depends on the thickness of cavity and the dielectric property of the cavity. When the refractive index of the cavity changes, the wavelength at which the maximum reflection occurs also changes. In some embodiments, the mirrors are functionalized with receptors or other moieties that interact with the specific analyte and binding of the target induces an orientational transition of the LC and hence a change in the dielectric property of the cavity. This change in the dielectric constant results in a shift in the wavelength at which the reflected intensity is maximal. In some embodiments, the analyte interacts directly with the LC to effect a change in the dielectric properties of the cavity.

In some embodiments, the Fabry-Perot filter devices comprise a first surface (e.g., an interior surface) displaying one or more mesogen compositions. In some embodiments the mesogen composition comprises a reactive moiety. In some embodiments, the surface is reflective. In some embodiments, the first surface is gold. In some embodiments, the gold is deposited on a supporting substrate, such as glass or silicon. Other suitable substrates are described in more detail above. In further embodiments, the devices comprise a second surface coated in a reflective material, preferably gold. In some embodiments, the second surface also displays one or more mesogen composition. In some embodiments, the mesogen comprises a reactive moiety. In some embodiments, the first and second surfaces are configured opposite one another to form a chamber there between. Preferably, the chamber is fillable with a liquid crystal. Some mesogens that find use in forming the liquid crystal are listed above and include, but are not limited to, E7, MLC-6812, MLC 12200, MBBA, EBBA, 5CB (4-n-pentyl-4'-cyanobiphenyl), and 8CB (4-cyano-4'octylbiphenyl).

In some embodiments, at least one mesogen composition is deposited or otherwise interacts with the first or second surfaces. In some embodiments the mesogen comprises a reactive moiety. The present technology is not limited to any particular reactive moiety. Indeed, a variety of reactive moieties may be utilized, including, but not limited to, organic functional groups such as amines, carboxylic acids, drugs, chelating agents, crown ethers, cyclodextrins, or a combination thereof, a biomolecule such as a protein, an antigen binding protein such as a monoclonal antibody, a polyclonal antibody, a chimeric antibody, a humanized antibody, a Fab fragment, a single chain antibody, etc., a peptide, a nucleic acid (e.g., single nucleotides or nucleosides, oligonucleotides, polynucleotides, and single and higher-stranded nucleic acids) or combinations thereof.

The present technology is not limited to any particular substrate shape. Indeed, a variety of substrate shapes are contemplated, including, but not limited to, discs, cylinders, and spheres. Disc shaped devices are preferably configured as described above, with a single planar surface that is overlaid with a liquid crystal. In some embodiments, the discs have a diameter of between about 0.1 mm to 10 cm, e.g., about 1 mm to about 100 mm. In some embodiments, highly reflecting mirrors are prepared by depositing ~500-nanometer thick gold films on clean glass slides (or plastic films) using an electron beam evaporator. In further embodiments, gold mirrors are layered with mesogens that provide a reactive moiety. In some embodiments, glass fiber rods (e.g., approximately 25-micron diameter) mixed in isopropanol are sprayed uniformly over one of the functionalized mirrors. These rods act as spaces defining the thickness of the dielectric cavity. An optical cell is fabricated forming a cavity between two reflecting mirrors. In some embodiments, the mirrors are glued together using UV curable adhesives. The cavity is then filled with a liquid crystal such as 4-n-pentyl-4'-cyanobiphenyl (5CB). The present technology is not limited to a particular mechanism of action. Indeed an understanding of the mechanism of action is not necessary to practice the present technology. Nevertheless, without exposure to the target analyte, the liquid crystals assume one phase (e.g., nematic). In some embodiments, the mirror assembly is placed in the path of the light in a spectrometer. For the optimized thickness, a peak appears in the transmitted intensity at a particular wavelength determined by the ordinary refractive index of the LC materials. In some embodiments, upon exposure to an analyte, the liquid crystal undergoes a phase transition (e.g., isotropic). In some preferred embodiments, the device is placed in a light path. A peak appears at a wavelength that corresponds to the average refractive index of the nematic phase. The shift in the peak position of the transmission spectrum indicates a change in the refractive index of the cavity caused by the phase transition of the liquid crystal that is induced by interaction of the analyte with mesogen and/or with the reactive moieties of the mesogen on the surface.

In some embodiments, hollow polymer cylinders (about 100 to 1000 microns in diameter, e.g., about 500 micron in diameter; about 1 mm to 1 cm in length, e.g., about 5 mm in length) are first coated with a reflective material such as gold. In some embodiments, the coating is from about 50 to about 1000 nm in thickness, e.g., about 500 nm thick. A spacer is then formed on the cylinder. In some embodiments, the spacer is from about 50 to about 200 microns in thickness, e.g., about 25 microns. In some embodiments, the spacer comprises glass fiber rods with a diameter of 25 microns (such as from EM Industries) or plastic micropearls (spheres) of diameter 25 micron (such as from Sekesui Chemicals, Hong Kong). In some embodiments, these spacers are mixed in isopropyl alcohol and then sprayed onto the cylinders. A ~25-micron sacrificial layer of photoresist is then coated to these cylinders. Examples of useful photoresist layers include, but are not limited to SU8 2010 from Michochem. Another thin nanoporous layer of gold is deposited on top of the sacrificial layer. The gold film with nanopores is strongly reflecting but allows small molecules to penetrate through it. The sacrificial layer is then dissolved in acetone. The spacers in between two gold surfaces act as supporting struts. These hollow cylinders are then filled with a liquid crystal. In some embodiments, the first surface is spherical and a second surface and chamber are formed as described for the cylinder embodiments.

In other embodiments, the devices of the present technology form a rugate filter. Again, the present technology is not limited to a particular mechanism. Indeed, an understanding of the mechanism of the present technology is not needed to practice the technology. Nevertheless, as the electromagnetic radiation propagates through a number of interfaces between dielectric layers, multiple reflections occur at each interface and a portion of the radiation is transmitted and a portion of it is reflected. If the dielectric constant of the medium exhibits sinusoidal variation, then the reflected intensity shows a peak in the reflected intensity at a wavelength that depends on the average dielectric constant and the amplitude of sinusoidal variation of dielectric constant. The position of the reflected peak in the electromagnetic spectrum shifts as the average refractive index of the sinusoidal variation changes. Accordingly, in some embodiments, a sinusoidal variation in the dielectric property is created by fabricating porous silicon with sinusoidal porosity gradient along the depth. See, e.g., Li et al. (2003) *Science* 299: 2045-47; Seals et al. (2002) *J. Applied. Phys.* 91(4): 2519-23; Schmedake et al. (2002) *Adv. Mater.* 14(18): 1270-72; Link et al. (2003) *Proc. Nat'l Acad. Sci USA* 100(19): 10607-10, all of which are incorporated herein by reference in their entirety. When the pores are filled with LCs, the LCs take on a specific phase. Upon exposure to the target analyte the LC undergoes a phase transition, which induces a change in the dielectric constant of the pores resulting in a shift in the position of the peak.

The present technology is not limited to the use of any particular type of silicon substrate. In some embodiments, the silicon substrate is a p-type, boron-doped silicon wafer with about a 1 mOhm-cm resistivity. In some embodiments the silicon wafer is polished. In some embodiments, the silicon substrate is ultrasonicated in isopropanol and then rinsed with water. In some embodiments, the silicon wafers are etched using an anodization-etching process with a mixture of 48% hydrofluoric acid and absolute ethanol (1:3 by volume) in a polytetrafluoroethylene (e.g., "Teflon") cell using a sinusoidally modulated current density to generate a sinusoidal variation in the porosity gradient. In further embodiments, the amplitude, period, and duration of the sinusoidal current density are adjusted to achieve the optimum porous size and distribution. It will be recognized that these parameters can be varied and optimized for the detection of different analytes. In still further embodiments, the current density is then ramped up so that a freestanding film of the porous silicon is detached from the substrate.

In still further embodiments, devices such as those described above are irradiated with electromagnetic radiation from the radio frequency region, including, but not limited to, frequencies between 1 KHz and 10 THz, and including the VLF, LF, MF, HF, VHF, UHF, SHF, and EHF regions of the radio spectrum. Studies have demonstrated that analysis of the reflection and/or transmission spectra of RF radiation can be used to identify analytes. See, e.g., U.S. Pat. Appl. 2004086929; Choi et al., *Int'l. J. High Speed Electronics and Systems* 13(4): 937-950 (2003); van der Weide, Springer Series in Optical Sciences (2003), 85:3 17-334 (2003), all of which are incorporated herein by reference. In some embodiments of the technology, a change in phase of a liquid crystal gives rise to a change in the reflection or transmission spectra of RF radiation. In further embodiments of the technology, the frequency of the radiation is in the 0.1 to 10 THz range. Methods known to those skilled in the art are used to analyze the radiation returned to a detector following interaction with the liquid crystal.

Photoluminescence

In some embodiments, a liquid crystal phase transition is detected by photoluminescence. The present technology is not limited to a particular mechanism of action. Indeed, an understanding of the mechanism of action is not necessary to understand the present technology. Nevertheless, when silicon with a nanometer scale porous structure is exposed to electromagnetic radiation having a short wavelength, typically in the ultraviolet region, electron-hole pairs are created. These excess carriers subsequently recombine and emit electromagnetic radiation. As the characteristic size of the structures in the porous silicon decreases to the nanometer scale, the band gap of the silicon nanostructures progressively widens. The recombination of these quantum confined carriers (electron-hole pair) in the wide band gap causes emission of electromagnetic radiation in the visible region. The wavelength of the emitted light depends on the dielectric constant of the materials filling the pores and the structure of the pores themselves. When the surfaces of the pores are filled with the liquid crystal, the liquid crystal takes on one phase (e.g., nematic). The porous silicon then emits light at a wavelength that corresponds to the radial distribution of the liquid crystal molecules. When the target analyte binds to the mesogen or to reactive moieties on the mesogens filling the pores, the liquid crystal undergoes a phase transition (e.g., to isotropic) causing a change in the dielectric constant. This results in a change in the position of the peak. It will be recognized that the present technology is not limited to any particular type of change in liquid crystal phase and that the described change from nematic to isotropic is exemplary. Other changes are also contemplated, including, for example, from smectic to nematic or changes in the amount of twist, where, for example, cholesteric liquid crystals are utilized.

In some embodiments, porous silicon substrates are fabricated and functionalized as described above. In further embodiments, the porous silicon is illuminated by a UV light. The exact wavelength of the UV light depends on the actual pore size, pore size distribution, and the refractive index of the liquid crystal material. The photoluminescence of the porous silicon is measured using a UV-visible spectrophotometer. The spectrum shows a peak at a wavelength corresponding to the phase of the liquid crystal. In some embodiments, the porous silicon is exposed to the target analyte in a closed chamber. The present technology is not limited to any particular mechanism of action. Indeed, an understanding of the mechanism of action is not necessary to understand the present technology. Nevertheless, as the target analyte binds to the mesogens or to a reactive moiety provided by the mesogen on the surface of the pores, the LC undergoes a phase transition. It is contemplated that the change in the phase of the liquid crystal corresponds to a change in the spectrum of radiation emitted by the porous silicon.

Fluorescence Based Detection

In some embodiments, detection is accomplished using a fluorescent reporter system. The present technology is not limited to any particular mechanism of action. Indeed, an understanding of the mechanism of action is not necessary to understand the present technology. Nevertheless, certain compounds such as 4-(4-dihexadecylsminostyryl)-N-methylpyridinium iodide (DIA); 1,3,5,7,8-pentamethyl-2,6,-di-t-butylpyrromethane-difluoreborate (PM-597); 4-(dicynaomethylene)-2-methyl-6-(4-dimethylamino styryl)-4H-pyran (DCM); eurobium(III) thenoyltrifluoroacetonate trihydrate (Eu(TTA)3.H2O); etc., when dissolved in a liquid crystal emit visible light upon exposure to UV radiation. The intensity and the wavelength of the emitted light depend on the orientation of the dye molecules with respect to liquid crystal phase. If the dye molecules are immobilized on a surface in a fixed orientation with respect to the surface and the liquid crystal undergoes a phase transition, the characteristics of the emitted radiation change. When an analyte interacts with the LC (e.g., directly or binds to a moiety such as receptor on the LC mesogens), the liquid crystal undergoes phase transition and the wavelength of the emitted light changes.

Accordingly, in some embodiments, a thin gold film is deposited on a substrate (e.g., a UV-transparent quartz substrate or a plastic film) using an electron beam evaporator. The gold surface is assembled into a liquid crystal assay device using small glass spacer rods as described above. The device is then filled with a liquid crystal. In some embodiments, the LC provides a reactive moiety. The present technology is not limited to any particular mechanism of action. Indeed, an understanding of the mechanism of action is not necessary to understand the present technology. Nevertheless, without exposure to the target analyte, the liquid crystal takes on one phase, for example, nematic. In some embodiments, the optical cell is irradiated with UV light, which in some embodiments is provided by a laser. In the absence of the analyte, the fluorescent molecules emit visible light at a wavelength that corresponds to the nematic phase of liquid crystals. When the device is exposed to an analyte the liquid crystal undergoes a phase transition to, for example, an isotropic phase. The shift in the peak position of the fluorescence spectrum (e.g., a change in the color of the emitted light) indicates a change in the dielectric environment of the fluorescent molecules. This change is caused by the phase transition of the LC induced by the analyte interacting with the mesogens or by binding of the analyte to a reactive moiety on the mesogen.

In other embodiments of the technology, fluorescent dye molecules such as Acridine Orange Base; Rhodamine 6G; perchlorate; 5-decyl-4,4-difluoro-4-bora-3a,4a-diaza-s-indacene-3-propionic acid; Nile Red; N,N'-Bis(2,5-di-tert-butylphenyl)-3,4,9,10-perylenedicarboximide; etc., are dissolved into the liquid crystal forming a guest-host system. The present technology is not limited to any particular mechanism of action. Indeed, an understanding of the mechanism of action is not necessary to understand the present technology. Nevertheless, the orientation of the dye molecule, in general, is dependent on the phase of the LC in the LC cell. When a beam of light (typically in the visible region) having a polarization parallel to the transition dipole moment of the dye, is passed through the guest host system, the incident light energy is absorbed by the dye molecule. The dye molecules then emit (e.g., visible) light at a different wavelength. However, if the incident light is polarized perpendicularly to the transition dipole moment of the dye molecule, it is not absorbed and the dye molecules do not emit any radiation. Therefore, in the absence of the target analyte, when the guest-host system is interrogated by a polarized light corresponding to the excitation wavelength of the dye used, the light emitted from the system is composed of the excitation wavelength. If the analyte is present in the ambient, it interacts with the LC or the functionalized surface and the liquid crystal undergoes phase transition, e.g., from the nematic to the isotropic phase. This causes a rotation of the transition moment of the dye molecule parallel to the polarization direction of the excitation beam. The dye molecules then absorb the incident wavelength and emit light at different wavelength. Thus, by probing a liquid crystal-dye mixture using polarized light propagating perpendicularly to the cell surface, the presence of the analyte in the environment can be probed. The liquid crystal assay device cell is fabricated as described above except that it is filled with a liquid crystal-dye mixture. For the interrogation, the polarization can be integrated on the liquid crystal cell or can be probed by sending polarized light.

In still further embodiments, the fluorescent properties of quantum dots are utilized for detecting analytes. The present technology is not limited to any particular mechanism of action. Indeed, an understanding of the mechanism of action is not necessary to understand the present technology. Nevertheless, some semiconductor quantum dots (e.g., with nanometer size) emit visible light when exposed to UV radiation. Due to quantum confinement, the electron-hole pairs trapped at the surface have a large band gap. Because of this large band gap, these semiconductor quantum dots absorb light in the UV region. The wavelength of light emitted by these fluorescence particles depends on their size and on properties of the surrounding medium, such as but not limited to, the dielectric constant of the surrounding medium. In some embodiments, these quantum dots are functionalized with a receptor targeted for the analyte so that a liquid crystal in contact with them assumes an orientation perpendicular to the surface of the quantum dots. Upon irradiation from a UV light source, the fluorescent spectrum shows a peak at a particular wavelength. When these dots are exposed to the analyte, the liquid crystal undergoes a phase transition, which causes a shift in the peak position.

The present technology is not limited to the use of any particular type of quantum dot. In some preferred embodiments, cadmium selenide quantum dots with thin zinc sulfide and polymer coatings are functionalized with a carboxylic acid terminated organic layer (for example 11-mercaptoundecanoic acid) and then treated to display a reactive moiety as described above (e.g., aniline-like groups). In some preferred embodiments, the quantum dots are dispersed in a liquid crystal (e.g., 5CB). The functionalized quantum dots influence the phase of the liquid crystals (nematic). In further preferred embodiments, a liquid crystal assay device is fabricated by forming a cavity (preferably 5 to 100 microns, most preferably about 25 microns) between two untreated UV transparent quartz substrates. The cavity between the substrates is filled with the mixture of functionalized quantum dots and liquid crystal. In still further preferred embodiments, the optical cell is exposed to an analyte (such as nitric oxide or nitrogen dioxide) and then probed with a UV light source, such as a laser. When the analyte binds to the receptors on the quantum dots, the liquid crystal undergoes a phase transition to isotropic, disrupting the quantum dots and thereby affecting the color of light emitted by them.

Electrical Detection

In some embodiments, a change in the physical properties of an LC is detected by measuring a change in the dielectric constant of the liquid crystals that results from an interaction of the analyte with the LC.

Sub-Responsive Exposure to Analyte

In some embodiments, devices are exposed to a "sub-responsive" amount of an analyte prior to its use to detect the analyte (e.g., prior to exposing the device to a sample comprising or suspected of comprising the analyte). In these embodiments, the device will demonstrate a response to a lower amount of analyte in a test sample than a device that has not been exposed to a sub-responsive amount of the analyte. As used herein, a "sub-responsive" amount, concentration, mass, etc. of an analyte is an amount, concentration, mass, etc. of the analyte that reacts with the device but that does not cause a detectable response (e.g., signal) from the device. Exposure to a sub-responsive amount of an analyte thus "pushes" or "primes" the device to demonstrate a response to a small amount of analyte.

IV Analytes

The methods and devices of the present technology can be used to detect a variety of analytes in the gas phase. The present technology is not limited to the detection of any particular type of analyte. Exemplary analytes include, but are not limited to, sulfur compounds, nitrogen compounds, thiols, alcohols, acids, oxides, alkanes, alkenes, alkynes, and phosphates.

The present technology finds use in the detection of variety of sulfur compounds. In some embodiments, the sulfur compounds are from a group that includes sulfides, disulfides, sulfites or sulfates, including but not limited to hydrogen sulfide, Chloromethyl trifluoromethyl sulfide, Ethylene sulfide, Dimethyl sulfide, Methyl Sulfide, Propylene sulfide, Trimethylene sulfide, 2-Chloroethyl methyl sulfide, 2-(Methylthio)ethanol, Ethyl methyl sulfide, Bis(methylthio)methane, 2-(Methylthio)ethylamine, N-Methyl-1-(methylthio)-2-nitroethenamine, Allyl methyl sulfide, 2-Chloroethyl ethyl sulfide, 3-(Methylthio)-1-propanol, 2,2'-Thiodiethanol, 2,2'-Dithiodiethanol, Diethyl sulfide, Methyl propyl disulfide, Tris(methylthio)methane, 2-(Ethylthio)ethylamine, 3-(Methylthio)propylamine, Cystamine dihydrochloride, 4-(Methylthio)-1-butanol, tert-Butyl methyl sulfide, Cyclohexene sulfide, Diallyl sulfide, Allyl disulfide, 3,3'-Thiodipropanol, 3,3'-Thiodipropanol, 3,6-Dithia-1,8-octanediol, Dipropyl sulfide, Isopropyl sulfide, Dipropyl disulfide, Isopropyl disulfide, 4-(Trifluoromethylthio)bromobenzene, 4-(Trifluoromethylthio)phenol, Phenyl trifluoromethyl sulfide, 3,5-Dichlorothioanisole, Chloromethyl 4-chlorophenyl sulfide, 4-(Trifluoromethylthio)aniline, 2-Bromothioanisole, 3-Bromothioanisole, 4-Bromothioanisole, 2-Chlorothioanisole, 3-Chlorothioanisole, 4-Chlorothioanisole, Chloromethyl phenyl sulfide, 2-Fluorothioanisole, 4-Fluorothioanisole, 4-Nitrothioanisole, Thioanisole, 2-(Methylthio)aniline, 3-(Methylthio)aniline, 4-(Methylthio)aniline, 2-(Methylthio)cyclohexanone, 3-(Methylthio)-1-hexanol, 4-(Trifluoromethylthio)benzyl bromide, 4-(Trifluoromethylthio)benzyl alcohol, Phenyl vinyl sulfide, 4-(Methylthio)benzyl bromide, 2-Chloroethyl phenyl sulfide, 4-(Methylthio)benzyl chloride, 2-Methoxythioanisole, 2-(Phenylthio)ethanol, 4-Methoxythioanisole, 4-(Methylthio)benzyl alcohol, Methoxymethyl phenyl sulfide, Ethyl phenyl sulfide, Methyl p-tolyl sulfide, Dibutyl sulfide, Dibutyl disulfide, Bis(trimethylsilylmethyl) sulfide, Phenyl propargyl sulfide, (4-Chlorophenylthio)acetone, Benzyl 2,2,2-trifluoroethyl sulfide, 4'-(Methylthio)acetophenone, Allyl phenyl sulfide, Cyclopropyl phenyl sulfide, 2-Nitro-5-(propylthio)aniline, S-Benzylcysteamine hydrochloride, Isoamyl sulfide, 4'-Methylthioisobutyrophenone, Pentafluorophenyl sulfide, Bithionol, Bis(3,5-dichlorophenyl) disulfide, Bis(3,5-dichlorophenyl) disulfide, Bis(4-chlorophenyl) disulfide, 3-Nitrophenyl disulfide, 4-Nitrophenyl disulfide, Bis (2-nitrophenyl) disulfide, 2-Nitrophenyl phenyl sulfide, 4-Nitrophenyl phenyl sulfide, 2-(4-Chlorophenylthio)aniline, 4-Amino-4'-nitrodiphenyl sulfide, 3,3'-Dihydroxydiphenyl disulfide, Diphenyl sulfide, Diphenyl disulfide, Phenyl disulfide, 2-(Phenylthio)aniline, 2,2'-Diaminophenylsulfide, 4,4'-Diaminodiphenyl sulfide, 2,2'-Dithiodianiline, Hexyl sulfide, Benzyl phenyl sulfide, Bis (phenylthio)methane, Dodecyl methyl sulfide, 2-Nitro-p- tolyl disulfide, Bis(4-methoxyphenyl) disulfide, Dibenzyl sulfide, Dibenzyl disulfide, p-Tolyl disulfide, Benzyl trisulfide, 2-[2-(Aminomethyl)phenylthio]benzyl alcohol, Phenylacetyl disulfide, Dioctyl sulfide, Chlorotriphenylmethyl disulfide, Tris(phenylthio)methane, Tris(phenylthio)methane, Dodecyl sulfide, Hexakis[(4-methylphenyl)thio]benzene, and Hexakis(benzylthio)benzene, Potassium methyl sulfate, Formaldehyde-sodium bisulfite adduct, Methyl sulfate sodium salt, Glyoxal bis(sodium hydrogen sulfite) adduct hydrate, Ethylene sulfite, Glyoxal sodium bisulfite addition compound hydrate, Dimethyl sulfite, Diethyl sulfite, Glutaraldehyde sodium bisulfite addition compound, Dipropyl sulfate, 4-Acetylphenyl sulfate potassium salt, Sodium 2-ethylhexyl sulfate, Sodium octyl sulfate, Dibutyl sulfate, 4-Hydroxy-3-methoxyphenylglycol sulfate potassium salt, Sodium dodecyl sulfate, Ammonium lauryl sulfate solution, Tetradecyl sulfate sodium salt, and Octadecyl sulfate sodium salt.

In some embodiments the sulfur compounds are from a group that includes triflates such as but limited to (Trimethylsilyl)methyl trifluoromethanesulfonate, (Trimethylsilyl) methyl trifluoromethanesulfonate, 4-Nitrophenyl trifluoromethanesulfonate, Phenyl trifluoromethanesulfonate, 1-Cyclohexenyl trifluoromethanesulfonate, Catechol bis(trifluoromethanesulfonate), p-Tolyl trifluoromethanesulfonate, 4-Acetylphenyl trifluoromethanesulfonate, 2,6-Dimethoxyphenyl trifluoromethanesulfonate, 3,5-Dimethoxyphenyl trifluoromethanesulfonate, 2-(Trimethylsilyl)phenyl trifluoromethanesulfonate, Di-tert-butylsilyl bis(trifluoromethanesulfonate), 1-Naphthyl trifluoromethanesulfonate, 2-Naphthyl trifluoromethanesulfonate, 4,4'-Biphenol bis(trifluoromethanesulfonate), 3,5-Di-tert-butylphenyl trifluoromethanesulfonate, 1,1'-Bi-2-naphthol bis(trifluoromethanesulfonate).

In some embodiments, the sulfur is in an oxidized state, including but not limited to sulfur dioxide, sulfur trioxide, sulfuric acid, sulfur oxide, Methyl phenyl sulfoxide, Phenyl vinyl sulfoxide, Methyl p-tolyl sulfoxide, Butyl sulfoxide, Methyl 2-phenylsulfinylacetate, Diphenyl sulfoxide, p-Tolyl sulfoxide, Dodecyl methyl sulfoxide, and Dibenzyl sulfoxide. In other embodiments, the sulfur is in a compound with halogenated elements, such as sulfenyl halides, sulfinyl halides, and sulfonyl halides including but not limited to Chlorocarbonylsulfenyl chloride, Methoxycarbonylsulfenyl chloride, 2,4-Dinitrobenzenesulfenyl chloride, 4-Nitrobenzenesulfenyl chloride, Trichloromethanesulfinyl chloride, tert-Butylsulfinyl chloride, 2,4,5-Trichlorobenzenesulfonyl chloride, 3,4-Dichlorobenzylsulfonyl chloride, 2-Chlorobenzylsulfonyl chloride, Trichloromethanesulfonyl chloride, Methanesulfonyl fluoride, Chlorosulfonylacetyl chloride, N,N-Dimethylsulfamoyl chloride, Cyclopropanesulfonyl chloride, 2-Propanesulfonyl chloride, Perfluoro-1-butanesulfonyl fluoride, 2-Bromo-4,6-difluorobenzenesulfonyl chloride, 2,3,4-Trichlorobenzenesulfonyl chloride, 2,5-Dibromobenzenesulfonyl chloride, Benzene-1,3-disulfonyl chloride, Cyclohexanesulfonyl chloride, m-Toluenesulfonyl chloride, disulfur dichloride, sulfur hexafluoride, thionyl chloride, and sulfuryl chloride.

In some embodiments, the gas compound contains nitrogen, including but not limited to nitrogen, ammonia, 1,3,5-Trinitrobenzene(TNB), Methyl nitrate, Nitroglycerin (NG), Triaminotrinitrobenzene (TATB), and Pentaerythritol tetranitrate (PETN). In some embodiments, the nitrogen containing compound is an amine. The amine may have an alkyl or an aryl functional group, may be aliphatic or aromatic in structure, may be represented by an organic compound that is a primary, secondary or tertiary amine including but not limited to methylamine, ethanolamine, trisamine, dimethylamine, methylethanolamine, aziridine, azetidine, pyrrolidine, piperidine, trimethylamine, dimethylethanolamine, aniline, cadaverine, idole, putrescine, and bis-tris methane.

In some embodiments, the gas compound is a thiol, including but not limited to methanethiol, ethanethiol, cysteine, 2-mercaptoethanol, dithiothreitol, and 2-mercaptoindole.

In some embodiments, the gas compound is an alcohol. The alcohol may be cyclic or acyclic, may be represented by an organic compound that is a primary, secondary or tertiary alcohol including but not limited to methanol, ethanol, isopropanol, tert-butyl alcohol, propanol, cyclopropanols, cyclobutanols, cyclopentanols, cyclopropanols, cyclohexanol, cycloheptanols, benzylic alcohols, diarylmethanols, and allylic alcohols.

In some embodiments, the gas compound is an acid. The acid may be organic or inorganic, monoprotic, diprotic or triprotic, including but not limited to acetic acid, sulfuric acid, hydrochloric acid, hypochlorous acid, chorous acid, chloric acid, perchloric acid, hydrobromic acid, hydroiodic acid, hydrofluoric acid, nitric acid, nitrous acid, carbonic acid, phosphoric acid, citric acid, formic acid, chromic acid, methanesulfonic acid, ethanesulfonic acid, benzenesulfonic acid, toluenesulfonic acid, folic acid, and salicylic acid.

In some embodiments, the gas compound is an oxide or its derivative, including but not limited to oxygen, nitric oxide, nitrous oxide, nitrogen dioxide, nitrogen dioxide, carbon monoxide, carbon dioxide, sulfur dioxide, ozone, and peroxides.

In some embodiments, the gas compounds are phosphates that may be organic or inorganic, including but not limited to ammonium phosphate, boranophosphate, diammonium phosphate, phosphagen, phosphate, phosphoric acid, phosphotungstic acid, polyphosphate, pyrophosphoric acid, and urea phosphate. In some embodiments, the organophosphates are those used as pesticides, including, but not limited to, Acephate (Orthene), Azinphos-ethyl, Azinphos-methyl (Guthion), Azinphos-methyl oxon, Bromophos-methyl, Carbophenothion (Trithion), Chlorfenvinphos (Supona), Chloropyrifos (Dursban/Lorsban), Chlorpyrifos-methyl, Chlorthiophos, Coumaphos (Co-Ral), Crotoxyphos (Ciodrin), Cyanophos, DEF (Butifos), Demeton (Systox), Demeton-Dialifor (Torok), Diazinon (O Analog), Diazinon (Spectracide), Dichlorvos-DDVP (Vapona), Dicrotophos (Bidrin), Dimethoate (Cygon), Dioxathion (Delnav), Disulfoton (Disyston), Disulfoton Sulfone, Edifenphos, EPN, Ethion (Nialate), Ethoprop (Mocap), Ethyl Parathion, Fenamiphos (Nemacur), Fenitrothion (Sumithion), Fensulfothion (Dasanit), Fenthion (Baytex), Fonofos (Dyfonate), Formothion, Heptenophos, Imidan (Phosmet), Isazophos (Triumph), Isofenphos (Amaze), Leptophos (Phosvel), Malaoxon, Malathion (Celthion), Merphos (Tribufos), Methamidophos (Monitor 4), Methidathion, Methyl Parathion (Metacide), Mevinphos (Phosdrin), Monocrotophos, Naled, Omethoate (Dimethoate O analog), Parathion (Alkron), Paroxon, Phorate (Thimet), Phorate-o, Phorate Sulfone, Phorate Sulfoxide, Phosalone, Phosphamidon (Dimecron), Piperophos, Pirimiphos-ethyl, Pirimiphos-methyl, Profenofos (Curacron), Propetamphos (Safrotin), Pyrazophos (Afgan), Quinalphos, Ronnel (Ectoral) (Fenchlorphos), Sulprofos (Bolstar), Terbufos (Counter), Tetrachlorvinphos (Gardona), Thionazin (Zinophos), and Triazophos (Hostathion). In some embodiments, the organophosphates are nerve agents (e.g., agents of war), including, but not limited to G agents (GD, soman; GB, sarin; and GA, tabun) and the V agents (VX).

In some embodiments, the analyte comprises an alkane (e.g., a paraffin), e.g., an alkane comprising between 4 and 12 carbon atoms per molecule (commonly referred to as C4-C12, e.g., butane, pentane, hexane, heptane, octane, nonane, decane, undecane, dodecane). In some embodiments, the analyte comprises an n-alkane and in some embodiments, the analytes comprises a branched alkane. In some embodiments, the analyte comprises a cycloalkane and/or a naphthene. In some embodiments, the analytes comprises an alkene (e.g., olefin), cycloalkene, isoalkane, aromatic (e.g., benzene, toluene, xylene, ethylbenzene, C3-benzene, C4-benzene), and/or an alkyne.

In some embodiments, the analyte comprises a mixture of organic compounds that is known by the general name of "gasoline", "petrol", "casing head gasoline", "motor fuel", or "motor spirit". Accordingly, in some embodiments, the analytes is or comprises an additive and/or blending agent such as an anti-knock agent, anti-oxidant, metal deactivator, lead scavenger, anti-rust agent, anti-icing agent, upper-cylinder lubricant, detergent, and/or a dye.

V Reactive Moieties

A wide variety of chemical sensors can be fabricated that will detect trace chemical vapors utilizing the interactions between liquid crystals and the analyte. The physical (e.g., optical and electrical) and the alignment properties of liquid crystal are governed by the intermolecular interactions of its functional moieties where a chemical change in the liquid crystal moiety is likely to alter its properties. Liquid crystal has the ability to influence the rates and energetics of organic reactions due to its integrated molecular arrangements. Incorporating a functional moiety that reacts with the target analyte can affect a change in liquid crystal molecules that will be translated into its observed properties.

The present technology provides a method for the detection or differentiation and quantitative measurement of a wide range of chemical vapors, such as oxides of nitrogen, ozone, amines, alcohols, thiols, etc. The liquid crystal can be tuned or functionalized by a combination of processes, such as, liquid crystals having reactive organic functional groups (—OH, —C=C—, —C≡C—, —N=N—, —NH2, —COOH, etc.), metal-ligand interaction, metal-liquid crystal interaction, metal-ligand-liquid crystal interaction. The choice of a particular liquid crystal composition will be based on the analyte that interacts with LC either by chemical reaction, metal-ligand coordination interaction, or dipole-dipole interactions (e.g., by changes in the polarity of the LC environment) that fulfills the requirements: (i) the target vapors should interact strongly with the LC, and (ii) this interaction must be coupled to a change in the LC.

The interaction between the analyte and the LC will be dependent on the analyte of interest and the active functional group present in the LC. This particular detection mechanism will involve acid-base, oxidation-reduction, substitution reaction, or combinations thereof at the functionalized moiety in the liquid crystal. The interaction of the target analytes with the liquid crystals will manifest as a change in the physical properties of liquid crystals (phase transition, optical birefringence, dielectric anisotropy, magnetic isotropy, or change in the orientation of liquid crystals on a surface) that can be detected using a variety of instruments capable of detecting these physical changes.

A variety of reactive moieties find use in the present technology. In some embodiments, the reactive moieties are functional groups available on the liquid crystal that is overlaid on a substrate. In some embodiments, a substrate is overlaid with a thin film of a solution to provide the reactive groups on the surfaces of the substrate.

VI Substrates

Substrates that find use in practicing the present technology can be made of practically any physicochemically stable material. In a preferred embodiment, the substrate material is non-reactive towards the constituents of the mesogenic layer. The substrates can be either rigid or flexible and can be either optically transparent or optically opaque. The substrates can be electrical insulators, conductors or semiconductors. Further, the substrates can be substantially impermeable to liquids, vapors and/or gases or, alternatively, the substrates can be permeable to one or more of these classes of materials. Exemplary substrate materials include, but are not limited to, inorganic crystals, inorganic glasses, organic glasses, inorganic oxides, metals, metal oxides, semiconductors, conductors, salts, organic polymers and combinations thereof. In some embodiments, the substrates have micropillared features thereon for the stabilization of the liquid crystal overlay and/or other reagents to the substrate surface or detection regions thereon.

Inorganic Crystal and Glasses

In some embodiments of the present technology, inorganic crystals and inorganic glasses are utilized as substrate materials (e.g., LiF, NaF, NaCl, KBr, KI, $CaF_2$, $MgF_2$, $HgF_2$, BN, $AsS_3$, ZnS, $Si_3N_4$, and the like). The crystals and glasses can be prepared by conventional techniques (see, e.g., Goodman., Crystal Growth Theory and Techniques, Plenum Press, New York 1974). Alternatively, the crystals can be purchased commercially (e.g., Fisher Scientific). The crystals can be the sole component of the substrate or they can be coated with one or more additional substrate components. Thus, it is within the scope of the present technology to utilize crystals coated with, for example, an organic polymer. Additionally, a crystal can constitute a portion of a substrate that contacts another portion of the substrate made of a different material, or a different physical form (e.g., a glass) of the same material. Other useful substrate configurations utilizing inorganic crystals and/or glasses will be apparent to those of skill in the art.

Inorganic Oxides

In other embodiments of the present technology, inorganic oxides are utilized as the substrate. Inorganic oxides of use in the present technology include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $In_2O_3$, $SO_2$, $PbO_2$, and the like. The inorganic oxides can be utilized in a variety of physical forms such as films, supported powders, glasses, crystals, and the like. A substrate can consist of a single inorganic oxide or a composite of more than one inorganic oxide. For example, a composite of inorganic oxides can have a layered structure (e.g., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal oxide metal, metal oxide-crystal).

In some embodiments, the substrate is a rigid structure that is impermeable to liquids and gases. In this embodiment, the substrate consists of a glass plate onto which a metal, such as gold, is layered by evaporative deposition. In a still further embodiment, the substrate is a glass plate ($SiO_2$) onto which a first metal layer such as titanium or gold has been layered. A layer of a second metal (e.g., gold) is then layered on top of the first metal layer (e.g., titanium).

Organic Polymers and Glasses

In still other embodiments of the present technology, organic polymers are utilized as substrate materials. Organic polymers useful as substrates in the present technology include polymers that are permeable to gases, liquids, and molecules in solution. Other useful polymers are those that are impermeable to one or more of these same classes of compounds. Many of these polymers can be prepared as glasses.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivatives (e.g., methyl cellulose, cellulose acetate, nitrocellulose), polysilanes, fluorinated polymers, epoxies, polyethers, and phenolic resins (see, Cognard (1982) "Alignment of Nematic Liquid Crystals and Their Mixtures" in *Mol. Cryst. Liq. Cryst.* 1: 174). Some organic polymers include polydimethylsiloxane, polyethylene, polyacrylonitrile, cellulosic materials, polycarbonates, and polyvinyl pyridinium.

In some embodiments, the substrate is permeable and it comprises a layer of gold, or gold over titanium, which is deposited on a polymeric membrane, or other material, that is permeable to liquids, vapors, and/or gases. The liquids and gases can be pure compounds (e.g., chloroform, carbon monoxide) or they can be compounds that are dispersed in other molecules (e.g., aqueous protein solutions, herbicides in air, alcoholic solutions of small organic molecules, etc.). Useful permeable membranes include, but are not limited to, flexible cellulosic materials (e.g., regenerated cellulose dialysis membranes), rigid cellulosic materials (e.g., cellulose ester dialysis membranes), rigid polyvinylidene fluoride membranes, polydimethylsiloxane, and track etched polycarbonate membranes.

In a further embodiment, a layer of gold on the permeable membrane is itself permeable. In some embodiments, the permeable gold layer has a thickness of about 70 Angstroms or less.

In those embodiments wherein the permeability of the substrate is not a concern and a layer of a metal film is used, the film can be as thick as is necessary for a particular application. For example, if the film is used as an electrode, the film can be thicker than in an embodiment in which it is necessary for the film to be transparent or semi-transparent to light.

Thus, in some embodiments, the film has a thickness from about 0.01 nanometer to about 1 micrometer, e.g., about 5 nanometers to about 100 nanometers. In some embodiments, the film has a thickness of from about 10 nanometers to about 50 nanometers.

Arrays

In some embodiments, the LC composition comprising reactive moieties is arrayed on the substrates using stamping, microcontact printing, or ink-jet printing. In still further embodiments, reactive moieties are spotted onto a suitable substrate. Such spotting can be done by hand with a capillary tube or a micropipette, or by an automated spotting apparatus such as those available from Affymetrix and Gilson (see, e.g., U.S. Pat. Nos. 5,601,980; 6,242,266; 6,040,193; and 5,700,637; each of which is incorporated herein by reference).

Micro-Structured Features

In some embodiments, the substrates utilized in the devices of the present technology comprise one more micro-structured features. In some embodiments, micro-structured features on the substrate augment the spreading of the liquid crystal composition. In still other embodiments, the micro-structured features stabilize the liquid crystal overlay and/or other reagents on the substrate surface or detection regions thereon. In a paper by Frisk et al (2006, *Lab on a Chip* 6: 1504), liquid was dispensed onto a micromachined biosensor substrate that was suspended vertically and remained stably dispersed (and immune to gravitational forces and shock) on that substrate. Following on this result, Sridharamurthy et al (2008, *Smart Mater Struct* 17) demonstrated that microstructures could be used to support a film of liquid crystal. In contrast to these systems, in some preferred embodiments, the micro-structured features are made my depositing a polymer on the substrate and etching away areas between the micro-structured features or made from the same material as the substrate. Additionally, in some embodiments, the analyte interacts and/or reacts with the LC composition rather than competing at the surface of the substrate.

Accordingly, in some embodiments, the micro-features pattern the surface and are selected from the group consisting of a grid, a channel, a plurality of pillars, or an array of assay areas, or combination thereof. In some embodiments, the micro-features are pillars that project from the surface of the substrates. In some embodiments, the substrates are comprised of glass, silicon, polymer, or a combination thereof. In still further embodiments, the pillars are comprised of the same material as the surface. In other embodiments, the pillars are comprised of a different material than the surface. In some embodiments, the substrate is glass while the pillars are made from a polymeric material. The pillars may comprise a shape selected from the group consisting of circular, triangular, square, hexagonal, or a combination thereof. The dimension of the pillars could be a variety of heights, widths, and spacings. Indeed, the pillar height may range from 1 micron to 50 microns, the width from 1 micron to 200 microns, and the spacing between pillars may range from 1 micron to 200 microns.

VII Mesogens

Any compound or mixture of compounds that forms a mesogenic layer can be used in conjunction with the present technology. The mesogens can form thermotropic, lyotropic, metallotropic, or cholesteric liquid crystals. The thermotropic, lyotropic, metallotropic, and cholesteric liquid crystals can exist in a number of forms including nematic, isotropic, chiral nematic, smectic, polar smectic, chiral smectic, frustrated phases, and discotic phases.

Some mesogens that find use in embodiments of the technology are displayed in Table 2. In some embodiments, the mesogen is 5CB (4-pentyl-4'-cyanobiphenyl), MLC-6812, MLC 12200, MBBA, EBBA, or 8CB (4-cyano-4'-octylbiphenyl), and combinations thereof.

The mesogenic layer can be a substantially pure compound, or it can contain other compounds, so called dopants, that enhance or alter characteristics of the mesogen. Thus, in some embodiments, the mesogenic layer further comprises a second compound, for example an alkane, which expands the temperature range over which the nematic and isotropic phases exist. Use of devices having mesogenic layers of this composition allows for detection of the analyte reactive moiety interaction over a greater temperature range.

In some embodiments, the mesogenic layer further comprises a dichroic dye or a fluorescent compound. Examples of dichroic dyes and fluorescent compounds useful in the present technology include, but are not limited to, azobenzene, BTBP, polyazo compounds, anthraquinone, perylene dyes, and the like. In some embodiments, a dichroic dye of a fluorescent compound is selected that complements the orientation dependence of the liquid crystal so that polarized light is not required for the assay. In some embodiments, if the absorbance of the liquid crystal is in the visible range, then phase changes can be observed using ambient light without crossed polarizers. In some embodiments, the dichroic dye or fluorescent compound is used in combination with a fluorimeter and changes in fluorescence are used to detect changes in phase transition of the liquid crystal.

TABLE 2

Molecular structures of mesogens suitable for use in embodiments of liquid crystal assay devices

| Mesogen | Structure |
|---|---|
| Anisaldazine | $CH_3-O-\phi-CH=N-N=CH-\phi-O-CH_3$ |
| NCB | $C_nH_{2n+1}-\phi-\phi-CN$ |
| CBOOA | $C_9H_{19}-O-\phi-N=CH-\phi-CN$ |
| Comp A | $C_7H_{15}-\text{(cyclohexyl)}-\phi-COO-\phi-NCS$ |
| Comp B | $C_8H_{17}-O-\phi-O-CO-\phi-O-CH_2-\phi-CN$ |
| $DB_7NO_2$ | $C_7H_{15}-\phi-O-CO-\phi-O-CO-\phi-NO_2$ |
| DOBAMBC | $C_{10}H_{21}-O-\phi-CH=N-\phi-CH=CH-COO-CH_2-CH(CH_3)(C_2H_5)$ |
| nOm<br>n = 1, m = 4: MBBA<br>n = 2, m = 4: EBBA | $C_nH_{2n+1}-O-\phi-CH=N-\phi-C_mH_{2m+1}$ |
| nOBA<br>n = 8: OOBA<br>n = 9: NOBA | $C_nH_{2n+1}-O-\phi-COOH$ |
| nmOBC | $C_nH_{2n+1}-O-CO-\phi-\phi-O-C_mH_{2m+1}$ |
| nOCB | $C_nH_{2n+1}-O-\phi-\phi-CN$ |
| nOSI | $C_nH_{2n+1}-O-\phi-\phi-COO-\phi-CH_2-CH(CH_3)(C_2H_5)$ |
| 98P | $C_3H_7-[CH_2(CH_3)]_5-O-\phi-\text{(pyrazine)}-C_8H_{17}$ |

TABLE 2-continued

Molecular structures of mesogens suitable for use in embodiments of liquid crystal assay devices

| Mesogen | Structure |
|---|---|
| PAA | 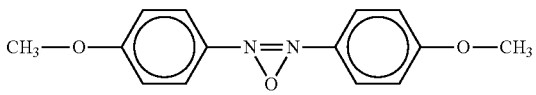 |
| PYP906 | 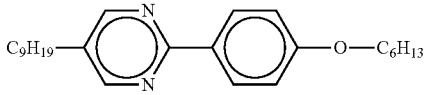 |
| nSm | 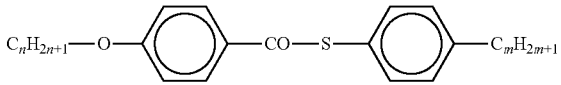 |

Although the disclosure herein refers to certain illustrated embodiments, it is to be understood that these embodiments are presented by way of example and not by way of limitation.

EXAMPLES

The following examples are provided to demonstrate and further illustrate certain embodiments and aspects of the present technology and are not to be construed as limiting the scope thereof.

In the experimental disclosure that follows, the following abbreviations are used: eq. (equivalents); M (molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); C (degrees Centigrade); U (units), mU (milliunits); min. (minutes); sec. (seconds).

Example 1

Comparison Between Microfluidic Cells and Sandwich Cells

During the development of embodiments of the technology provided herein, data were collected from testing traditional sandwich cells (LC cells where all the space between two surfaces was filled with LC), microfluidic cells with small discrete sensing areas (i.e. LC cells with a headspace between a substrate with discrete sensing areas and top surface) and microfluidic cells with large single sensing area (i.e. LC cells with a headspace between a substrate with large sensing areas and top surface). Some experiments were also performed with varying thicknesses of LC between the two sides of the sandwich cell and also varying thicknesses of the head space in microfluidic cells to access the effect of thickness in the response.

A traditional sandwich LC cell was prepared first by coating a 1"×3" aluminosilicate (AlSi) glass slide with 20 Å thick titanium layer followed by 100 Å thick gold film. The gold coated slides were chemically functionalized by forming self-assembled monolayer of 11-mercaptoundecanoic acid (MUA) after incubating the slide in 1 mM ethanolic solution for ~16 hrs. These slides were then rinsed thoroughly with ethanol and dried in a stream of nitrogen ($N_2$). The slides were then briefly (15 s) subjected to UV ozone treatment, then rinsed thoroughly with ethanol and dried in a stream of $N_2$. The slides were cut into three 1"×1" pieces and two pieces were spin coated with 1 ml of a 2 mM ethanolic solution of lead (II) perchlorate. The other piece was coated with 1 mM lead (II) perchlorate. After spin coating, the pieces were cut in half (1"×0.5") to provide substrates for three sandwich cells. The sandwich cells were fabricated by pairing a substrate with another identically treated substrate. To access the effect of thickness of the sandwich cell, one 25 micron and one 50 micron thick cell were fabricated from 2 mM coated substrate while one 25 micron cell was fabricated from 1 mM coated substrate. Two substrates, with the functionalized surfaces facing each other, were separated by mylar spacers with desired thickness (e.g. 25 or 15 micron) by placing one long mylar piece along one of the short ends and two small pieces at two corners of the other short end. The two pieces were held together by using binder clips. Each sandwich cell was filled with 10 μl of LC E7, by capillary action through space between the small mylar pieces.

Microfluidic cell with large single sensing area "(long sensor)" was also prepared using 3.8 cm×1.9 cm glass substrate coated with polymer micropillars fabricated using standard photolithography. The polymer micropillars were 5 micron tall, 10 micron diameter with 20 micron center-to-center spacing and covered 3.5 cm×1.3 cm area on the glass substrate. The micropillared glass substrate was coated with 20 Å thick titanium layer followed by 100 Å thick gold film. The gold coated substrates were chemically functionalized by forming self-assembled monolayer of 11-mercaptoundecanoic acid (MUA) after incubating the substrate in 1 mM ethanolic solution for ~16 hrs. These substrates were then rinsed thoroughly with ethanol and dried in a stream of $N_2$. The substrates were then briefly (15 s) subjected to UV ozone treatment, then rinsed thoroughly with ethanol and dried in a stream of $N_2$. The microstructured substrate was then spin coated with 1 mL of 2 mM ethanolic solution of lead(II) perchlorate and spotted with 4 μl of a 20/30.3 mixture of E7 and octane. The resultant substrate was paired with OTS treated substrates forming a head space above the LC film using 12 micron (sensor 1), 15 micron (Sensor 2) top, 25 micron (sensor 3), and 50 micron (Sensor 4) thick mylar strips.

Microfluidic cells with 10 discrete sensing areas in 2 rows "2×5 sensors" were fabricated by using a 2×5 array of micropillared area (~5 mm across) spaced ~8.5 mm (center-to-center) apart on an ~43 mm×17 mm glass substrates. The polymer micro pillars on the glass substrate were fabricated using standard wet photolithography and were 5 micron tall, 10 micron diameter and are spaced by 20 micron (center-to-center). The micropillared substrates were coated with 20 Å thick titanium layer followed by 100 Å gold film. The gold coated slides were chemically functionalized by forming self assembled monolayer of 11-mercaptoundecanoic acid (MUA) after incubating the substrate in 1 mM ethanolic solution for ~16 hrs. These substrates were then rinsed thoroughly with ethanol and dried in a stream of nitrogen ($N_2$). The slides were then briefly (15 s) subjected to UV ozone treatment, then rinsed thoroughly with ethanol and dried in a stream of $N_2$. The substrate was then spin coated with 2 mM lead(II) perchlorate. The micropillared areas (5 mm across) were then spotted two times with 0.14 µl of an E7-octane mixture (25%-75%). The LC filled sensor substrate was then paired with another glass substrate coated with (Tridecafluoro-1,1,2,2-tetrahydrooctyl)-trichlorosilane (OTS) with the functionalized surfaces facing each other. Two mylar strips (12 micron thick) were placed along the long edge of the substrate to define the head space above the LC film and the substrates were held together using binder clips. In a second 2×5 sensor, another mylar strip was placed along the middle to form a "channel" separating the descrete circular areas.

Figure 1B:
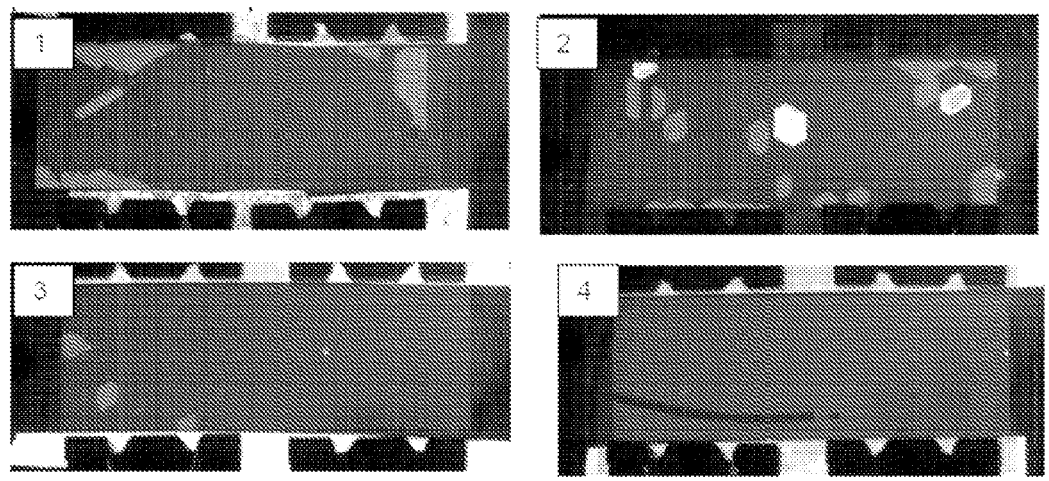
Figure 1C:
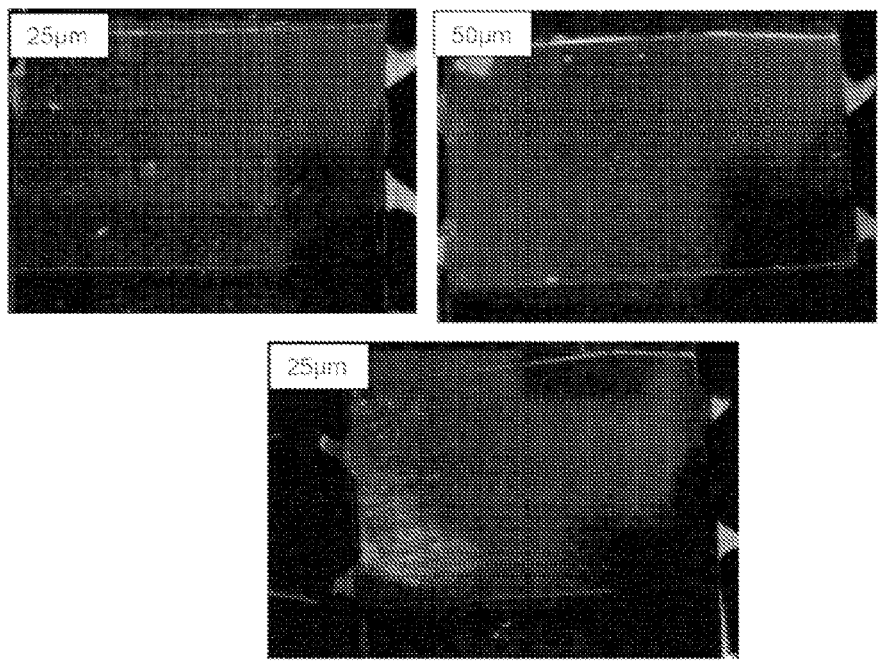

The 2×5 sensor, sandwich cells, and long sensors were stored in the argon filled bag at 4° C. and exposed the following day to 1 ppm $H_2S$. Prior to opening the bag, all the cells were allowed to equilibrate to room temperature for 30 minutes. After equilibration, images of 2×5 sensors (FIG. 1 A), long sensors (FIG. 1 B), and sandwich cells (FIG. 1 C) were taken before exposure to 1 ppm $H_2S$ for eight hours (FIG. 1). The $H_2S$ test chamber (21 Lit volume) was equilibrated to 1 ppm $H_2S$ at a flow rate of 4 L/min. for 15 minutes, then the sensors were placed inside, and the test chamber was equilibrated for an additional 15 minutes at the same flow rate. The flow was then decreased to 1 L/min. and all sensors were exposed at this rate for the remainder of 8 hours.

Figure 2A:
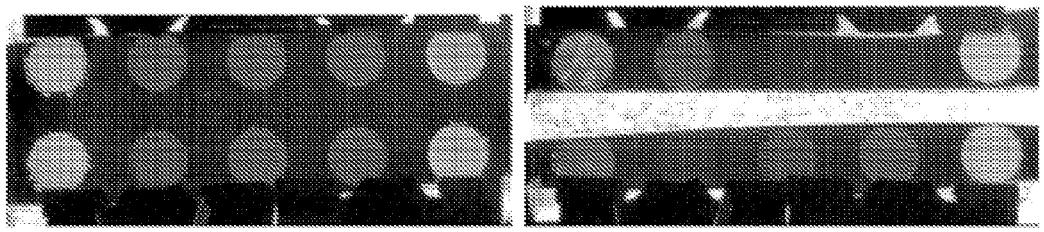
FIG. 2 shows images of 2×5 sensors after exposure to 1 ppm $H_2S$ (FIG. 2A), long sensors #1 to #4 after exposure to 1 ppm $H_2S$ (FIG. 2B), and sandwich cells comprising mylar of 25 microns and 50 microns after exposure to 1 ppm $H_2S$ (FIG. 2C).
Figure 2B:
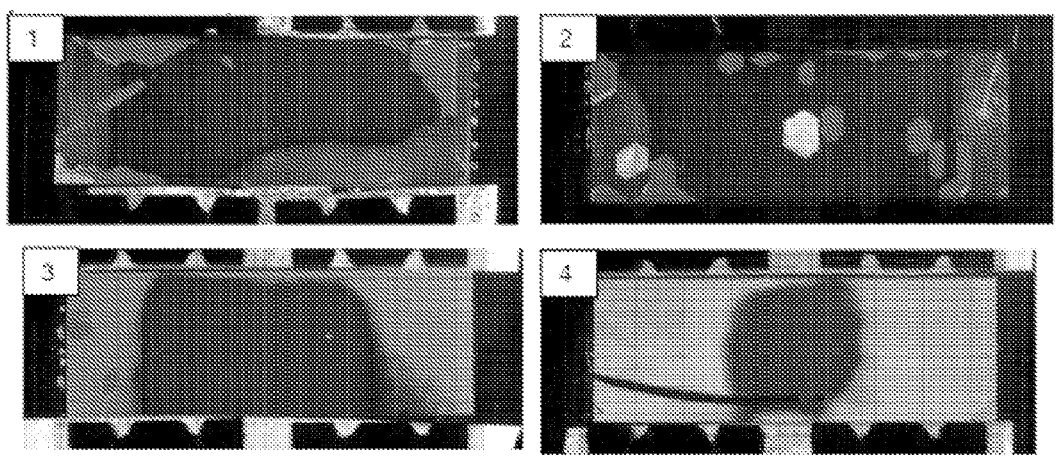
Figure 2C:
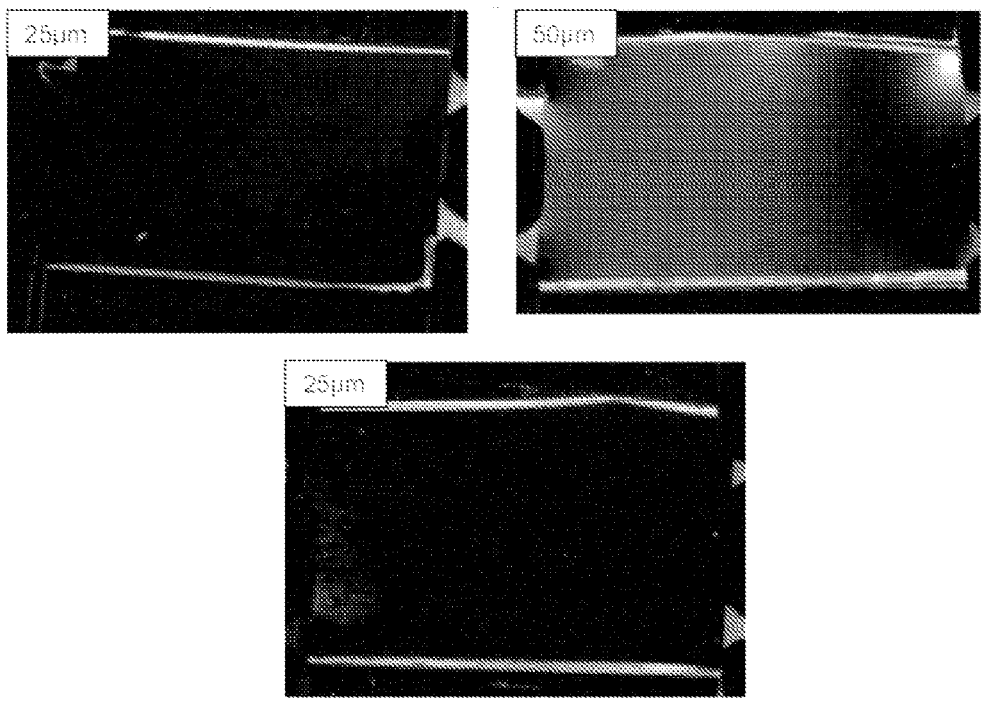
Figure 3:
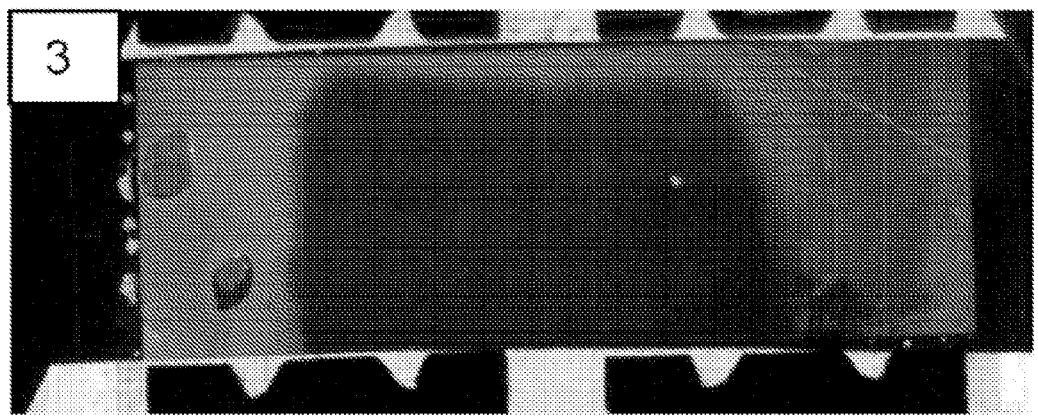
FIG. 3 shows an image of the long sensor #3 from FIGS. 1 and 2 after storage at ambient conditions for several days after exposure.

After exposure to 1 ppm $H_2S$ for eight hours images were acquired (FIG. 2). The 2×5 sensors show responses on the first circles on both sides and the response is not affected by the presence of an additional piece of mylar in the center of the cell (FIG. 2A). The long sensors demonstrated a good response, especially with 25 micron and 50 micron mylar (FIG. 2B). Thicker mylar produced brighter reacted areas and greater responses. The sandwich cells also gave a very small responses (FIG. 2C).

Long Sensor 3 was imaged 2 to 3 days after exposure to $H_2S$ and the image of the sensor was acquired. The appearance of the sensor was compared with that on the first day. The response of the sensor was stable (FIG. 2, compare with FIG. 2B, Sensor 3).

The results from this experiment show that (i) the microfluidic cells (long sensor or 2×5 sensor) with head space are more sensitive than the traditional sandwich cells fabricated from identically prepared substrate (ii) the 15 micron spacers provide for a small response and thicker spacers (e.g., 25 micron mylar) provide a greater response and (iii) relatively long cells (similar to 2×5 sensors) are appropriate for higher concentrations of $H_2S$.

Example 2

Comparison Between Sensitivity of Sandwich Cells and Microfluidic Cells

During the development of embodiments of the technology, experiments were conducted to develop new embodiments of liquid cells to detect an analyte (e.g., HO. For example, in some experiments, traditional sandwich cells (cells with all the space between two substrate filled with LC) were constructed and their performance to detect $H_2S$ was compared with microfluidic cells (cells with a head space between the top surface and LC film) fabricated using identical protocol.

A traditional sandwich LC cell was prepared first by coating a 1"×3" aluminosilicate (AlSi) glass slide with 20 Å thick titanium layer followed by 100 Å thick gold film. The gold coated slides were chemically functionalized by forming self-assembled monolayer of 11-mercaptoundecanoic acid (MUA) after incubating the slide in 1 mM ethanolic solution for ~16 hrs. These slides were then rinsed thoroughly with ethanol and dried in a stream of nitrogen ($N_2$). The slides were then briefly subjected (15 s) to UV ozone treatment, then rinsed thoroughly with ethanol and dried in a stream of $N_2$. The slides were cut into three 1"×1" pieces and each piece was spin coated with 1 ml of a 4 mM ethanolic solution of lead perchlorate. After spin coating, the pieces were cut in half (1"×0.5") to provide substrates for six sandwich cells. The sandwich cells were fabricated by pairing these substrates with (Tridecafluoro-1,1,2,2-tetrahydrooctyl)-trichlorosilane (OTS) treated glass substrates with similar dimensions. Two substrates, with the functionalized surfaces facing each other, were separated by mylar spacers with desired thickness (e.g. 25 micron) by placing one long mylar piece along one of the short ends and two small pieces at two corners of the other short end. The two pieces were held together by using binder clips. Each sandwich cell was filled with 10 µl of LC E7, by capillary action through space between the small mylar pieces.

A microfluidic cell was prepared using 3.8 cm×1.9 cm glass substrate coated with polymer micropillars fabricated using standard photolithography. The polymer micropillars were 5 micron tall, 10 micron diameter with 20 micron center-to-center spacing and covered 3.5 cm×1.3 cm area on the glass substrate. The micropillared glass substrate was coated with 20 Å thick titanium layer followed by 100 Å thick gold film. The gold coated substrates were chemically functionalized by forming self-assembled monolayer of 11-mercaptoundecanoic acid (MUA) after incubating the substrate in 1 mM ethanolic solution for ~16 hrs. These substrates were then rinsed thoroughly with ethanol and dried in a stream of $N_2$. The substrates were then briefly (15 s) subjected to UV ozone treatment, then rinsed thoroughly with ethanol and dried in a stream of $N_2$. The microstructured substrate was then spin coated with 1 mL of 1 mL ethanolic solution of lead(II) perchlorate. The micropillared area of the substrate was then filled with ~3 microliter of LC E7: octane (40:60) mixture. After evaporation of the organic solvent, the LC-filled substrate was then paired with an OTS treated glass substrate forming a head-space (e.g., a head space of approximately 20 microns), by placing two strips along the long side of the substrate, to allow controlled diffusion of the targeted analytes above the LC film.

Once these sandwich cells were fabricated, the LC did not exhibit homeotropic alignment on these substrates while the microfluidic cells exhibited homeotropic alignment as expected on lead (II) perchlorate treated substrates. These results suggested that a format using a micropillared substrate may provide a better alignment of the LC on an identically functionalized surface for analyte detection. As a result, experiments were conducted to compare performance of microfluidic cell with headspace and sandwich cell fabricated using slightly different preparation protocols. The sandwich cells were fabricated as described above except the MUA functionalized surfaces were not treated with UV ozone as described above while the microfluidic cells were fabricated as described above. This process produced sandwich cells with good initial LC alignment.

Experiments were performed by manufacturing six sandwich cells and exposing them alongside six microfluidic cells (e.g., prepared as described above) to compare responses. The sensors were manufactured and stored at 4° C. until the experiment was performed. Two microfluidic cells and two sandwich cells were assigned to be exposed to air at 45% RH (negative controls) and an additional four microfluidic cells and four sandwich cells were assigned to be exposed to 8 ppm $H_2S$ at 45% RH for eight hours.

Figure 4A:
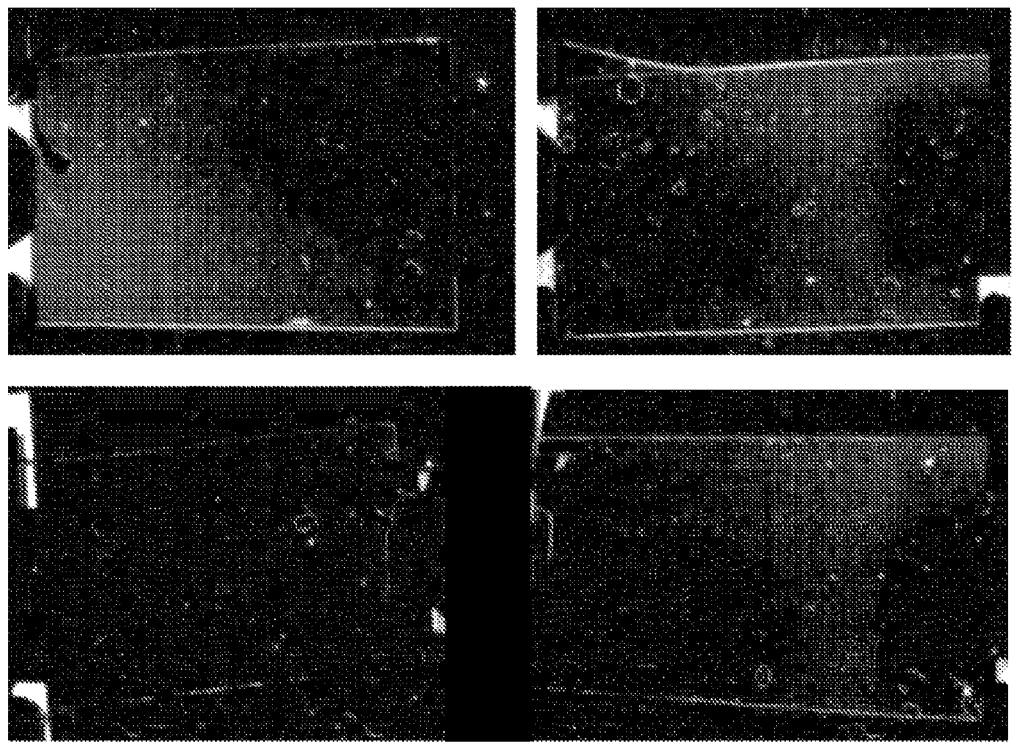
FIG. 4 shows sandwich cells prior to exposure to analyte (FIG. 4A) or a zero air control (FIG. 4B).
Figure 4B:
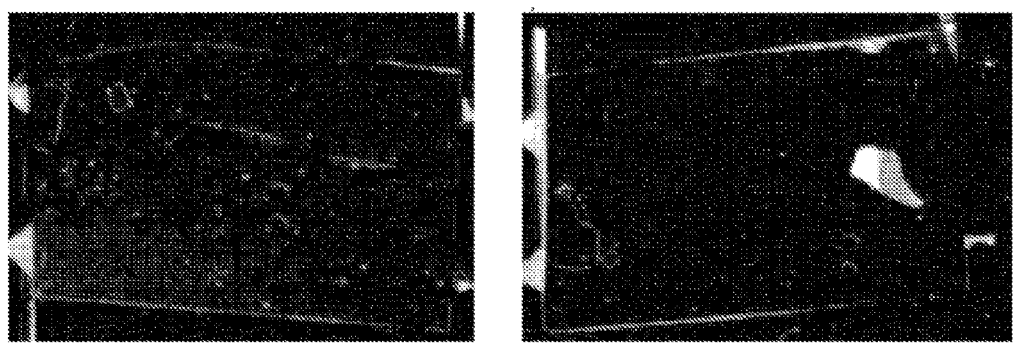
Figure 5A:
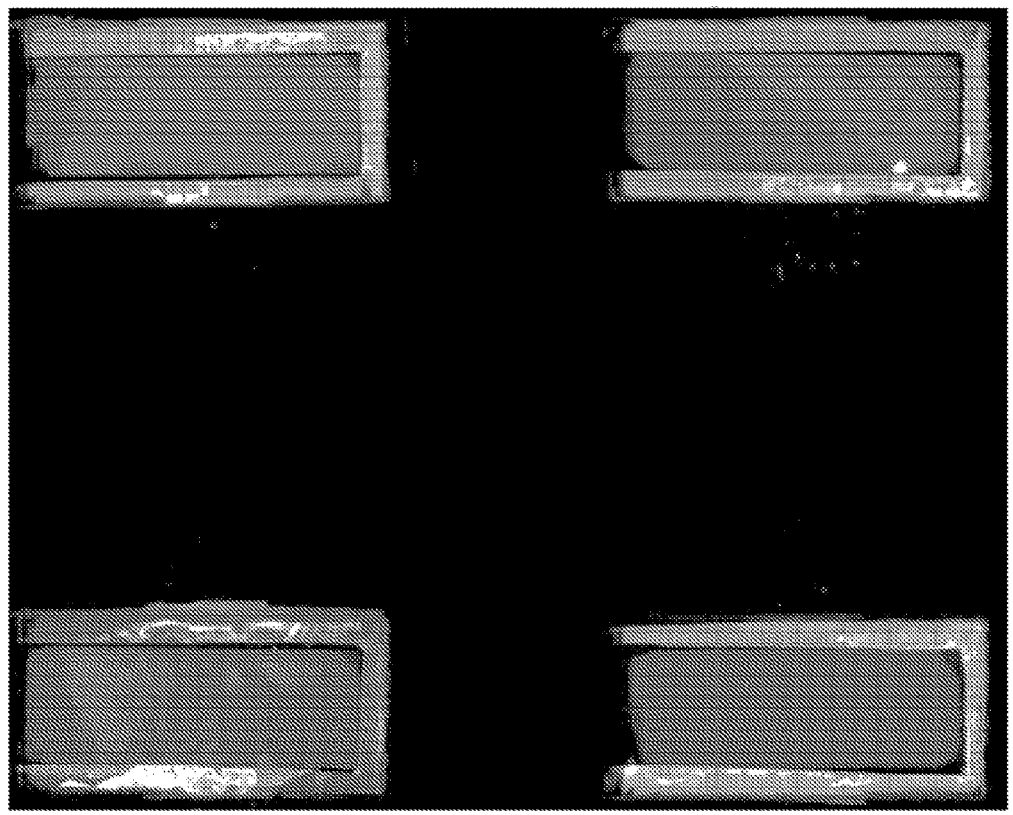
FIG. 5 shows images of microfluidic cells prior to exposure to analyte (FIG. 5A) or a zero air control (FIG. 5B).
Figure 5B:

On the day of the exposure, microfluidic cells and sandwich cells were allowed to equilibrate at room temperature for 15 minutes before opening the bags. Images were taken before the microfluidic and sandwich cells were exposed to $H_2S$ and of sensors assigned as negative (i.e. exposed to 45% zero air) controls (FIG. 4 and FIG. 5). Before exposure, the sandwich cells appeared homeotropic with the exception of one bright spot in one of the cells assigned as negative control cells (FIG. 4) and one of the microfluidic cells (FIG. 5). They were then placed in a large (~21 L) test chamber and the $H_2S$ flow inside the chamber was maintained at 5.8 liter/min for initial 15 minutes. After the cells had been in the test chamber for 15 minutes at a 5.8 liter/minute flow rate, the flow rate was decreased to 1.2 liter/minute for the remainder of the eight-hour exposure.

Figure 6A:
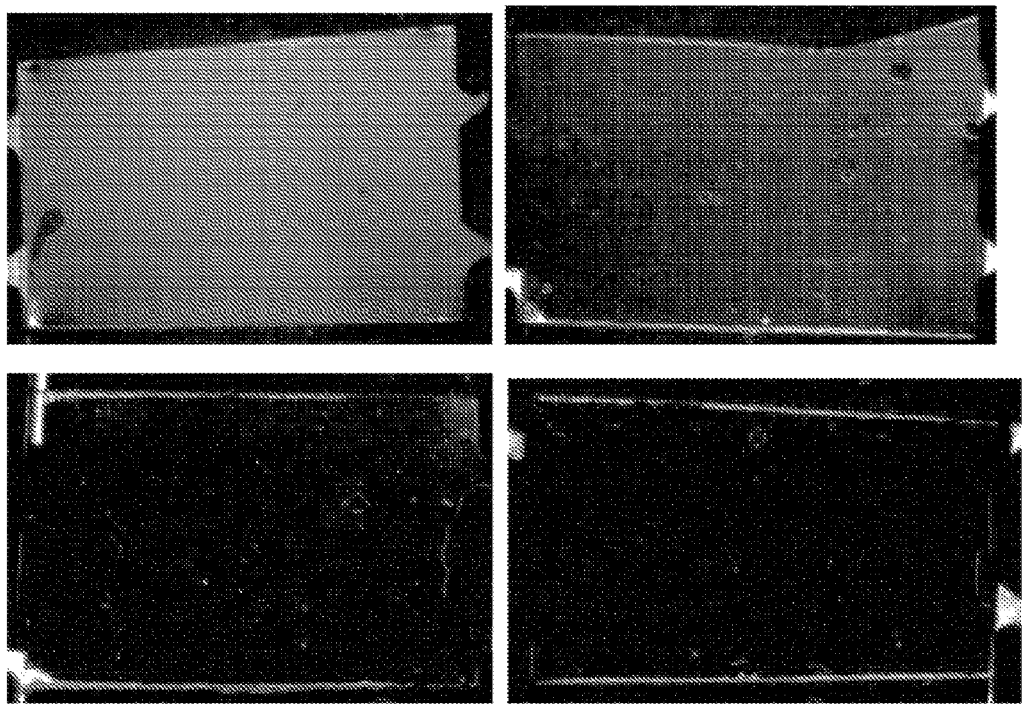
FIG. 6 shows images of sandwich cells after exposure to 8 ppm $H_2S$/45% relative humidity for eight hours (FIG. 6A) and to zero air control at 45% relative humidity for eight hours (FIG. 6B).
Figure 6B:
Figure 7A:
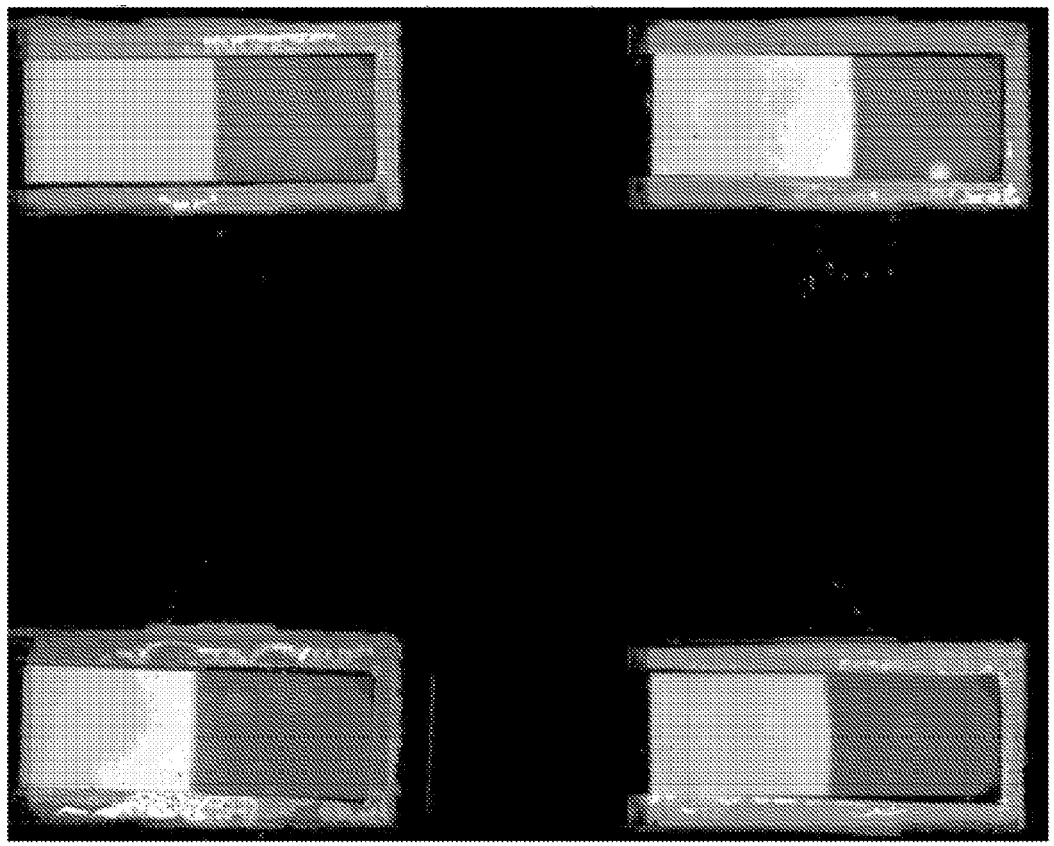
FIG. 7 shows images of microfluidic cells after exposure to 8 ppm $H_2S$/45% relative humidity for eight hours (FIG. 7A) and to zero air control at 45% relative humidity for eight hours (FIG. 7B).
Figure 7B:
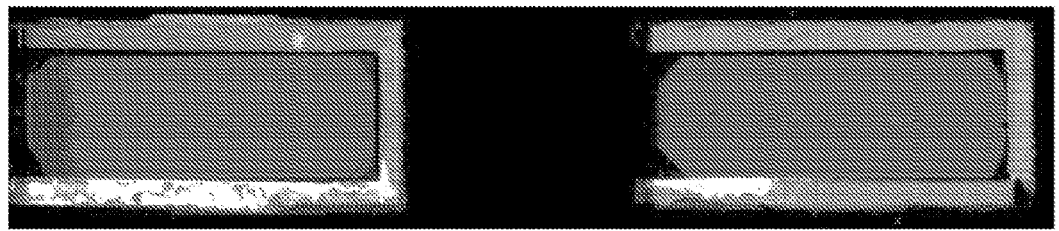

All of the microfluidic cells and sandwich cells were exposed together to either $H_2S$ or zero air (FIG. 6 and FIG. 7). There are small responses that can be seen along the edge of the sandwich cells. The responses are barely visible after the eight hour exposure (FIG. 6 A). The sandwich cells exposed to zero air show no responses after the eight hour exposure (FIG. 6 B). The microfluidic cells show responses of birefringent fronts ranging from 17.4 to 20.4 mm (FIG. 7 A). The microfluidic cells that were exposed to zero air show no responses after the eight hour exposure (FIG. 7B). Neither the microfluidic nor the sandwich cells showed any response to zero air at 45% RH.

These results establish that the microfluidic cells (i) provide more stable alignment of LC on similarly functionalized surface and (ii) are more sensitive to the target analyte ($H_2S$) compared to traditional sandwich cells.

Example 3

Microfluidic Cell as a Cumulative Dosimeter

During the development of embodiments of the technology provided herein, experiments were conducted to establish that the microfluidic cells could be used as cumulative dosimeter by determining the relationship between response from these microfluidic cells "(cumulative sensors)" and analyte dose. Experiments were conducted using a cumulative analyte sensor in an average environmental condition of 22° C. and 45% relative humidity (RH).

Cumulative Sensor Fabrication

Cumulative sensors were designed to measure a total dose of gaseous $H_2S$ in a sample by integrating over the concentration and exposure time. Cumulative sensors were prepared using 3.8 cm×1.9 cm glass substrates coated with polymer micropillars fabricated using standard photolithography. The polymer micropillars were 5 micron tall, 10 micron diameter with 20 micron center-to-center spacing and covered 3.5 cm×1.3 cm area on the glass substrate. The micropillared glass substrate was coated with a 20 Å thick titanium layer followed by a 100 Å thick gold film. The gold coated substrates were chemically functionalized by forming a self-assembled monolayer of 11-mercaptoundecanoic acid (MUA) after incubating the substrate in 1 mM ethanolic solution for ~16 hrs. These substrates were then rinsed thoroughly with ethanol and dried in a stream of $N_2$. The substrates were then briefly (15 s) subjected to UV ozone treatment, then rinsed thoroughly with ethanol and dried in a stream of $N_2$. The microstructured substrate was then spin coated with 1 mL of ethanolic solution of lead(II) perchlorate. The micropillared area of the substrate was then filled with ~3 microliter of LC E7:octane mixture at 40:60 ratio. After evaporation of the organic solvent, the LC-filled substrate was then paired with an OTS treated glass substrate forming a head-space (e.g., a head space of approximately 20 microns) by placing a U-shaped mylar strip around edge of the substrate, to allow controlled diffusion of the targeted analytes above the LC film. The substrates were held together using binder clips and three sides with the mylar strips were sealed using low off-gassing epoxy to force the gas diffusion through the open end of the sensor. These cumulative sensors, fabricated in a lot of five, were stored in an argon environment prior to use.

Cumulative sensors were exposed inside a large (21 liter) exposure chamber to 8 combinations of $H_2S$ concentration and time at 22° C. and 45% RH to determine the relationship between sensor response and $H_2S$ dose (concentration× time). Sensors were also exposed to $H_2S$ free air at 22° C. and 45% RH as a control. Four sensors were tested per dose. An in-house gas delivery and testing apparatus that is capable to generate $H_2S$ concentrations from low ppb to 100 ppm was used to test the sensors. The exposure system also allows generation of desired concentrations at desired temperatures and humidity. For each test point 5 sensors were made as described above; 1 sensor was exposed to 16 ppm-hours at room temperature and 45% RH as a reference exposure for quality control and the other 4 sensors were exposed to the test dose.

Additional experiments tested a microfluidic cell for measuring $H_2S$ that was prepared as described in Example 1.

Quality Verification and Test Procedure

On the day of exposure, the package of five sensors was first allowed to equilibrate at room temperature for 15 minutes. After equilibration, one sensor was used as a QC sensor. For each lot, a QC sensor was exposed to 8 ppm $H_2S$ at 45% RH for 2 hours (nominal dose of 16 ppm-hr). The $H_2S$ test chamber (21 liter volume) was equilibrated at a flow rate of 5.8 L/minutes for 15 minutes before exposure; the sensor was imaged, and then placed inside the test chamber. The test chambers were equilibrated for an additional 15 minutes at the 5.8 liter/minute flow rate. The flow was then decreased to 1.2 liter/minute and the sensor was exposed at this rate for the remainder of the 2 hours and 5 minutes. The sensor was again imaged after exposure. Then the sensor was left at ambient temperature for 6 hours and imaged again to check for any change in response. In parallel, the remaining four sensors were exposed to the desired test concentrations for specified time inside another identical exposure chamber following similar procedure.

Measurement of Response

After exposure to the QC dose or the desired dose, digital images of the sensors were acquired using a digital scanner interfaced with a laptop. During the development of embodiments of the technology provided herein, several different methods were evaluated for determining sensor response to analyte by analyzing images of exposed sensors. While the technology is not limited in the methods that are appropriate for quantification of images, ImageJ (NIH) was used in some trials for analyzing sensor images acquired from a scanner. Using the ImageJ freeware, a simple method to calculate the width of the bright front (i.e. the distance the bright front has traveled in an otherwise dark background) was developed. Using this method, the response length was measured for both the QC sensor and the sensors exposed to different doses.

Results

Figure 8A:
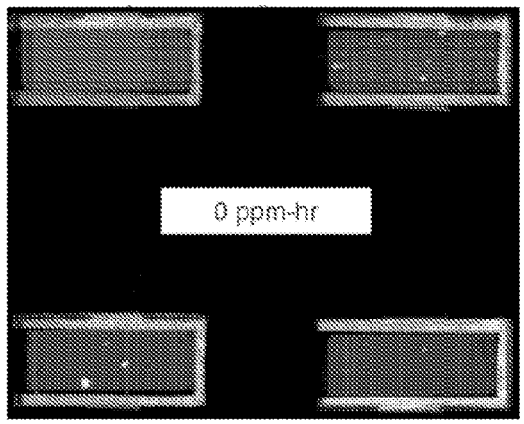
FIG. 8A shows a sensor exposed to $H_2S$ for 0 ppm-hour.
Figure 8B:
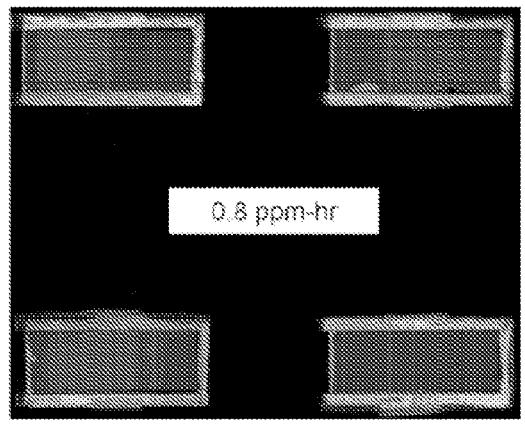
FIG. 8B shows a sensor exposed to $H_2S$ for 0.8 ppm-hour.
Figure 8C:
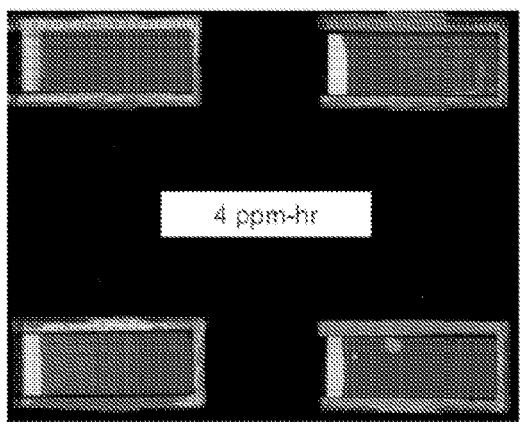
FIG. 8C shows a sensor exposed to $H_2S$ for 4 ppm-hour.
Figure 8D:
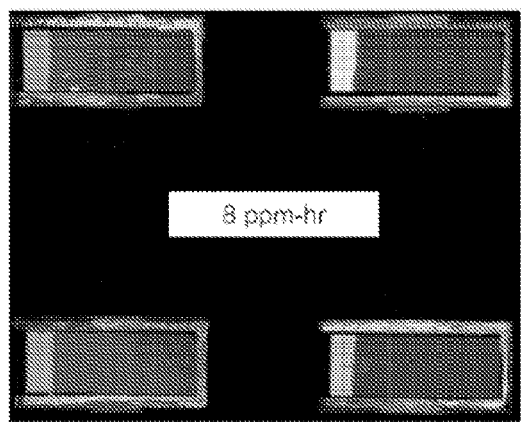
FIG. 8D shows a sensor exposed to $H_2S$ for 8 ppm-hour.
Figure 8E:
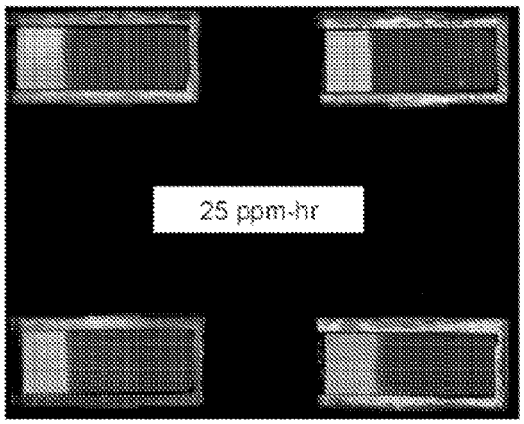
FIG. 8E shows a sensor exposed to $H_2S$ for 25 ppm-hour.
Figure 8F:
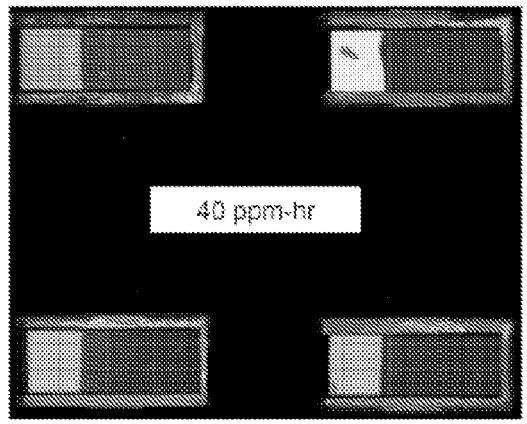
FIG. 8F shows a sensor exposed to $H_2S$ for 40 ppm-hour.
Figure 8G:
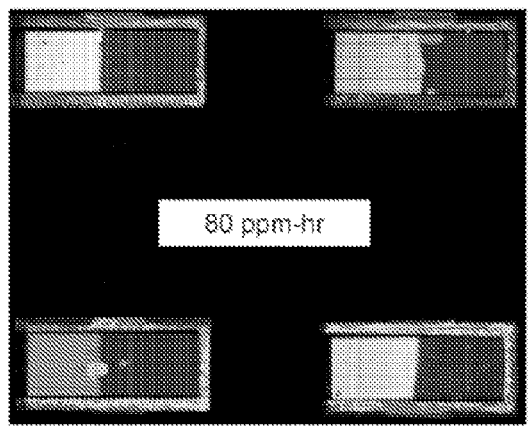
FIG. 8G shows a sensor exposed to $H_2S$ for 80 ppm-hour.
Figure 8H:
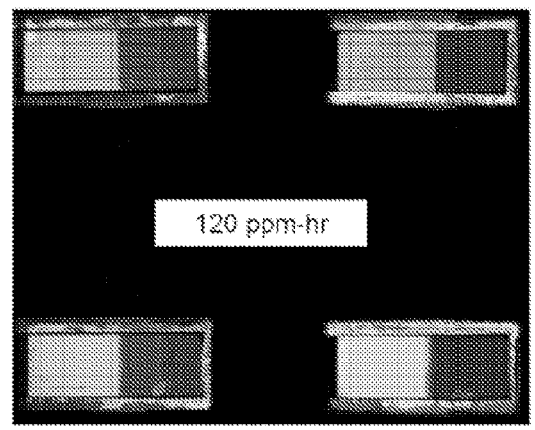
FIG. 8H shows a sensor exposed to $H_2S$ for 120 ppm-hour.
Figure 8I:
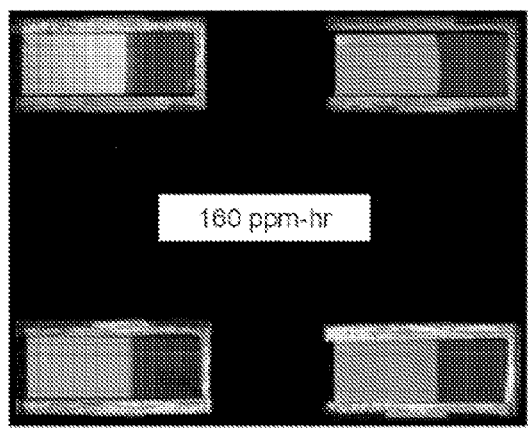
FIG. 8I shows a sensor exposed to $H_2S$ for 160 ppm-hour.
Figure 8J:
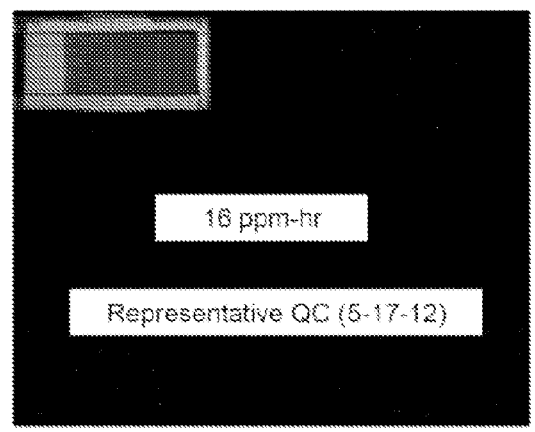
FIG. 8J shows a sensor exposed to $H_2S$ for 16 ppm-hour verify quality control.

Images acquired of sensors exposed to 0, 0.8, 4, 8, 25, 40, 80, 120, and 160 ppm-hours of $H_2S$ are provided in FIG. 8A through 8I. FIG. 8J shows an image acquired for the quality control experiment in which a sensor was exposed to 16 ppm-hours of $H_2S$.

Figure 9:
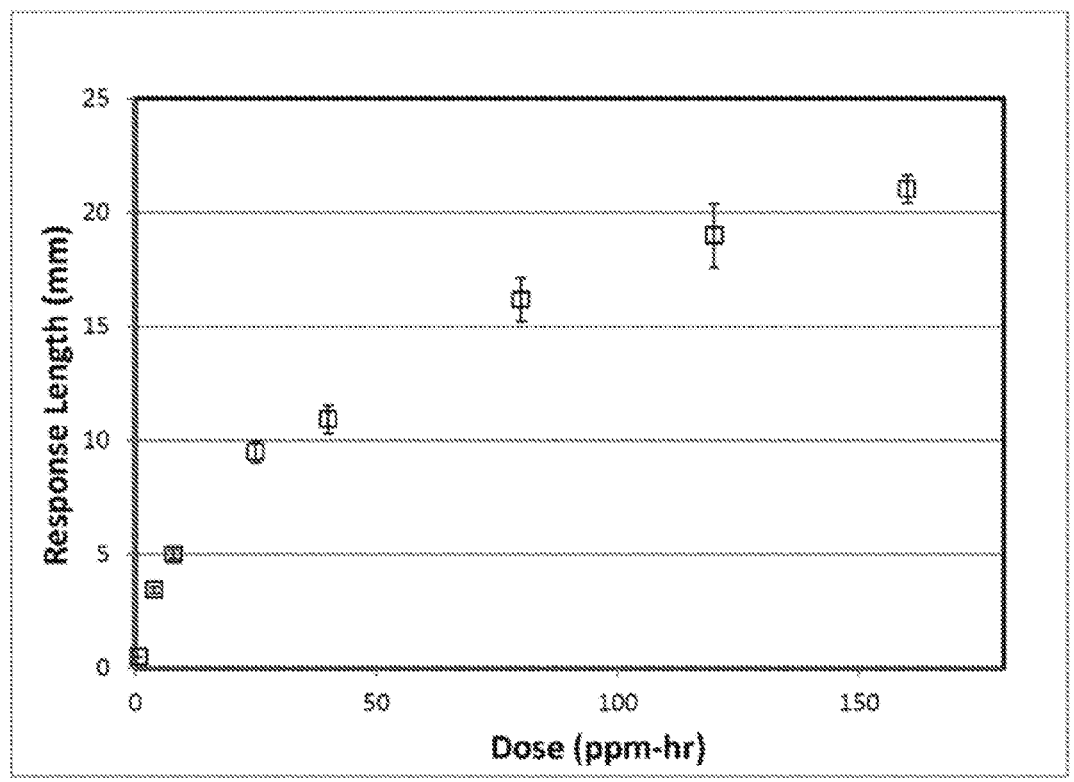
FIG. 9 is a plot showing the length of the response front versus $H_2S$ exposure dose for an $H_2S$ sensor.
Figure 10:
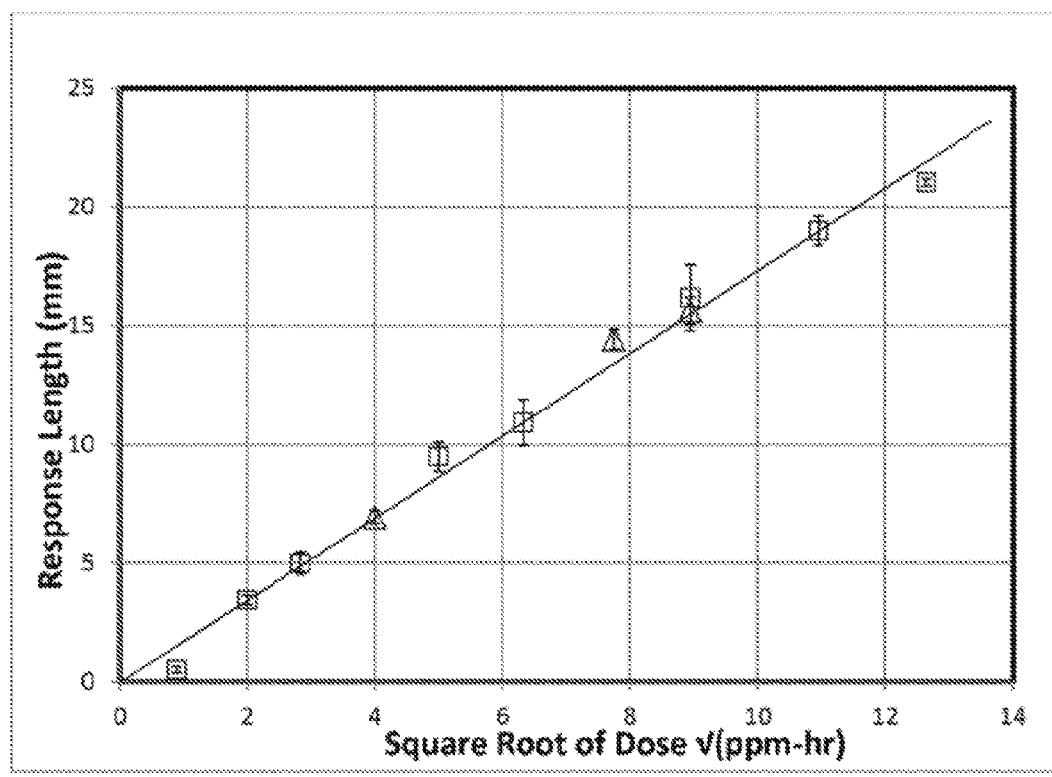
FIG. 10 is a plot showing the length of the response front versus the square root of the $H_2S$ exposure dose for an $H_2S$ sensor.

The average widths of the response fronts were determined using ImageJ and are plotted in FIG. 9. The consistent curve demonstrates that the sensors do provide a response to total $H_2S$ dose and are not skewed by shifting time and concentration combinations. The relationship between response length and dose resembles a square root curve. Plotting response length versus the square root of dose produces a linear relationship (FIG. 10). Without being bound by theory, the square root relationship most likely results from this being a process governed by laws of diffusion of gas.

After the dose response curve was generated, a verification test was performed by making four lots of sensors following the same protocol and exposing them to different concentrations. FIG. 10 shows that response from the 3 verification runs (denoted by triangles) were on the same line and performed very closely to expected performance.

By fitting a plot of the square root of the dose versus response length, an equation was derived to correlate the measured dose from the response length of a sensor:

Furthermore, quality control criteria were developed during the development of embodiments of the technology. The sensors exposed to establish QC criteria were reasonably consistent and a QC test window was established.

Based on experiments in which 11 exposures at 8 ppm for 2 hours (16 ppm-hour) were recorded, an average response of 8.11 mm was measured. The sensors from the QC test were left at ambient (room) temperature for 6 hours after their $H_2S$ exposure and then imaged again. The amount of response changed very little over the 6 hours indicating good response stability. These results indicate that (i) the microfluidic cells can be used as cumulative dosimeters and (ii) the total exposure dose can be calculated by measuring the length of the change in LC orientations. Using the algorithm one can use these dosimeters to determine an unknown concentration.

In addition, a microfluidic cell for measuring $H_2S$ was prepared and tested as a sensor for environmental monitoring. In these experiments, embodiments were tested that were designed to detect lower concentrations of $H_2S$ over longer time periods of time, which is appropriate for environmental monitoring. In particular, the microfluidic cell was tested under conditions appropriate for a device designed to detect approximately ppm-level concentrations of $H_2S$ during a typical work shift (e.g., for 8 to 12 hour exposures).

Sensors were exposed to $H_2S$ as described above and the minimum times needed for a response was recorded. In these experiments, a response is defined as the first visually detectable bright front observed on the sensor (typically ~0.5 mm in length). Data were collected for exposure to $H_2S$ over a range of 15 to 50 ppb. Responses were observed for $H_2S$ concentrations of 15 ppb, 16.67 ppb, 25 ppb, and 50 ppb at exposure times of 72 hours, 72 hours, 48 hours, and 24 hours, respectively.

These results indicate that much lower concentrations of target gases are detectable by increasing the exposure time. Such performance is of value for environmental monitoring where lower concentrations of toxic gas may be present for extended times.

Example 4

Effect of Head Space Height of the Microfluidic Cells on Sensitivity

During the development of embodiments of the present technology, experiments were performed to determine the effect of head space height on the sensitivity of the microfluidic cells ("cumulative sensors").

Cumulative sensors were prepared using 3.8 cm×1.9 cm glass substrates coated with polymer micropillars fabricated using standard photolithography. The polymer micropillars were 5 micron tall, 10 micron diameter with 20 micron center to center spacing and covered 3.5 cm×1.3 cm area on the glass substrate. The micropillared glass substrate was coated with a 20 Å thick titanium layer followed by a 100 Å thick gold film. The gold coated substrates were chemically functionalized by forming self-assembled monolayers of 11-mercaptoundecanoic acid (MUA) after incubating the substrate in 1 mM ethanolic solution for ~16 hrs. These substrates were then rinsed thoroughly with ethanol and dried in a stream of $N_2$. The substrates were then subjected briefly (15 s) to UV ozone treatment, then rinsed thoroughly with ethanol and dried in a stream of $N_2$. The microstructured substrate was then spin coated with 1 mL of 1 mM ethanolic solution of lead(II) perchlorate. The micropillared area of the substrate was then filled with ~3 microliter of LC E7:octane (40:60) mixture. A U-shaped polymer strip (~1 mm wide) was patterned on another glass substrate using photolithography. The thickness of the polymer strip was maintained at 25 micron. This substrate was coated with OTS and paired with the LC filled substrate to form a head-space 20 microns thick head space. A U-shaped mylar film was placed over the polymer strip to generate microfluidic cell with 45 micron head space. The substrates were held together using binder clips and three sides with the polymer/mylar strips were sealed using low off-gassing epoxy to force the gas diffusion through the open end of the sensor. These cumulative sensors, were stored in an argon environment prior to use.

Figure 11:
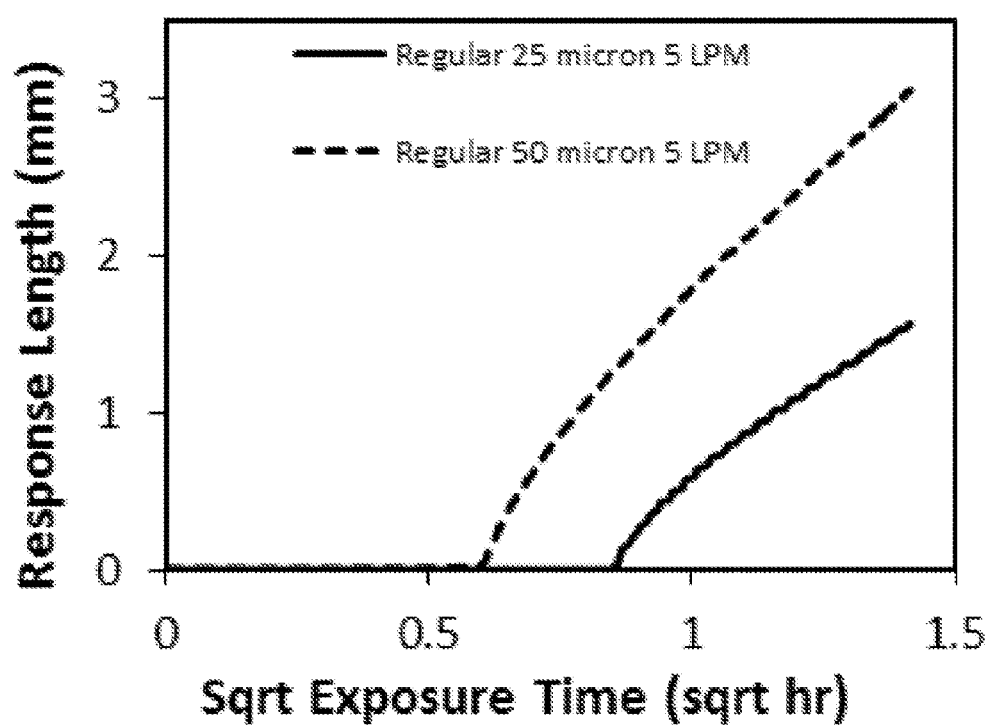
FIG. 11 shows the effect of thickness of the headspace height on the response of microfluidic sensor.

The cumulative sensors were then exposed to 1 ppm $H_2S$ at 45% RH inside a smaller exposure chamber (9.5×7.5×4.5 $cm^3$) at a flow rate of 5 L/min. The exposure chamber was placed between two crossed polarizers and was flanked by a CCD camera and diffused light source. The digital images of the cumulative sensors were captured in real-time as the sensor was exposed to the $H_2S$ gas. The captured images were then analyzed to determine the length of the bright front as a function of exposure time using ImageJ (NIH). FIG. 11 shows the variation of the response length as a function of the square root of the exposure time. The results show that the response length, after an initial delay, increases linearly with square root of the exposure time. And also shows that the cumulative sensors with thicker head space height are more sensitive (shorter delay and higher response length) than the sensors with thinner head space height.

These results again establish that the microfluidic cells can be used for tuning the dynamic range of detection of different gases.

Example 5

Microfluidic Cells as Real-Time Sensors

Figure 12:
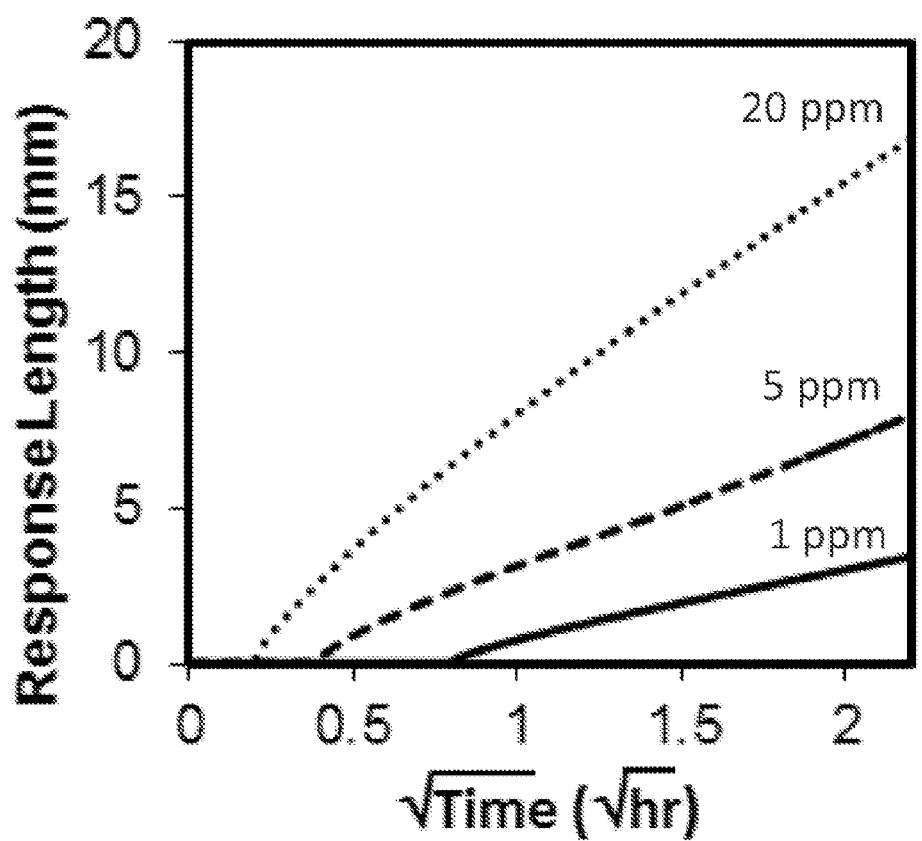
FIG. 12 shows the effect of different concentrations of $H_2S$ on response from microfluidic sensor.

During the development of embodiments of the present technology, experiments were performed to demonstrate that the microfluidic sensors can be used as real time sensors. The microfluidic cells were fabricated as described in Example 4. These cells were then exposed to different concentrations of $H_2S$ at 45% RH inside the small exposure chamber at 500 ml/min flow rate. The images of the sensors were then captured in realtime using CCD camera. These images were then analysed to determine the response length (the width of the bright front). FIG. 12 shows the variation of the response length as a function of the square root of the response time. The results show that the response length, after an initial delay, shows linear behavior with the square root of the exposure time. The slopes of these straight lines are different for different concentrations. These results indicate that measurement of the slope of these lines in real-time can provide a basis for a real-time sensor using these microfluidic cells.

Figure 13:
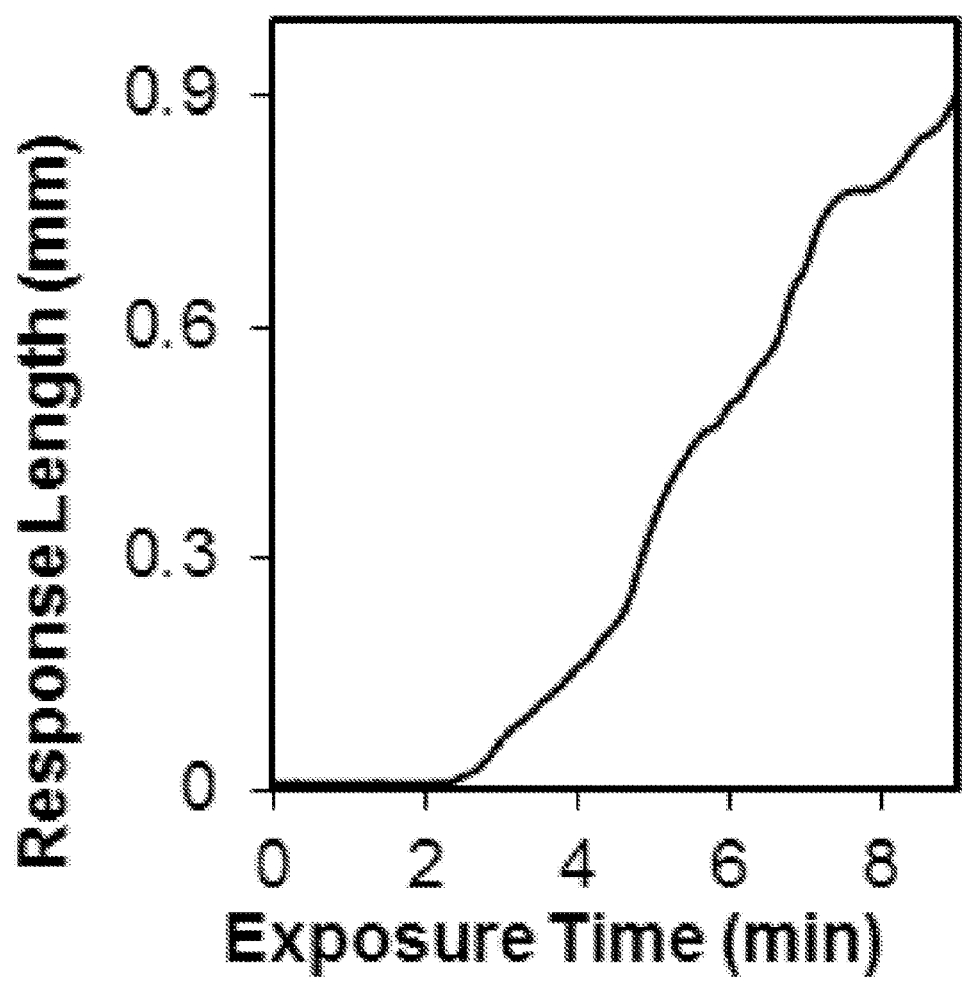
FIG. 13 shows the response from a microfluidic sensor with 45 micron head space and with micropillared area extending to the edge.

During the development of embodiments of the present technology, experiments were performed to demonstrate that some modifications in the microfluidic cell format can lead to detection of analyte with significantly shorter initial delay. Microfluidic cells were fabricated using the rectangular micropillared area as described in Example 4 except after filling the micropillared area with LC, the excess glass on the short side of the substrate extending to the edge of the substrate was removed so that micropillared area extended to the edge of the substrate. This substrate was then paired with another glass piece coated with OTS to form a ~45 micron head space between the top surface and LC surface. Two substrates were then glued together along three sides using low-off-gassing epoxy. The microfluidic cell was then exposed inside the small exposure chamber (9.5×7.5×4.5 cm$^3$) at a flow rate of 5 L/min while its appearance was captured in real-time using a CCD camera. The digital images were then analyzed to determine the response length as a function of exposure time. FIG. 13 shows the variation of the response length as a function of time. The results clearly show that with this cell configuration detection of 1 ppm of $H_2S$ is possible within 4 minutes of delay.

During the development of embodiments of the present technology, experiments were performed to determine if the microfluidic cells can actually be used to detect the change in the concentration of $H_2S$.

Figure 14:
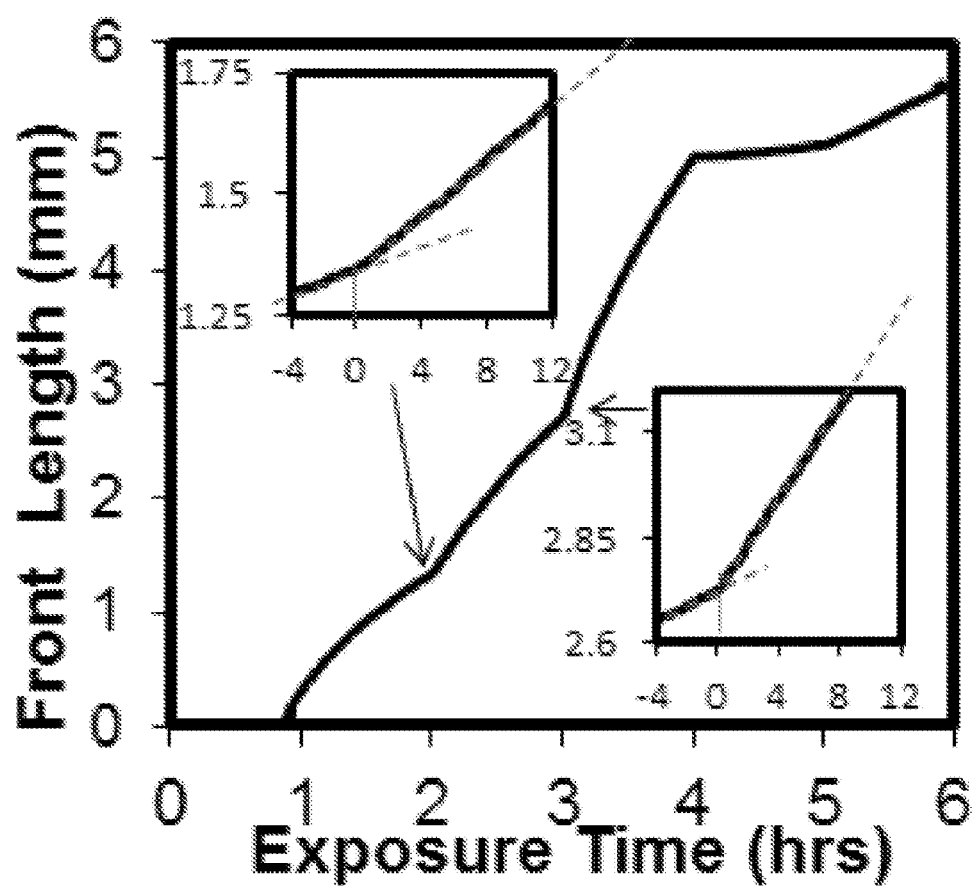
FIG. 14 shows variation of the response length as a function of the exposure time for real-time detection of $H_2S$ using microfluidic cell.

A microfluidic cell with 20 micron head space was fabricated as described in Example 4 and sequentially exposed to different concentrations 1, 2, 5, 1, and 2 ppm $H_2S$ for 2, 1, 1, 1, 1, hours respectively. The $H_2S$ concentrations were maintained at 45% RH at a flow rate of 500 ml/min inside a small (9.5×7.5×4.5 cm$^3$) exposure chamber. The response of the microfluidic cell to the exposure was recorded in real-time and the images were analyzed. FIG. 14 shows variation of the response length as a function of the exposure time. The results show that the microfluidic cell actually responds to the change in concentration of $H_2S$ whether it is increasing or decreasing. As shown in the insets of FIG. 14, the change in concentration can be detected within few minutes of the change in concentrations. These results when combined together demonstrate that the microfluidic cells designed for cumulative measurement of gas analyte can be used for real-time detection.

Example 6

Microfluidic Cells for Cumulative Detection of Formaldehyde

During the development of embodiments of the technology provided, experiments were performed to demonstrate that the microfluidic cells can be used to detect HCHO (formaldehyde) using LC-based detection technology. In this regard, first detection of HCHO was demonstrated using simple LC sensors. Next, microfluidic cells were fabricated using the LC and the micropillared substrate to demonstrate that these cells can be used for cumulative detection of HCHO.

HCHO sensors were fabricated on patterned glass substrates decorated with polymer micro-pillars using conventional lithographic techniques. The array of micropillars covered a 5 mm diameter area of the substrate. A droplet of LC (methoxybenzilidene butylanaline i.e. MBBA), when deposited onto the array of micro-pillars was subjected to capillary forces that caused the LC to spread to form a stable film. The pillar height (5 microns) determined the thickness of the film. These sensors were then exposed to vapors generated by bubbling nitrogen ($N_2$) through the targeted chemicals. For example, HCHO vapor was generated by bubbling $N_2$ through HCHO in deionized water. The desired concentrations of HCHO were generated by diluting the saturated stream with dry $N_2$. The HCHO concentration was determined using a commercial HCHO detector (FP-30, RKI Instruments Inc.).

Figure 15:
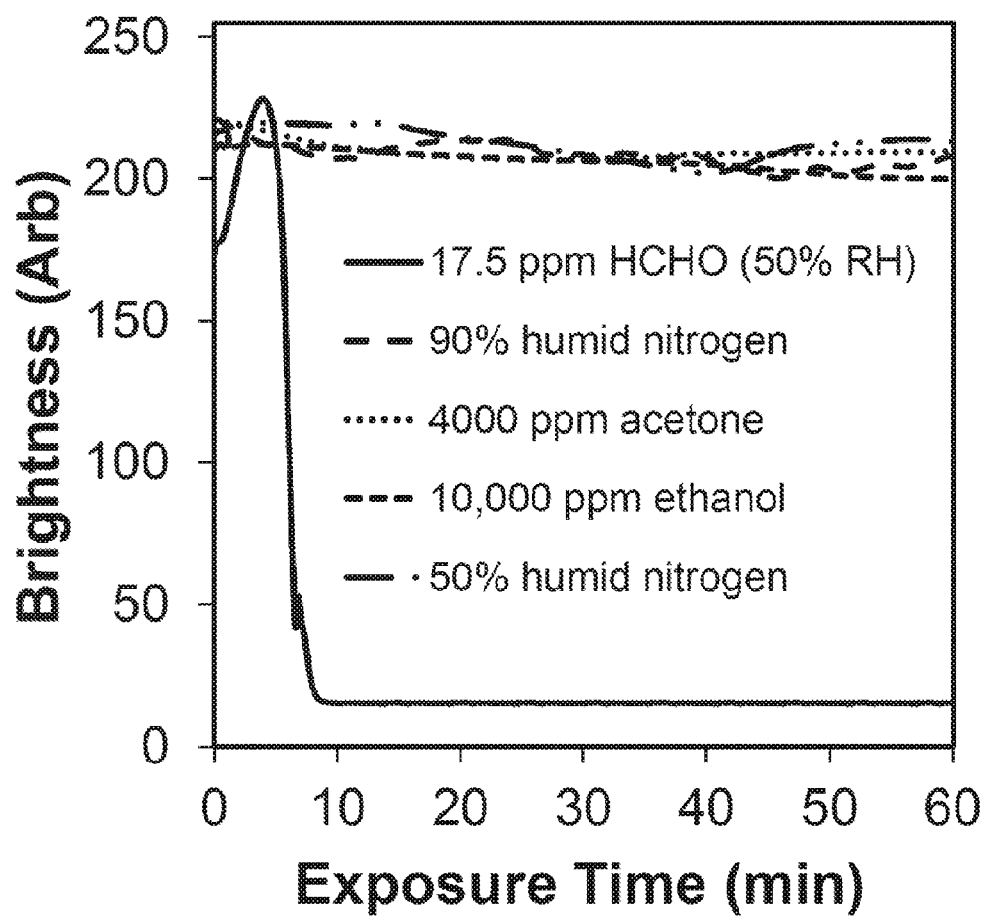
FIG. 15 shows the optical response of a liquid crystal sensor exposed to 17.5 ppm HCHO and non-targeted vapors. The transmitted light intensity was captured by digital camera and expressed as brightness.

The film of LC, when supported on the sensor surface, possesses optical birefringence and leads to a bright optical appearance of the sensor. Upon exposure to 17.5 parts per million (ppm) HCHO, the LC changes to an isotropic liquid with no optical birefringence and the sensor changes to a dark appearance between crossed polarizers. A measurement of the amount of light transmitted through the sensor as a function of time provides the dynamic response of the sensor to HCHO. The sensor yields a measurable response to 17.5 ppm HCHO (with 50% RH) in approximately 5 minutes (FIG. 15).

Furthermore, the data demonstrate the high selectivity of this sensor for HCHO relative to vapors from other chemicals representative of alcohol and ketone groups. Using this sensor system, 7 ppm HCHO was detected in less than 30 minutes. In addition, experiments measured the threshold concentrations of toluene, hexane, benzene, and isopropanol vapors required to induce a phase transition in a range of LCs (e.g., MBBA, 5CB, E7, TL205, MLC-7800) to be greater than 1000 ppm. Without being bound by theory, it is believed that the response of MBBA to low ppm concentrations of HCHO reflects, specific interactions between HCHO and the 4-butylaniline, one of the components present in MBBA. However, an understanding of the mechanism is not required to practice the technology.

Figure 16:
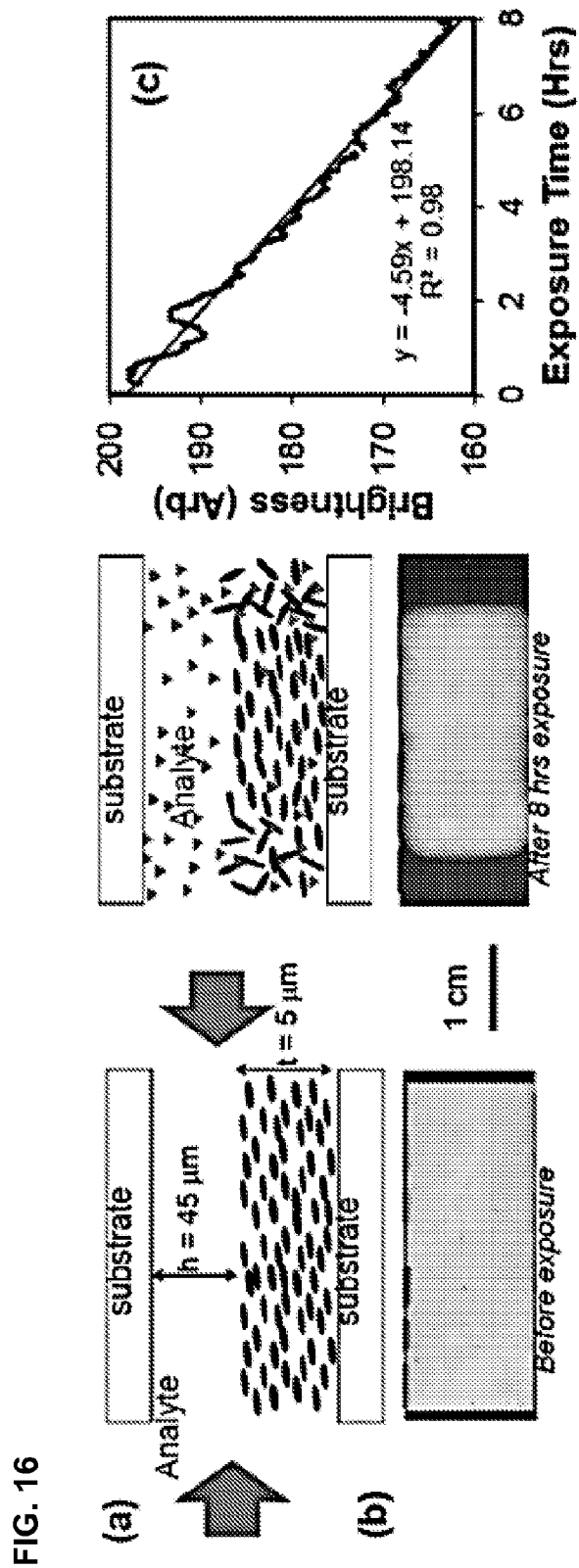
FIG. 16 shows the detection of cumulative exposure to HCHO using liquid crystal-based dosimeter badges.

Experiments were performed to collect data demonstrating use of the LC-based principles for cumulative detection of HCHO. Embodiments of the technology were fabricated (e.g., in the form of a cumulative dosimeter) and exposed to 7 ppm HCHO. The dosimeter was fabricated by using a 3.8 cm×1.9 cm glass substrate with a 3.5 cm×1.3 cm micropillared area. The micropillared area was filled with the LC using capillary action to form a thin (5 micron) film. This sensor substrate was then paired with a clean glass substrate with a head-space (e.g., a head space of approximately 45 microns) to allow controlled diffusion of the targeted analytes above the LC film (FIG. 16a). When viewed between crossed-polarizers, the dosimeter initially appeared bright (FIG. 16b). The dosimeter was then exposed to 7 ppm HCHO at a flow rate of 200 ml/minute for 8 hours. Dark fronts appear in ~30 minutes and progress inward with time (see, e.g., FIG. 16b). As a result, the measured light intensity decreases linearly with exposure time (FIG. 16c). The results demonstrate that exposure to HCHO leads to a phase transition of the LC that is evidenced as a dark front on each side of the dosimeter and that evolves as a linear function of exposure time. The dark front moves linearly with cumulative exposure to HCHO (FIG. 16c). Additionally, the fronts stay unchanged for days in an ambient environment, suggesting that these dosimeters provide a stable reading of cumulative exposure over a typical (e.g., 8-hour) work shift. Accordingly, these data demonstrated the feasibility LC-based microfluidic cell to create a passive dosimeter badge for toxic gases. The LC-based dosimeters are small (~4 cm×2 cm), light weight (<5 g), and easily read by light intensity measurement to indicate cumulative exposure to an analyte in the gas phase, e.g., HCHO.

Example 7

Channel-Based Analyte Sensor

During the development of embodiments of the present technology, experiments were performed to test devices comprising a channel (e.g., a microfluidic channel) for use in methods in which a functionalized surface in the channel is first exposed to an analyte and then the reacted functionalized surface is exposed to a liquid crystal for reading the device. While the embodiments tested demonstrate the general applicability of the technology, data were collected for an exemplary device comprising a gold surface functionalized with a self-assembled monolayer (SAM) of 4-aminothiophenol (ATP) to detect oxides of nitrogen (e.g., NO or $NO_2$, e.g., via conversion of NO to $NO_2$). A methoxybenzilidene butylanaline (MBBA) liquid crystal was applied to the reacted ATP surface to measure the $NO_2$ levels.

Some applications of gas monitoring relate to detecting low levels (e.g., parts per billion) of gases. For example, some biomedical applications relate to detecting nitric oxide (NO) gas in human breath for asthma monitoring. Detection of NO via conversion to $NO_2$ and detecting the $NO_2$ using various compounds (e.g., substituted aniline-based compounds) has been identified as one approach for detecting NO. Among these approaches, ATP was identified as a substituted aniline compound for use in a NO detector. Experiments were conducted using a Fourier transform infrared spectroscopy (FTIR) instrument equipped with a Specular Apertured Grazing Angle (SAGA) accessory to detect functional groups present on a SAM surface. In particular, experiments were performed to re-examine the ATP SAM, LC alignment on an ATP SAM coated surface, and detection of $NO_2$ using these surfaces.

Characterization with FTIR SAGA

Figure 17:
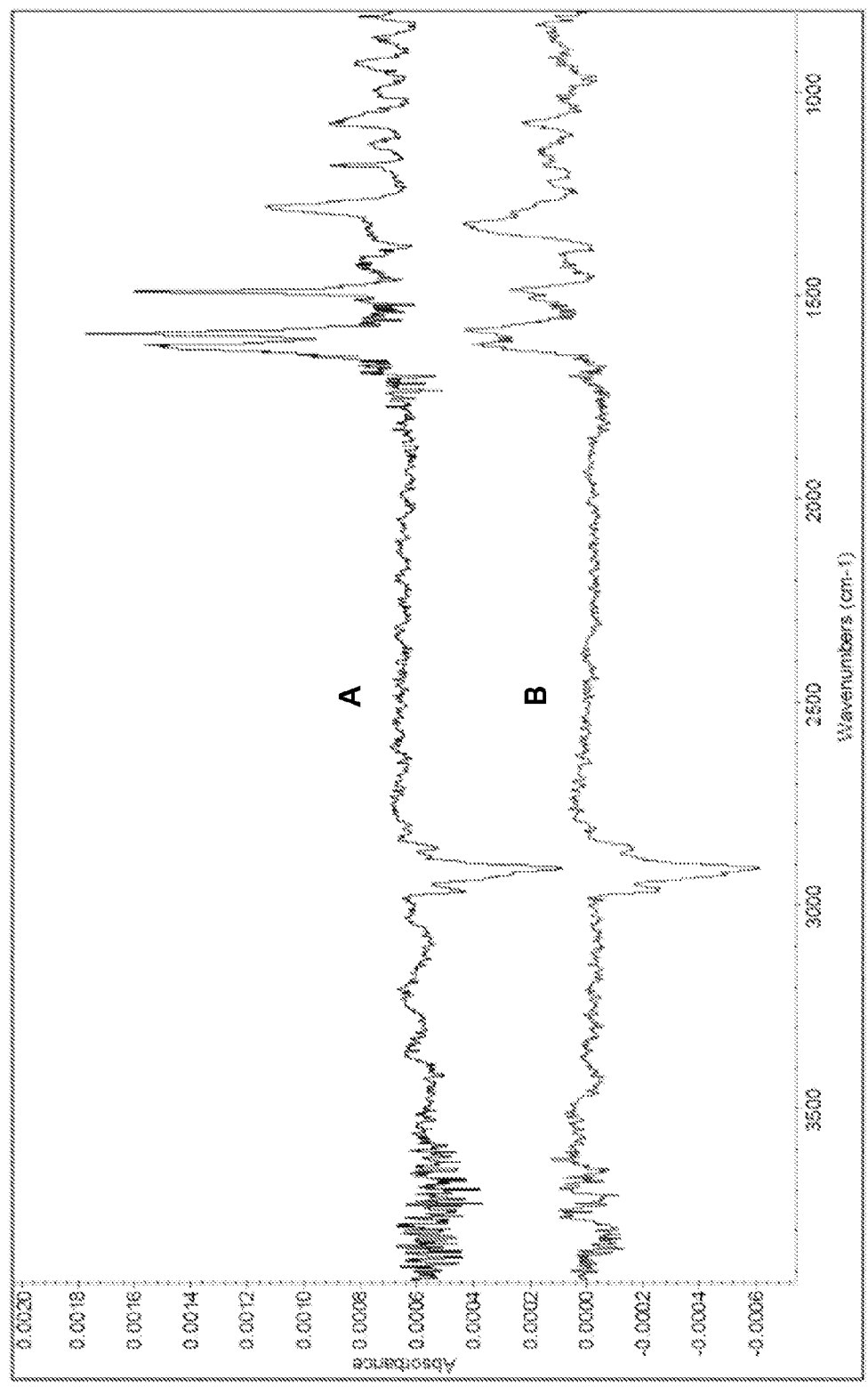
FIG. 17 shows Fourier transform infrared spectra acquired of a surface comprising an 4-aminothiophenol film before (spectrum A) and after (spectrum B) exposure to $NO_2$.

Glass slides coated with 1000 Å gold were immersed in ~1 mM ATP for ~16 hours. The substrates were rinsed with ethanol and dried in a stream of $N_2$. Using FTIR-SAGA, a background FTIR signal was acquired with a bare gold substrate that was soaked in ethanol overnight. The FTIR spectrum of ATP SAM was collected using the background spectrum as a reference. The ATP peaks were clearly visible with three prominent peaks at 1480, 1590, and 1620 $cm^{-1}$, corresponding to $v_{cc}$, $v_{cc}$, and $\delta_{NH}$ modes, respectively. In some experiments, inverted peaks in the hydrocarbon region (2900 $cm^{-1}$) indicated contamination of the reference gold surface that was resolved by cleaning the surface with a butane torch. Once the FTIR spectrum was collected, the substrate was placed inside an exposure chamber and exposed to 3.5 ppm humid $NO_2$ (50 sccm 4.7 ppm $NO_2$ and 20 sccm $N_2$ bubbled through $H_2O$) for approximately 30 minutes. The FTIR spectrum of the exposed surface showed some change in these three peaks, although no new prominent peaks were observed (FIG. 17).

Figure 18:
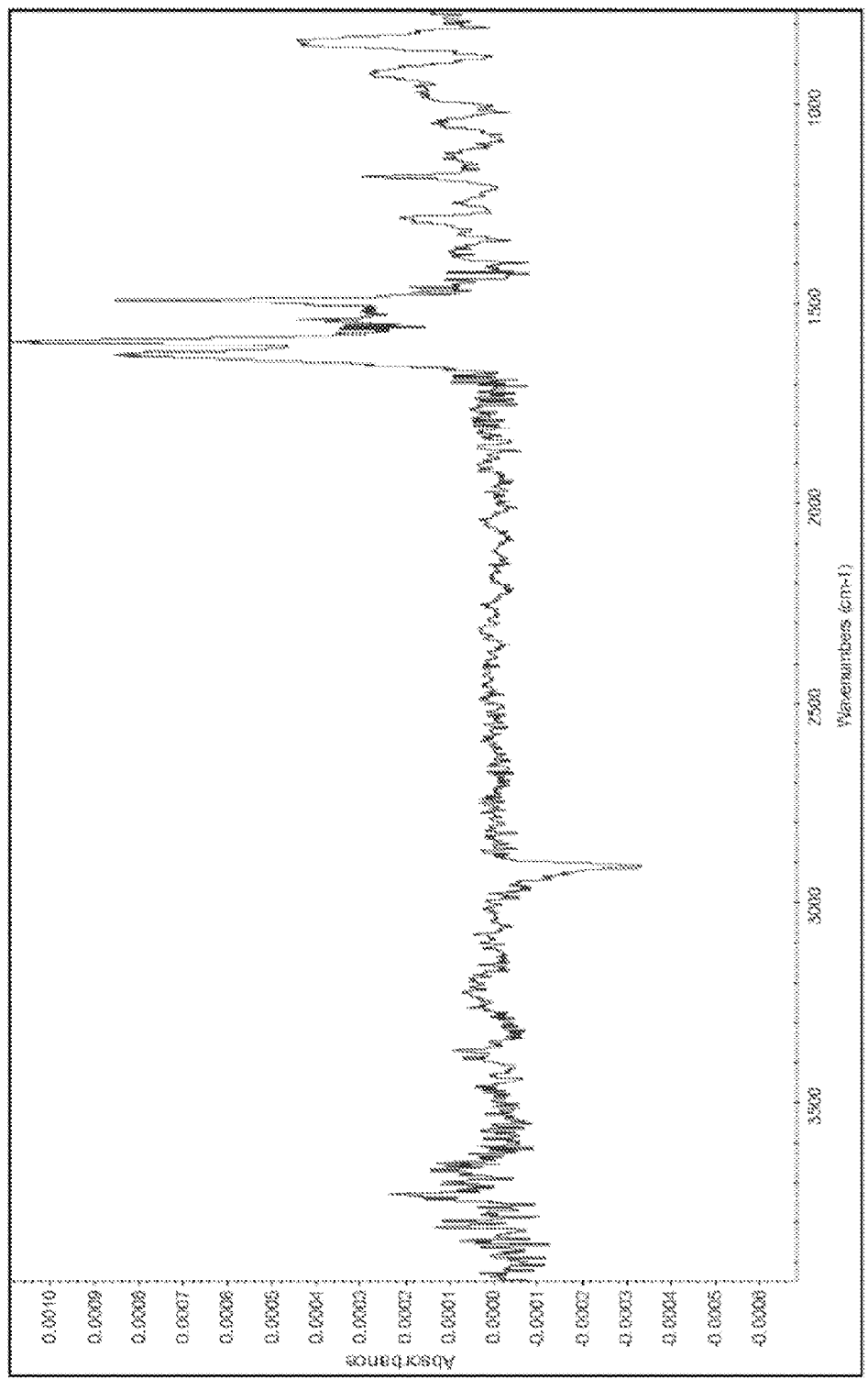
FIG. 18 shows a Fourier transform infrared spectrum acquired of a 100 Å silicon wafer comprising a 4-aminothiophenol film.

Next, to test the ability of the instruments to detect the presence of ATP film on a 100 Å thick gold film, experiments were performed with silicon wafers. A fresh (e.g., one-day old) gold coated silicon wafer was incubated in 1 mM ATP for ~16 hrs, rinsed with ethanol, and dried in a stream of $N_2$. Background spectra were collected from a piece of the same silicon substrate that was rinsed with ethanol and dried in stream of $N_2$. The peaks were well resolved and with the presence of some background moisture (FIG. 18).

Figure 19:
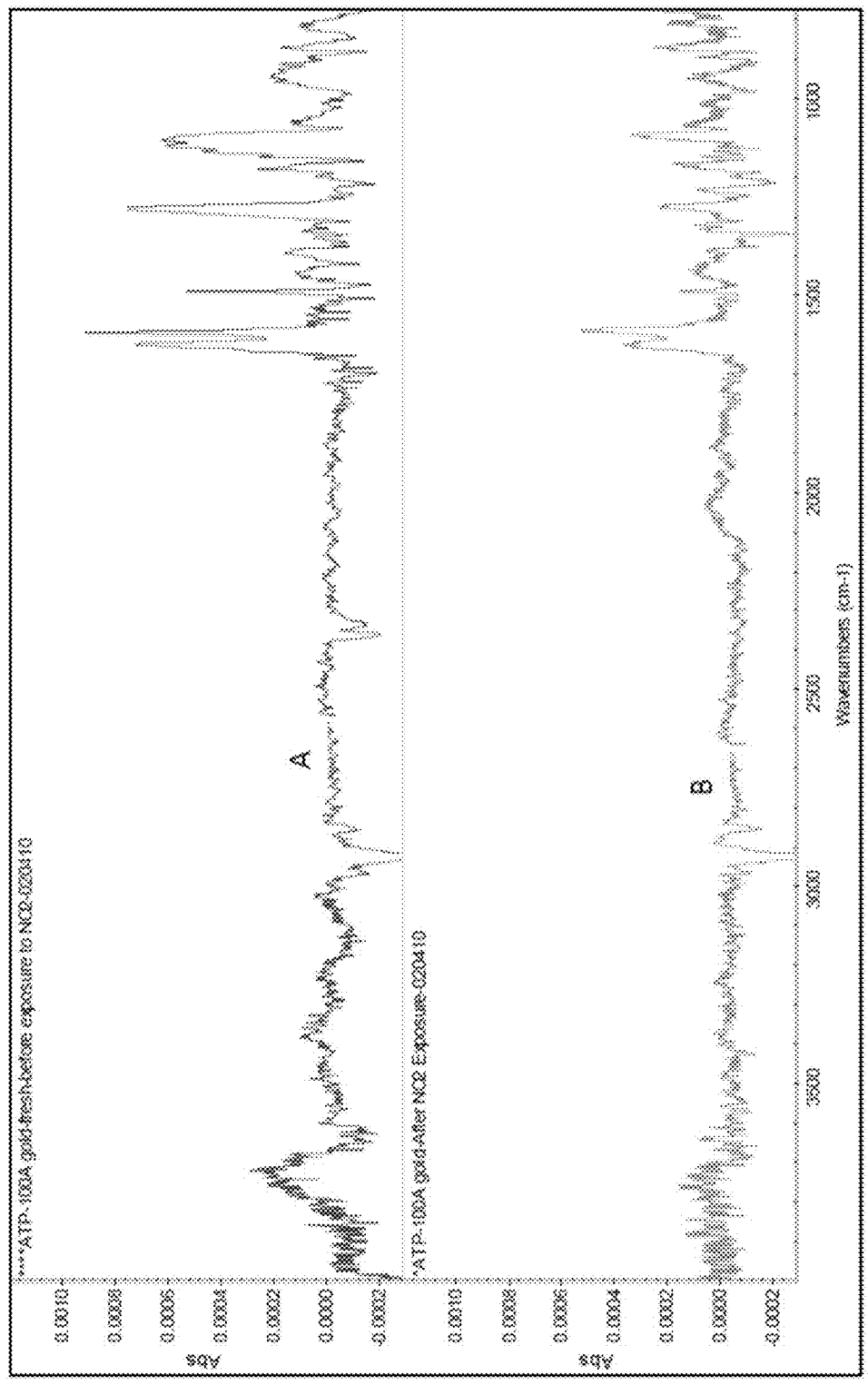
FIG. 19 shows Fourier transform infrared spectra acquired of a 100 Å gold surface comprising an 4-aminothiophenol film before (spectrum A) and after (spectrum B) exposure to $NO_2$.

Experiments were performed to test the ability of SAGA to resolve the FTIR spectra on 100 Å gold deposited on a glass substrate. For these experiments, two fresh gold (100 Å) coated microscope slides were incubated in 1 mM ATP for ~16 hours, rinsed with ethanol, and dried in a stream of $N_2$. A background spectrum was collected from an identically prepared slide immersed in ethanol alone. The microscope slide was broken into two pieces. One half of the slide was used for FTIR experiments and the other half was used to prepare a LC cell. Analysis of the first halves of the slides showed that the FTIR peaks were well resolved (FIG. 19). The SAM surface was also exposed to 3.25 ppm $NO_2$ (100 sccm 4.2 ppm mixed with 20 sccm $N_2$ bubbled through water) for approximately 30 minutes. The film exposed to $NO_2$ showed a decrease in peak intensity and a small shift in the peak positions (FIG. 19). These experiments demonstrated that changes are detectable in the ATP monolayer on 100 Å thick gold surface upon exposure to $NO_2$ (e.g., by using FTIR).

Alignment of Different LCs on ATP Treated Surface:

After confirming the presence of an ATP monolayer using FTIR (above), experiments were conducted to prepare an ATP functionalized surface and evaluate the alignment of liquid crystals on the surface.

To prepare ATP-functionalized surfaces, glass slides were cleaned by ultrasonicating for 10 minutes in detergent, then rinsed in deionized water and washed in acetone and ethanol (reagent grade). A ~2 mM ATP solution in ethanol (~68.4 mg ATP dissolved in 200 ml ethanol) was prepared. Fresh gold coated slides were incubated on clean staining dishes; one staining dish was filled with ethanol for reference and two were filled with the ATP solution. Slides were incubated overnight, rinsed twice in 100% ethanol, and dried in $N_2$ before use.

To evaluate the alignment of liquid crystals on ATP treated surfaces, seven different liquid crystals having varying physical properties were tested:

A 5CB
B E7
C TL-205
D MLC-7800
E MLC-6488
F MBBA ($\Delta\epsilon<0$)
G MLC-14200 (high $\Delta\epsilon$)

A series of 1"×3" substrates were tested under the following conditions:

1 incubated in ethanol
2 functionalized with ATP
3 functionalized with ATP and exposed to $NO_2$
4 functionalized with ATP and exposed to $N_2$.

The substrates were cut into five pieces and paired with OTS treated slides and lifter slips before filling the devices with a LC in nematic phase. The alignment of LCs on these films was monitored for at least six days.

Figure 20A:
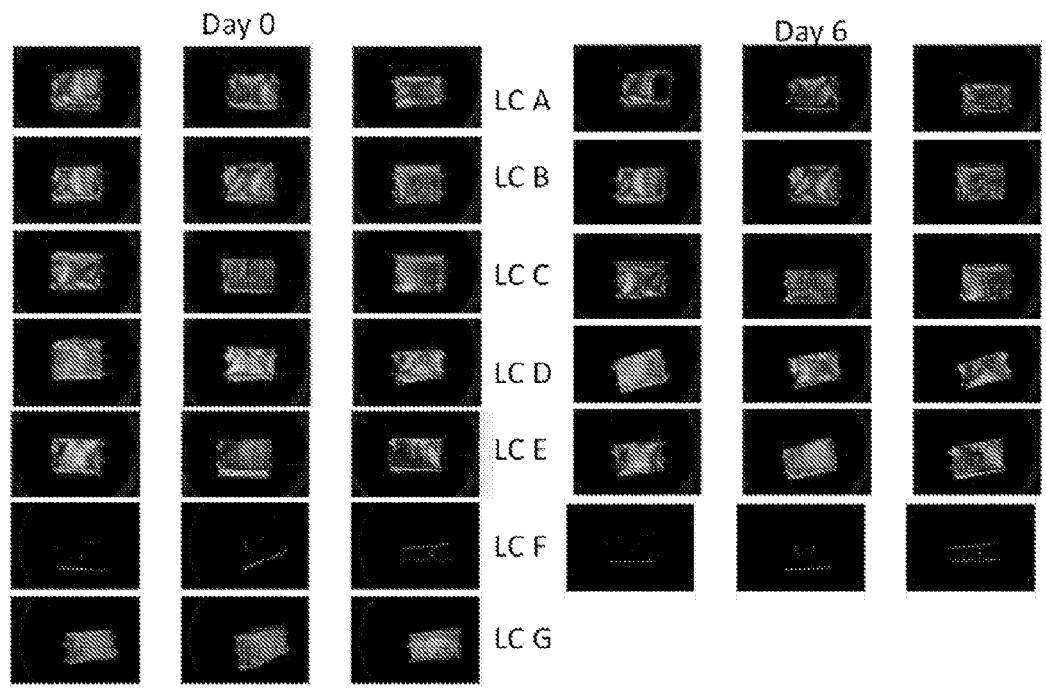
FIG. 20 shows the alignment of different liquid crystals on surfaces functionalized with 4-aminothiophenol before (FIG. 20A) and after exposure to $NO_2$ (FIG. 20B).
Figure 20B:
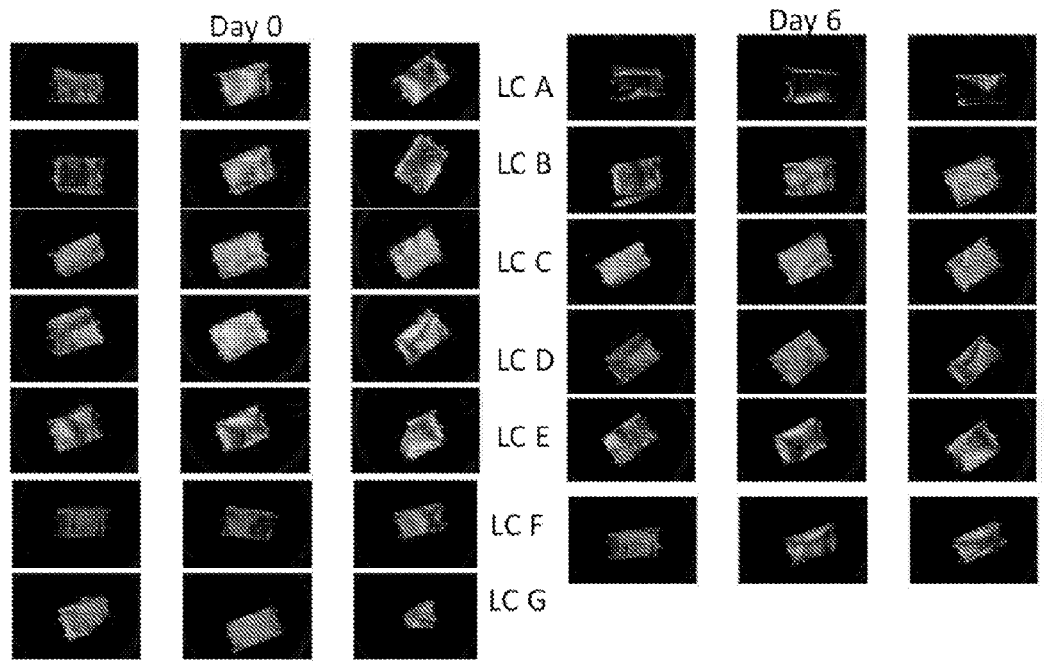

The results from these experiments show that 5CB aligns homeotropically on a bare gold substrate that was incubated in ethanol overnight (FIG. 20A). In addition, MBBA assumes a homeotropic alignment on an ATP functionalized surface and adopts a planar alignment on $NO_2$— exposed ATP functionalized surface (FIG. 20B). In these experiments, the other LCs tested did not show any significant change in LC alignment upon exposure to $NO_2$ (FIGS. 20A and 20B).

Figure 21:
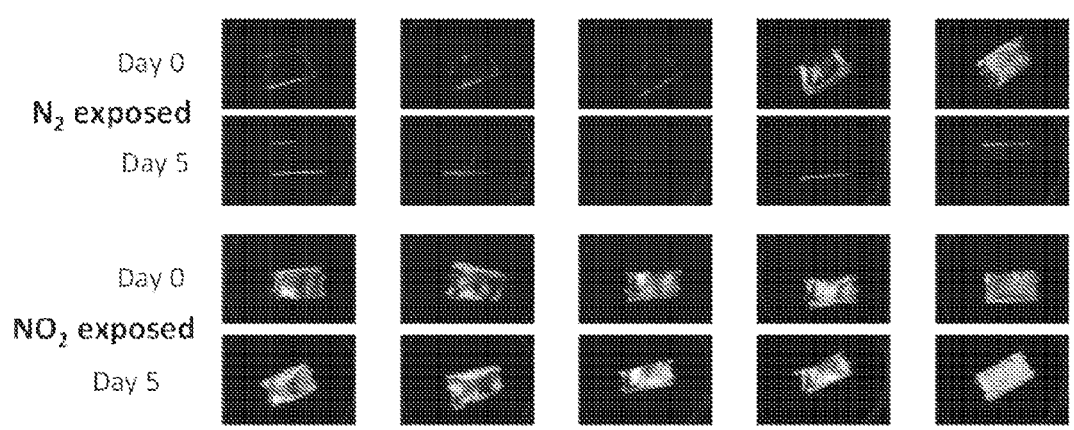
FIG. 21 shows the selective detection of $NO_2$ relative to humid gas.

To ensure that the change in LC alignment upon exposure to humid $NO_2$ was not from humidity alone, surfaces were prepared and exposed to 3.5 ppm $NO_2$ at 70 sccm (50 sccm 4.7 ppm $NO_2$ and 20 ppm $N_2$ bubbled through water). Identical surfaces were also prepared by exposing them to humid $N_2$. The results showed that the (i) ATP functionalized surface can be used to achieve homeotropic alignment of LC MBBA and (ii) LC MBBA can be used to report interaction of $NO_2$ with the ATP surface (FIG. 21).

Characterization of ATP Treated Surface:

The previous experiments suggested that a change occurred at the ATP surface as a result of exposure to $NO_2$ that can be reported by the LC MBBA. During the development of embodiments of the technology, experiments were conducted to characterize the surfaces using FTIR, contact angle, and ellipsometric measurements. These experiments established the reproducibility of the functionalized surfaces prepared as described herein on 1000 Å gold and 100 Å gold surfaces. For these experiments, the SAM coated slides were first prepared as described herein and then broken into two halves. One half was used for FTIR experiments and the second half was used for contact angle and ellipsometric measurements for the 1000 Å thick film.

Figure 22:
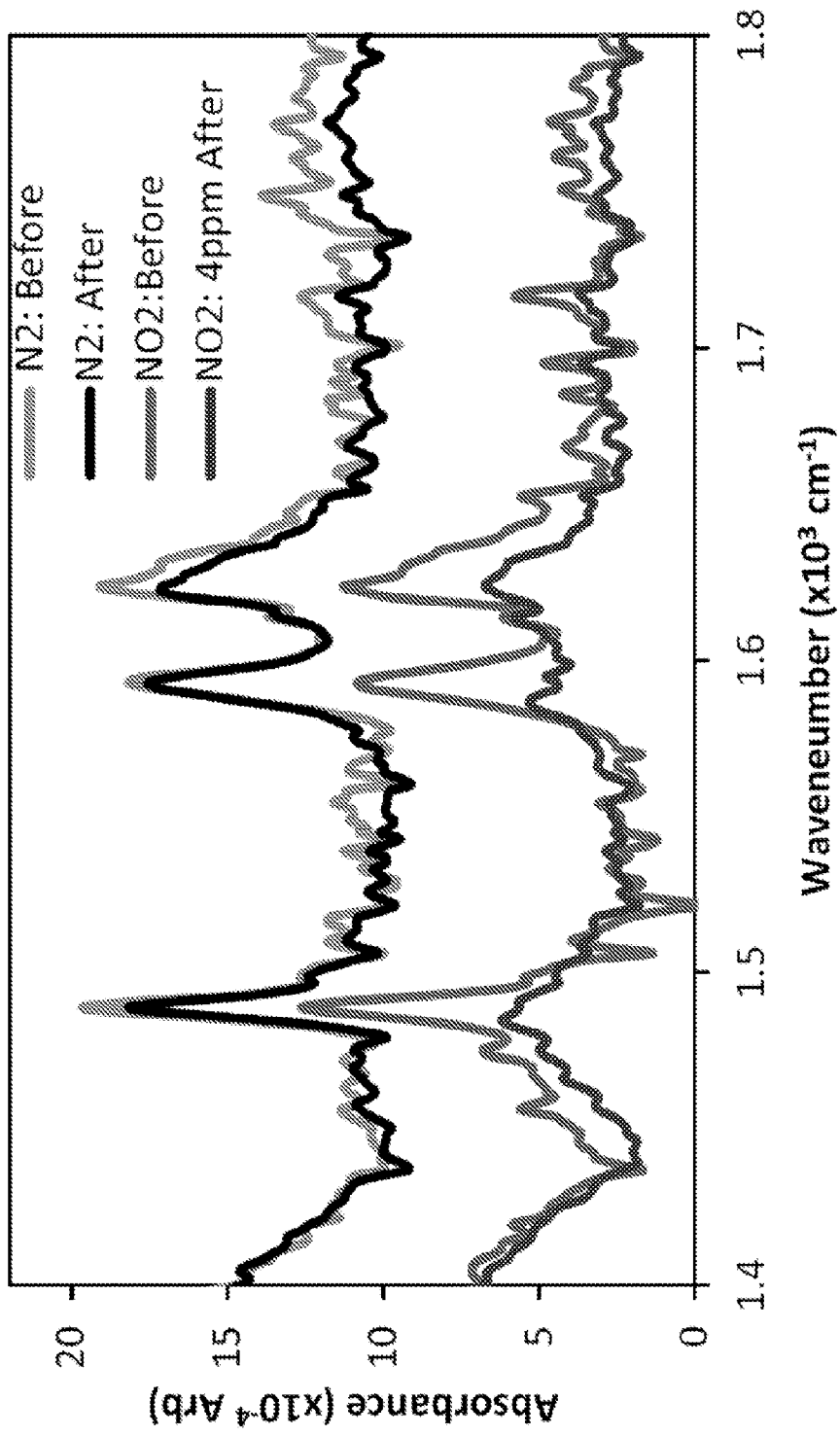
FIG. 22 shows Fourier transform infrared spectra acquired of a surface comprising a 4-aminothiophenol film before (grey) and after (black) exposure to $N_2$ (top spectra) and $NO_2$ (bottom spectra).

FTIR spectra acquired of the ATP SAM were comparable to grazing angle IR spectra reported in the literature (see, e.g., *Langmuir* 12 15 (1996) 3689). The spectra show a decrease, especially at 1480 cm$^{-1}$, in the peak intensity upon exposure to $NO_2$ (FIG. 22). FTIR spectra of ATP functionalized surfaces and surfaces exposed to humid $NO_2$ and humid $N_2$ are shown in FIG. 22. These results indicate that there are changes in the ATP surface upon exposure to $NO_2$ and the changes are not due to the presence of humidity.

Detection Using Channels:

The results of experiments performed during the development of embodiments of the technology described demonstrated that using a surface functionalized with ATP detects the presence of $NO_2$ by using LC MBBA. Experiments were conducted to verify that passing $NO_2$ gas through a narrow channel allows a faster reaction and therefore a sensitive detection with shorter response time (e.g. 30 min).

During the development of embodiments of the technology, a polydimethylsiloxane (PDMS) channel was prepared to provide a well defined gas flow path on an ATP treated substrate. A "master" was prepared by gluing a ~1 mm wide, 3 inch long, and 0.7 mm thick glass piece on a 1 inch×3 inch glass substrate using UV curable epoxy. A film of PDMS mixture (prepolymer and curing agent) was overlaid on the master and cured at 60° C. for 1 hour. The PDMS channel was removed from master, overlaid on the ATP functionalized surface and $NO_2$ gas was passed through the channel for 10 minutes using a small needle at the end of the gas delivery system. The exposed surfaces were then used to assemble LC cells by pairing them with OTS coated slides using 25 micron mylar as spacers. The LC cell was filled with MBBA in isotropic phase at 50° C. $NO_2$ concentrations of 88 ppb and 50 ppb were generated by mixing 4.7 ppm $NO_2$ from a certified cylinder (4.7 ppm) and humid nitrogen generated by bubbling nitrogen through DI water at appropriate ratios. For negative controls, $N_2$ was bubbled through deionized water.

Figure 23:
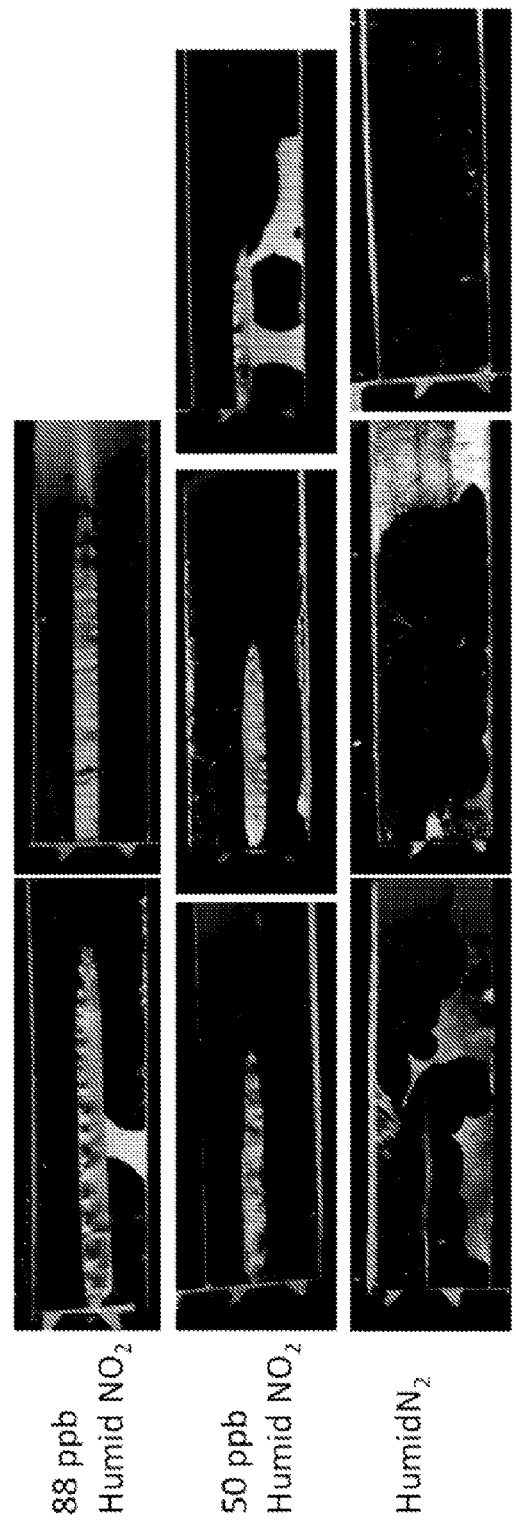
FIG. 23 shows the detection of NO₂ using channels defined by a polydimethylsiloxane channel. The images were acquired 2 minutes after filling the LC cell

The results show detection of 50 ppb $NO_2$ by the ATP coated surface exposed along the path defined by PDMS channel (FIG. 23). The results indicate that measuring the length of the bright path along the channel provides a means to quantify the response of the chemically functionalized surface to an analyte.

Figure 24:
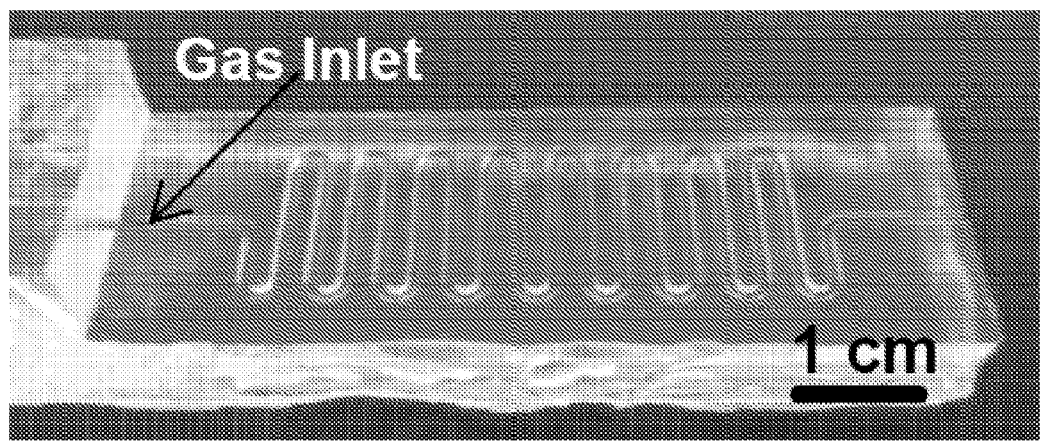
FIG. 24 shows an embodiment of a sensing device comprising a polydimethylsiloxane channel used to define the exposure path on a functionalized surface to increase the sensitivity of detection.

These results suggested that a longer channel having controlled dimensions would provide a more precise and accurate quantification of sensor response. Experiments were performed with PDMS channels prepared using an aluminum master having a 1 mm wide×1 mm thick ridge defining channel dimensions. To minimize the potential variation during introduction of the gas, a small needle (~1 mm diameter) was integrated into the PDMS block with channels (see FIG. 24). The ATP treated substrates were then consistently placed over the PDMS channels and exposed to different concentration of $NO_2$. Before exposure, the substrate was firmly pressed against the PDMS block and a weight was placed over the substrate during the exposure. After exposure, the PDMS channel was removed and the exposed surface was paired with an OTS treated glass substrate forming a 25 micron cavity using a mylar spacer. The two substrates were aligned leaving a small lip along the long edge of the cell to facilitate LC filling. The cell was secured and placed inside an oven at 60° C. LC MBBA was applied along the lip and allowed to spread inside the cell for 5 minutes while the cell remained inside the oven. After 5 minutes, the cell was taken out of the oven and the LC cell was imaged at different time intervals starting from 2 minutes.

Figure 25:
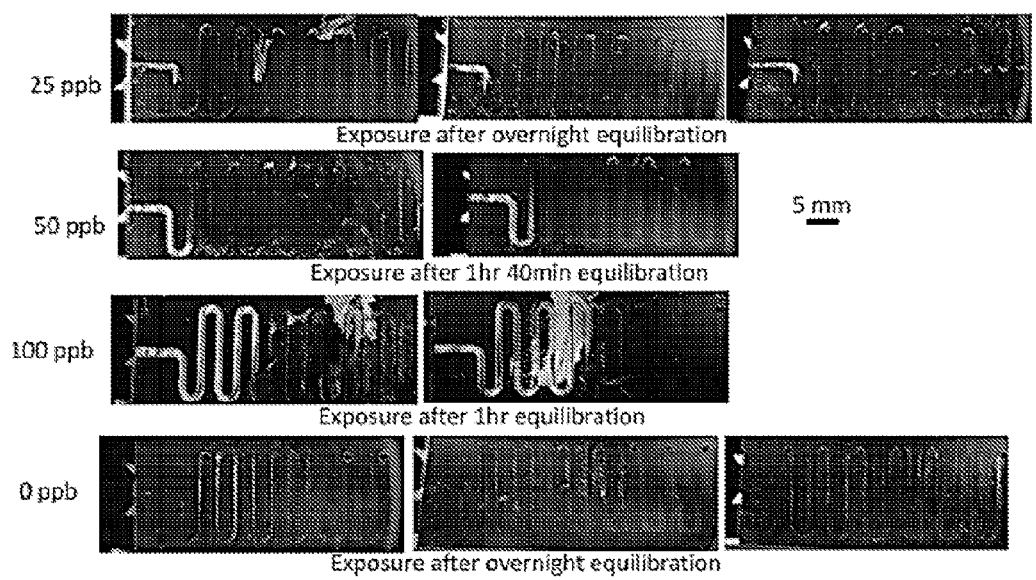
FIG. 25 shows the detection of different concentrations of NO₂ using polydimethylsiloxane channels to define the exposure path.

Exposure experiments were performed with different concentrations and different equilibration times. The results show that 25 ppb $NO_2$ is detected (FIG. 25).

Figure 26:
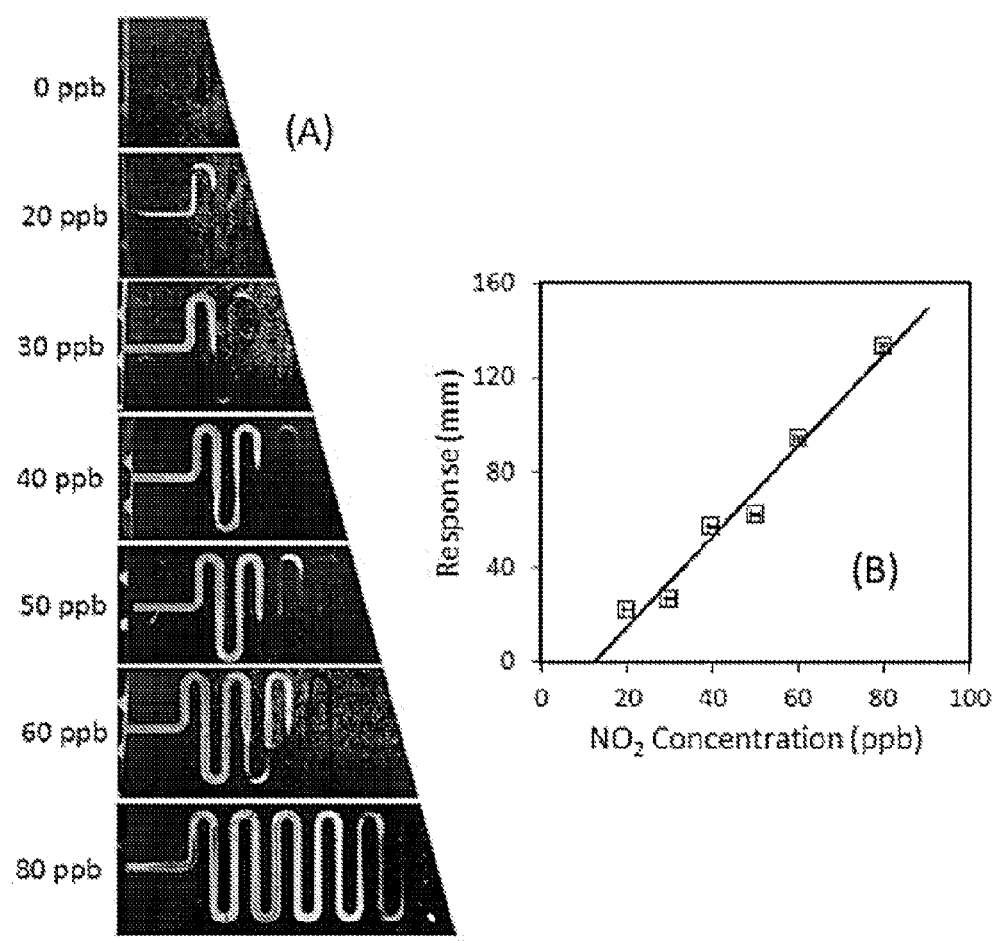
FIG. 26 shows a series of optical images demonstrating the response of an embodiment of the technology to different concentrations of NO₂ (FIG. 26A).

A number of experiments were performed at different concentrations ranging from 10 ppb to 80 ppb with a 10 ppb initial and then 20 ppb increments (FIG. 26). The images from three different replicates were captured and analyzed 4 minutes after removing the cells from the oven. These results show that this method detects 20 ppb of humid $NO_2$ after 10 minutes exposure with a resolution of 10 ppb. The results also show that measurement of the length of the reacted channel provides a facile method to quantify the response as a function of concentration. The results also show that there is a linear relationship between the length of the bright channel and the concentration (FIG. 26B,).

Effect of Liquid Crystal Composition

During the development of embodiments of the technology, liquid crystal compositions other than MBBA were tested. MBBA has negative dielectric anisotropy ($\Delta\epsilon<0$). Since most of the materials tested previously had a positive dielectric anisotropy ($\Delta\epsilon>0$), it was anticipated that LCs with negative dielectric anisotropy might align homoeotropically on ATP functionalized surfaces.

Figure 27:
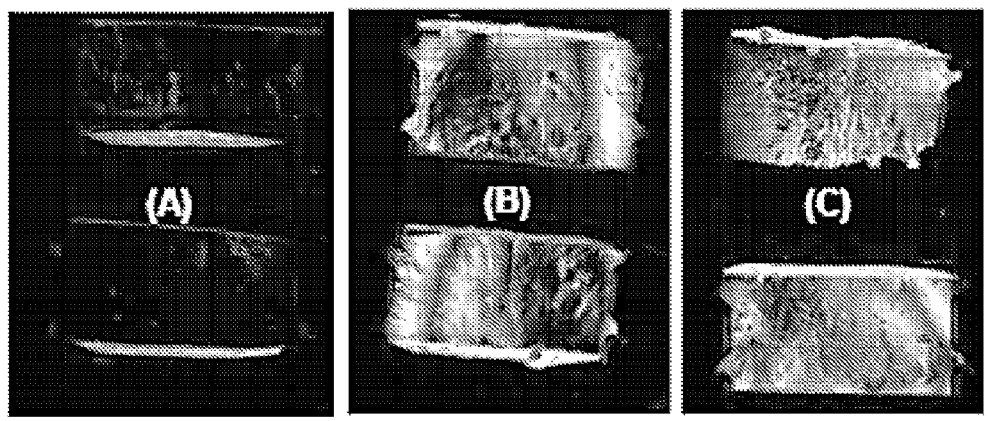
FIG. 27 shows the alignment of three liquid crystals having a negative dielectric anisotropy.

LC MLC-2080 and MLC-2081 (Merck), both with negative dielectric anisotropy, were tested. Both of these LCs have a nematic-transition temperature above 80° C. ATP treated surfaces were prepared using the protocol developed herein. The substrates were broken into six pieces and paired with OTS coated lifter slides. Two cells were then filled with MBBA, MLC-2080, and MLC-2081 in nematic phase. Images were taken after 15 minutes to assess the alignment of these LCs on the ATP coated surfaces (FIG. 27). The results suggest that MBBA aligns on the ATP coated surface (FIG. 27A) and that neither MLC-2080 nor MLC-2018 aligns homeotropically on the ATP coated surface (FIGS. 27B and 27C, respectively). The homeotropic alignment does not correlate with the dielectric anisotropy and it is contemplated that the homoeotropic alignment of MBBA on an ATP treated surface is due to the functional group present on MBBA.

Figure 28:
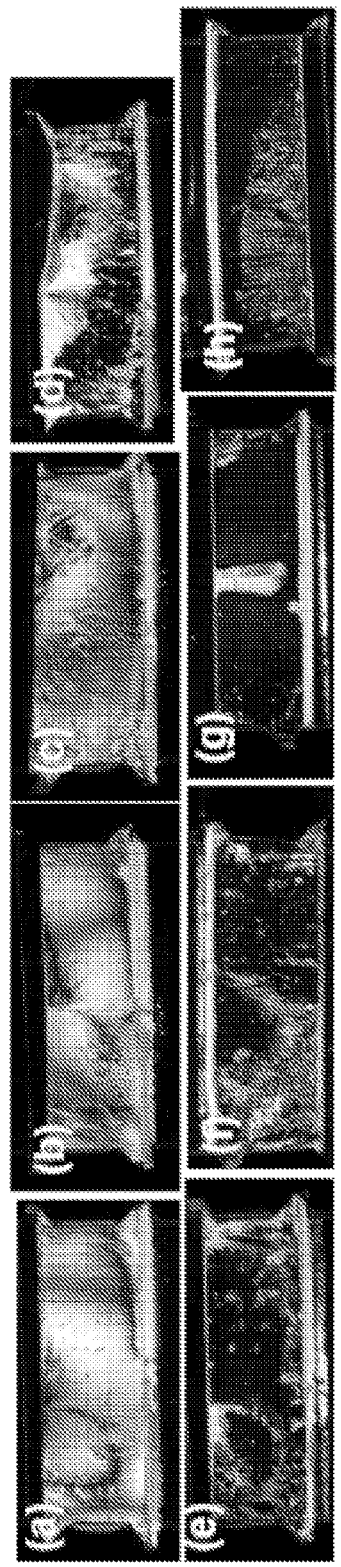
FIG. 28 shows the alignment of mixtures of MBBA and MLC-2080 at different ratios of MBBA to MLC-2080. Panels (a) through (h) show the alignment of MLC-2080 alone; mixtures of MLC-2080 and MBBA at ratios of 0.9 MLC-2080, 0.8 MLC-2080, 0.7 MLC-2080, 0.6 MLC-2080, 0.5 MLC-2080, and 0.25 MLC-2080; and MBBA alone, respectively.

To determine the effect of mixing MBBA with another LC having a negative dielectric anisotropy, MBBA was mixed with MLC-2080 at different volume ratios (pure MLC, 0.9 MLC, 0.8 MLC, 0.7 MLC, 0.6 MLC, 0.5 MLC, 0.25 MLC, and pure MBBA; see FIG. 28 (a) through (h), respectively). The mixtures were vortexed, heated to 65° C. for 5 minutes and vortexed again. The mixtures were monitored over several days to ensure that no phase separation occurred over time.

Two identically prepared ATP functionalized surfaces were broken into 8 different pieces. Each piece was then paired with a piece from an OTS coated glass substrate, thus forming a 25 micron thick LC cell. One cell each from each slide was then filled with the LC mixture at 60° C. inside an oven after equilibration for 2 minutes. After 2 minutes of equilibration, each cell was filled serially inside the oven. After 5 minutes, the oven was closed and the cells were equilibrated for another 5 minutes. The LC cells were imaged in the order they were filled. Images were taken after another 5 minutes of annealing at 60° C. The results suggest that the mixture of MLC-2080 and MBBA aligns homeotropically on an ATP treated surface at a concentration as high as 80% (FIG. 28). The incubation time inside the 60° C. oven needed to achieve homeotropic alignment increases with increase in MLC concentration. These results indicate that mixtures of LCs provide, in some embodiments, better sensitivity to $NO_2$ than a single LC (e.g., MBBA) alone.

Figure 29:
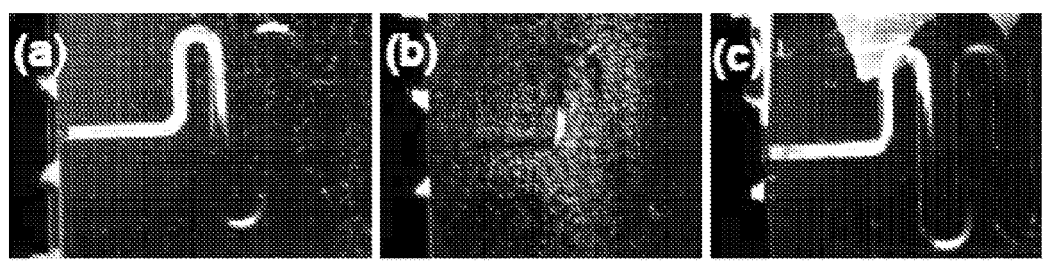
FIG. 29 shows on optical image of a liquid crystal cell fabricated with a 4-aminothiophenol functionalized surface exposed to NO₂ for different times and filled with liquid crystal compositions. Panels (a) through (c) are images of a cell exposed to 20 ppb humid NO₂ for 10 minutes then filled with MBBA, a cell exposed to 20 ppb humid NO₂ for 5 minutes then filled with MBBA, and a cell exposed to 20 ppb humid NO₂ for 5 minutes then filled with a mixture of MLC-2080 and MBBA at a 60 to 40 ratio.

To confirm this result, identically prepared ATP coated surfaces were exposed using the PDMS channel to 20 ppb $NO_2$ for 5 and 10 minutes, and they were then filled with pure MBBA or a mixture of MBBA and MLC-2080 at a 40:60 v/v ratio. Optical images were acquired of the cells fabricated using surfaces exposed to 20 ppb $NO_2$ and filled with different LC mixtures (FIG. 29). The images were taken after 10 minutes of equilibration at ambient temperature after removal from a 65° C. degree oven. The results show that 20 ppb $NO_2$ is detected using pure MBBA after a 10 minutes exposure (FIG. 29(a)). The surface exposed to 20 ppb $NO_2$ for 5 minutes and using pure MBBA does not give any measurable response (FIG. 29(b)). However, the mixture of MBBA and MLC-2080 at a 40:60 v/v ratio provides a measurable response after 5 minutes of exposure (FIG. 29(c)). The data show that (i) a longer exposure time gives more time for $NO_2$ to react and therefore provides a greater measurable response and (ii) sensitivity of detection can be improved by using MBBA-MLC2080 mixtures.

Effect of Flow Rate

Figure 30:
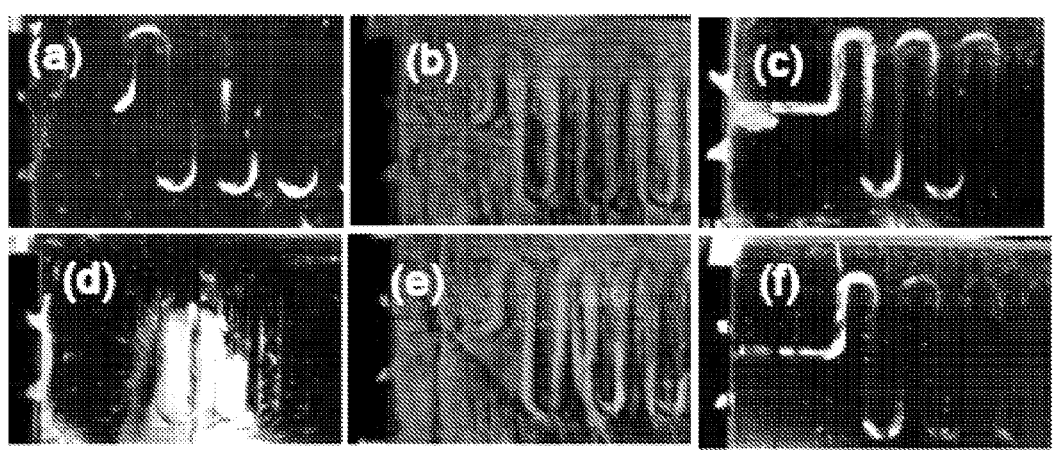
FIG. 30 shows optical images of cells comprising 4-aminothiophenol functionalized surfaces. Panels (a) through (f) show cells exposed to 20 ppb humid NO₂ at 800 sccm for 2 minutes and filled with pure MBBA; 10 ppb humid NO₂ at 800 sccm for 2 minutes and filled with MLC-2080 and MBBA at a 60 to 40 ratio; (c) 10 ppb humid NO₂ at 400 sccm for 2 minutes and filled with MLC-2080 and MBBA at a 60 to 40 ratio; (d) humid N₂ at 400 sccm for 2 minutes and filled with MLC-2080 and MBBA at a 60 to 40 ratio; (e) 20 ppb humid NO₂ at 800 sccm for 30 seconds and filled with MLC-2080 and MBBA at a 60 to 40 ratio; and (f) image of (e) after overnight storage at room temperature.

Experiments described above demonstrate that using the mixture MBBA and MLC-2080 at a 40:60 v/v ratio detects the presence of 20 ppb $NO_2$ after a 5 minute exposure at 100 sccm. Next, experiments were performed to determine if increasing the flow rate improves the sensitivity of detection. To test the flow effect, identical surfaces functionalized with ATP were prepared and exposed to different concentrations of $NO_2$ at different flow rates. The LC cells were fabricated and filled with pure MBBA and MBBA and MLC-2080 at a 40:60 v/v ratio. The images of the LC cells were collected 4 minutes after the cells were taken out of the oven (FIG. 30).

The results show that pure MBBA is anchored strongly so that at 800 sccm, $NO_2$ could not induce the planar alignment along the channel. The 800 sccm flow rate is too high and could potentially induce leaks outside the channel so that the mixture adopts a planar alignment with 2 minutes of exposure to 10 ppb or 30 seconds of exposure to 20 ppb. The cells detect 10 ppb $NO_2$ after two minutes of exposure at a flow of 400 sccm. It is contemplated that cells that are resistant to leaking under high flows detect the presence of 20 ppb after 30 seconds of exposure.

Channel-Based Analyte Sensor with Higher Resolution

During the development of embodiments of the technology provided herein, a dose response curve for an analyte gas was developed for a cell comprising a gold surface and 4-aminothiophenol. The cells were then applied to detect low concentrations of the analyte gas.

Figure 31:
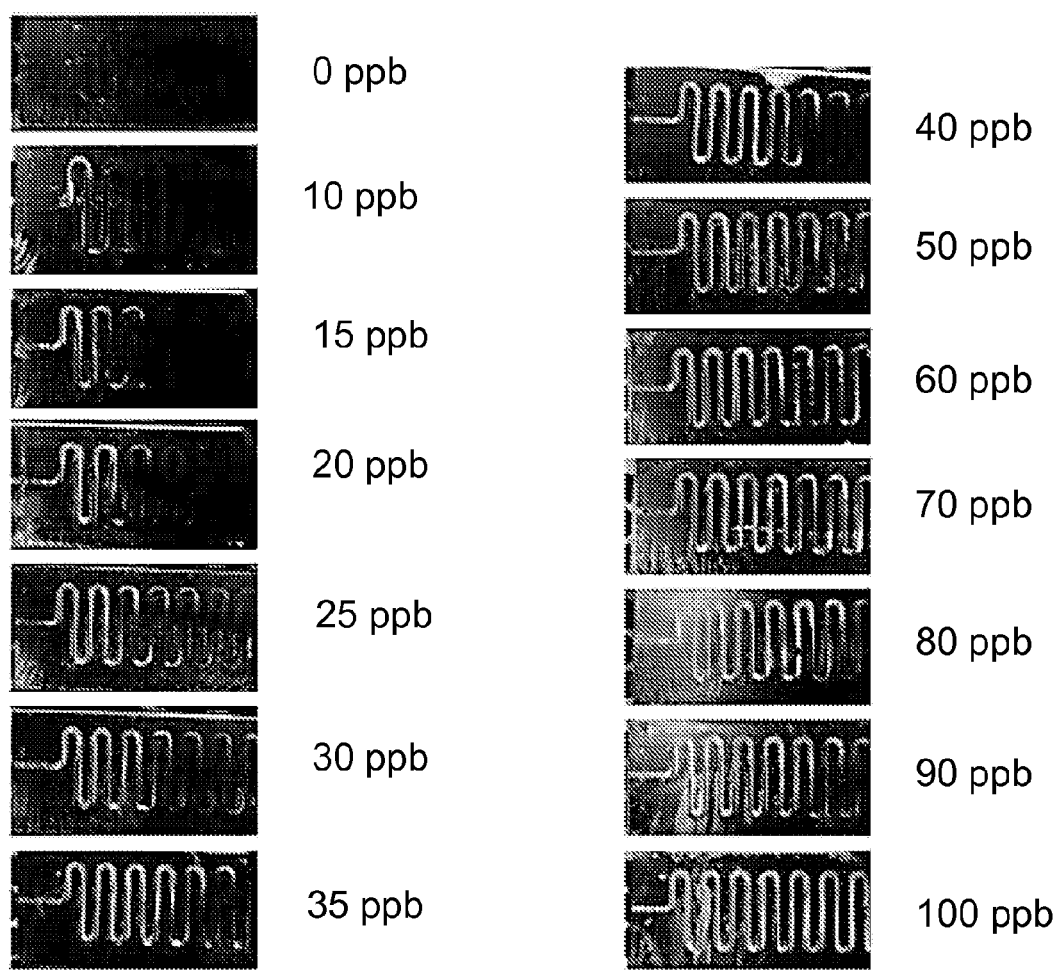
FIG. 31 shows images of a LC cell comprising a 4-aminothiophenol treated gold surface exposed to different concentrations of NO₂ and filled with a liquid crystal (MLC-2080 and MBBA at a 65 to 35 ratio). Concentrations of NO₂ tested were from 10 to 40 ppb in 5 ppb increments and 40 to 100 ppb in 10 ppb increments.

Test conditions were standard (see above) except that all $NO_2$ concentrations were equilibrated overnight and a 35% MBBA/65% MLC-2080 liquid crystal mixture was used. Concentrations of $NO_2$ tested were from 10 to 40 ppb in 5 ppb increments and 40 to 100 ppb in 10 ppb increments. Controls were 0 ppb $NO_2$ and pure nitrogen. The LC cells were exposed to different concentrations of $NO_2$, imaged (FIG. 31), and analyzed by measuring the total distance of continuous LC disruption. The measurement of the length of LC disruption was performed using software, e.g., by overlaying the image with a technical drawing of the channel marked with hash marks in millimeter increments. The extent of continuous LC disruption in the cells was matched with the drawing to determine the length of the phase changed path.

Figure 32:
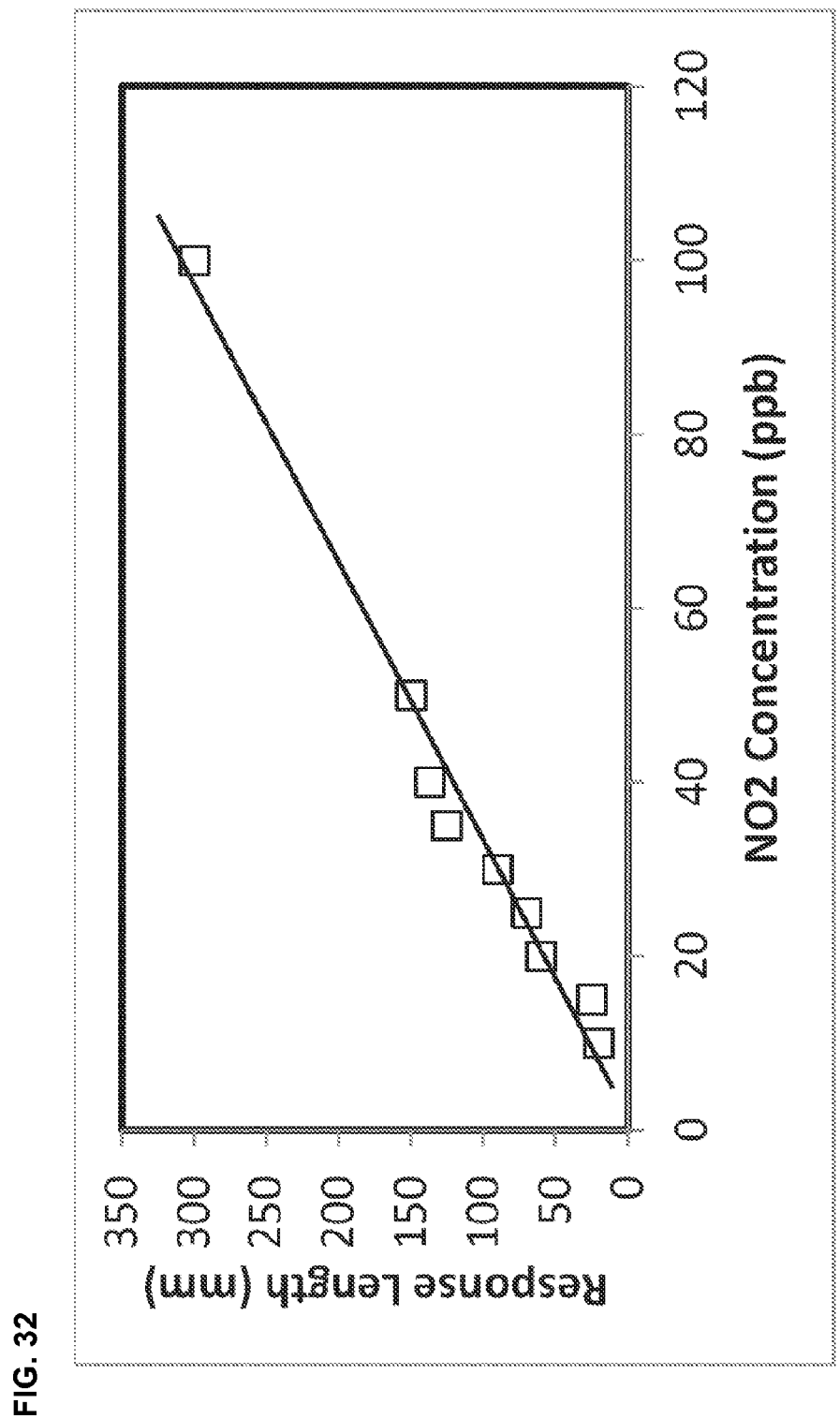
FIG. 32 shows a plot of data collected from analyzing the series of images shown in FIG. 31.

The results show that low amounts of $NO_2$ (e.g., ppb $NO_2$) are detected. A linear relationship exists between the $NO_2$ concentration and the length of the bright channel on the surface functionalized with ATP (FIG. 32).

Conclusions

In sum, these experiments demonstrate that ATP functionalized surfaces promote a homeotropic alignment of MBBA and a MBBA/MLC-2080 mixture of up to 80% of the MLC component. The time it takes for homeotropic alignment increases with an increase in the MLC concentration and decreases with an increase in incubation temperature. The homeotropic alignment can be obtained with an ATP surface alone without a need for a top OTS treated surface. The ATP functionalized surfaces, when exposed to $NO_2$, promote planar alignment. The change in the ATP surface was verified by FTIR in the form of a decrease in the peak intensities corresponding to the C—C and N—H stretches. A micro fluidic channel provides a method to quantify the response to $NO_2$ by measuring the length of the reacted path of the channel as reported in the form of the planar alignment of the LC. A higher flow rate combined with the MLC-MBBA mixture detected 10 ppb $NO_2$ at high humidity with 2 minutes of exposure.

Example 8

Identification of Surface Composition for Organic Vapor Detection Using Liquid Crystals During the development of embodiments of the technology provided herein, experiments were conducted to identify surface combinations for detecting VOC (e.g., toluene vapor) with a liquid crystal (LC). In particular, data were collected from testing combinations of a substrate and a liquid crystal suitable for determining an unknown concentration of toluene in the vapor phase. Several physical characteristics of the LC were monitored as indicators of VOC concentration, including LC phase transition, LC orientation change induced by change in the structure of polymer film due to swelling, and dissolution of toluene-soluble materials into the LC to initiate LC orientation change. Although particular experiments described herein are focused on toluene detection, similar embodiments comprising combinations of substrate and LC are appropriate for detecting other volatile organic compounds.

The experiments used LC materials that comprised rod-shaped organic molecules such as cyano-biphenyls (e.g., 5CB (4-cyano-4'-pentylbiphenyl) and E7 (a liquid crystal mixture comprising several cyanobiphenyls with long aliphatic tails). These molecules form condensed phases that possess crystal-like long range orientational ordering but lack positional ordering. The long-range ordering of molecules within the LC gives rise to anisotropic optical properties that result in a bright or dark appearance of the LC when viewed between crossed polarizers with a backlight source. Experiments were performed to confirm that toluene vapor causes a change in the polymer surface supporting a thin film of LC, e.g., due to polymer swelling or due to dissolution of the polymer surface material into the LC exposed to toluene. Both these phenomena induce a change in the LC orientation on the surface that can be easily detected by monitoring a change in incident light intensity. For example, absorption of toluene directly into the LC phase disrupts the long-range order of the LC, thus giving rise to a phase transition to an isotropic material and producing distinct changes in the optical appearance of the LC (see, e.g., E. J. Poziomek, T. J. Novak, and R. A. MacKay (1973), "Use of liquid crystals as vapor detectors", *Mol. Cryst. Liq. Cryst.* 27: 175-185).

FIG. 33 shows the basic principle of toluene detection using LC phase transition. A sensor comprising LC supported on a substrate with polymeric micropillars on a glass substrate initially appears bright (FIG. 33B, left). Upon exposure to toluene vapor, the LC material undergoes a phase transition and the sensor appears dark (FIG. 33B, right). The pre- and post-exposure appearance of the LC sensor depends on the surface upon which the LC is deposited. For example, a LC supported on glass substrate with polymeric micropillars (e.g., FIG. 33) initially appears bright and turns darker upon exposure to toluene while LC supported on a polymer or other materials spin coated on a glass substrate (e.g., as disclosed below) initially appears dark and becomes brighter as toluene causes a change in LC orientation due to polymer swelling or due to a change in the original surface.

LC Phase Transition

LC phases form as a consequence of intermolecular interactions that stabilize the long range orientational ordering of molecules within the LC phases. These interactions can vary substantially (e.g., arising from dipolar or steric interactions, dispersion forces, or hydrogen bonding) and depend on the structure of the molecules comprising the LC.

When the LC material is exposed to an organic vapor analyte such as toluene, the analyte partitions from the vapor into the LC and thereby perturbs the LC ordering, thus providing a measurable property of the sensor's response. As such, the extent of the perturbation induced by the analyte in the LC depends on the analyte-LC interactions, which will be influenced by factors such as relative polarities, polarizability, and hydrogen bond-donor/acceptor properties of the LC and analyte (see, e.g., S. J. Patrash and E. T. Zellers (1994), "Investigations of nematic liquid crystals as surface acoustic wave sensor coatings for discrimination between isomeric aromatic organic vapors", *Analytica Chimica Acta* 288: 167-177). Perturbation also depends on the shape (rod-like or planar) of the analyte. For example, arene-arene interactions between substituted aromatic solutes (dopants) and an aromatic liquid crystal such as 4'-pentyloxy-4-cyanobiphenyl (5OCB) induce perturbations in the bulk properties of the liquid crystal phase (V. E. Williams and R. P. Lemieux (1998), "Role of dispersion and electrostatic forces on solute-solvent interactions in a nematic liquid crystal phase", *J. Am. Chem. Soc.* 120: 11311-11315). As such, experiments were conducted to confirm that introducing an aromatic dopant (e.g., a VOC such as toluene) into the aromatic LC host (e.g., 5CB) causes a shift in the nematic-isotropic transition temperature that is a function of dopant-host interactions.

During the development of embodiments of the technology provided, experiments were performed to evaluate two different LCs having different physical and chemical properties and to determine their effectiveness for detecting toluene and other organic vapors. The sensors fabricated for these experiments comprised a micrometer-thick film of LC (5CB or E7) supported on a glass substrate decorated with polymeric micro-pillars (5 µm tall, 10 µm diameter, 20 µm center-to-center spacing). The micropillars are used to form mechanically robust thin films of the LC. The sensors were exposed to toluene or other organic vapor using an in-house gas exposure system schematically shown in FIG. 40. The exposure system consists of a gas delivery system (mass flow controllers, gas dilution system, etc.) and an optical image capture system (diffuse light source, CCD camera, polarizers, etc.). The saturated vapor of the target analyte was generated by bubbling $N_2$ gas through the liquid analyte. The saturated vapor analyte is then diluted at an appropriate ratio to generate the desired concentration before delivering it to the exposure chamber that houses the optical cells (sensor) prepared with the combination of substrate and LC. This gas delivery system was used to deliver a range of gases at various concentrations from the ppb to the ppm range. The sensors are placed inside an exposure chamber that is connected to the gas delivery system and flanked by two crossed polarizers. The chamber is placed between a CCD camera and a diffuse light source for real-time quantitative measurement of the optical change in the sensor.

Figure 41:
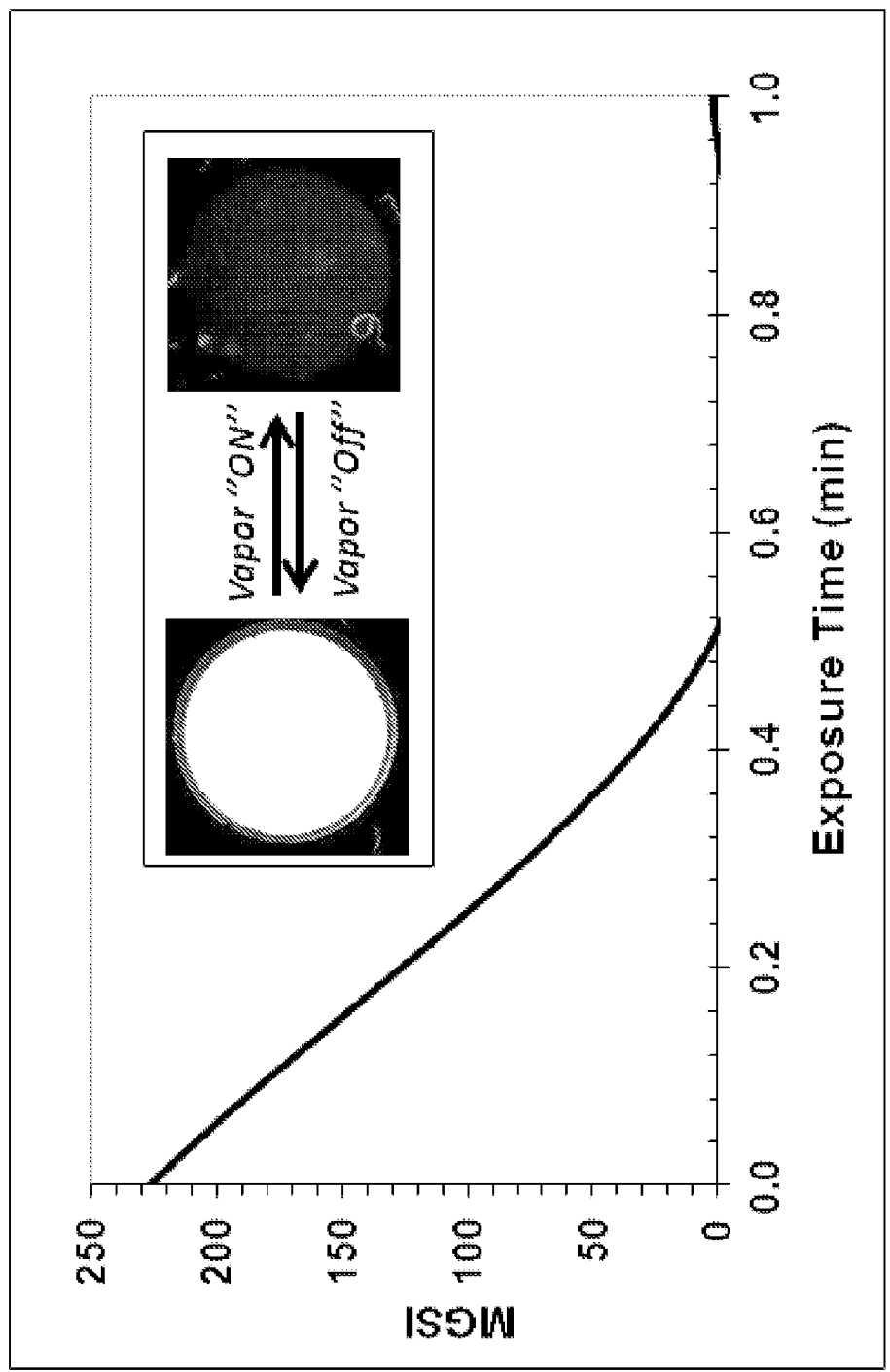
FIG. 41 is a plot showing the response of a LC sensor exposed to 5000 ppm toluene. The light intensity transmitted through the sensor between crossed polarizers (mean gray scale intensity-MGSI) was measured as a function of exposure time. The inset shows the visual appearance of the sensor between crossed polarizers before (bright) and after (dark) the vapor exposure. The sensor reverted back to initial appearance immediately after the toluene supply was ceased.

Prior to exposure to toluene or other vapors, the LC possesses a bright appearance when viewed through crossed polarizers with a backlight source. When the sensor was exposed to a known concentration of the targeted analyte, the analyte diffuses into the LC film and lowers the isotropic transition to approximately room temperature. This exposure induces a nematic-to-isotropic phase transition when a threshold concentration of analyte is reached (e.g., see FIG. 33). The phase transition in the LC causes a striking change in the optical appearance of the sensor. FIG. 41 shows a LC sensor (5CB) that was exposed to 5000 ppm toluene vapor. Similar LC sensors exposed to either dry (RH 0%) or humid (RH 95%) nitrogen alone didn't show any detectable changes. The toluene-induced changes of the LC are reversible—removing the vapor supply restores the original bright appearance of the LC film. The sensor responses to toluene and other organic solvents are summarized in Table 3.

TABLE 3

Organic solvent concentrations required to induce a phase transition in two different LCs (5CB and E7)

| analyte | 5CB concentration | E7 concentration |
|---|---|---|
| benzene | no change up to 20,000 ppm | NA |
| toluene | 5000 ppm | 11,000 ppm |
| m-xylene | 1500 ppm | NA |
| nitrobenzene | NA | 200 ppm |
| hexanes | no change up to 10,000 ppm | NA |
| isopropyl alcohol | 7500 ppm | NA |
| formic acid | 20,000 ppm | NA |
| methanol | 80,000 ppm | NA |

The data in Table 3 shows the relative sensitivity of LC sensors towards different organic solvents. These data suggest that the LC sensors made with 5CB and/or E7 are relatively more sensitive to aromatic solvents than non-aromatics (except for benzene). This is perhaps due to favorable π-π interactions between aromatic solvents and cyanobiphenyl LCs. The data in Table 3 also indicated that 5CB was more sensitive than E7 due to its lower nematic-isotropic transition temperature.

The sensor response discussed above requires a very high concentration of toluene to yield a visual change. A higher sensitivity can be obtained by; i) measuring the vapor response closer to the LC isotropic transition temperature, ii) choosing LCs with a lower isotropic transition temperature, and iii) using a sensitive instrument that will detect the signal (e.g., the optical properties) prior to the formation of isotropic phase.

Polymer Based Detection

Aromatic hydrocarbons (e.g., toluene) are known to swell various polymers. This effect is particularly pronounced for polymers of vinyl and styrene moieties (see, e.g., P. Muller-buschbaum, et al. (2006), "Fast swelling kinetics of thin polystyrene films", *Physica B*, 385-386, 703-705; B. Pejcic, et al (2007), "Environmental monitoring of hydrocarbons; A chemical sensor perspective", *Env. Sol & Technol.* 4(18); 6333-6342). LC orientation on a surface is extremely sensitive to the physical and chemical changes that occur at the LC-surface interface, thus the swelling property of polymers surface provides a basis for developing LC-based toluene sensors. Several polymers were identified (Table 4) based on the knowledge that these polymers swell upon toluene exposure.

TABLE 4

Exemplary polymers

| Structure | Polymer | Properties |
|---|---|---|
| 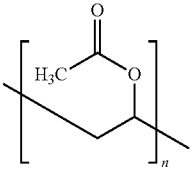 | Poly(vinyl acetate) [PVAc]: | Average MW ~100,000; transition temp: Tg: 30° C. |
| 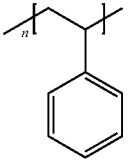 | Polystyrene [PS] | Average Mw ~280,000; transition temp: Tg: 100° C. |
| 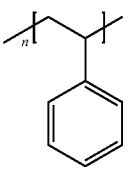 | Polystyrene [Low-MW PS] | Average MW ~9500; transition temp: NA |
| 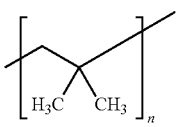 | Polyisobutylene [PiB] | Average MW ~500,000; transition temp: Tg: −64° C. |

TABLE 4-continued

Exemplary polymers

| Structure | Polymer | Properties |
|---|---|---|
| (structure with CF₃, HO, F₃C, Si, CF₃, CH, CF₃ groups) | SC-F103 (Seacoast Science Inc.) | NA |

The selected polymers (Table 4) were screened for their activity with toluene (e.g., at concentrations in the range of 1000 s of ppm) using liquid crystal optical cell by pairing two glass surfaces to support a thin film of LC. The polymers were deposited onto the clean glass surface by spin coating. The detection of the polymer surface response to the toluene vapor was conducted in two different ways. In the first one, a polymer coated surface was first exposed to a known concentration of toluene vapor followed by measuring the intensity of light passing through an optical cell made by combining the exposed polymer-coated surface, LC (E7), and an OTS-coated glass slide. The intensity of light passing through these optical cells was measured by using a polarized microscope equipped with crossed polarizers and a backlight source. A change of light intensity transmitted through the cell prepared with the exposed surface due a LC orientational change was compared with a cell made with an unexposed surface. In the second method, an optical cell that was made by a combination of a polymer-coated surface, LC (E7), and an OTS-coated glass slide was monitored for a change in the light intensity transmitted through the cell placed between crossed polarizers. Mean gray-scale intensity (MGSI) was measured as a function of exposure time using a CCD camera and backlight source.

Polystyrene

The liquid crystal alignment properties of the polystyrene coated films were tested with glass-OTS sandwich optical cells. Glass slides (Fisher finest: plain premium microscope slides) were thoroughly flushed with nitrogen ($N_2$) and then rinsed thoroughly with ethanol and acetone. Slides were initially dried with $N_2$ followed by heating at 100° C. for 30 minutes. Slides were further UV-ozone cleaned for 5 minutes. All glass slides used in this study were cleaned with this same procedure. The glass slides (1"×1") were coated with 100 μl of 15 mg/ml stock solution of the polymer polystyrene dissolved in toluene. In this sandwich optical cell, an OTS-coated glass slide and a polystyrene-coated glass slide were aligned facing each other. The two surfaces were kept apart by a spacer having a thickness of ~30 μm. A 10-μl drop of LC (E7) in nematic phase was placed at the center of the polymer-coated glass piece, then the OTS-coated glass piece was put on top of it. The two surfaces, having a spacer and LC in between them, were held together using binder clips. The LC optical cells were imaged using a polarizing optical microscope. A homogeneous alignment of E7 on the polystyrene was induced by rubbing the polymer coated surface with a velvet cloth in one direction for five times before LC addition. Although the exact reason for this rubbing-induced LC alignment is not yet understood clearly, the technique is used very often to align LCs on different polymer surfaces (Wu, et al. (1996) "Liquid-crystal alignment of rubbed polyimide films: A microscopic investigation", Applied Physics B: Lasers and Optic, 62(6), 613-618).

Figure 42:
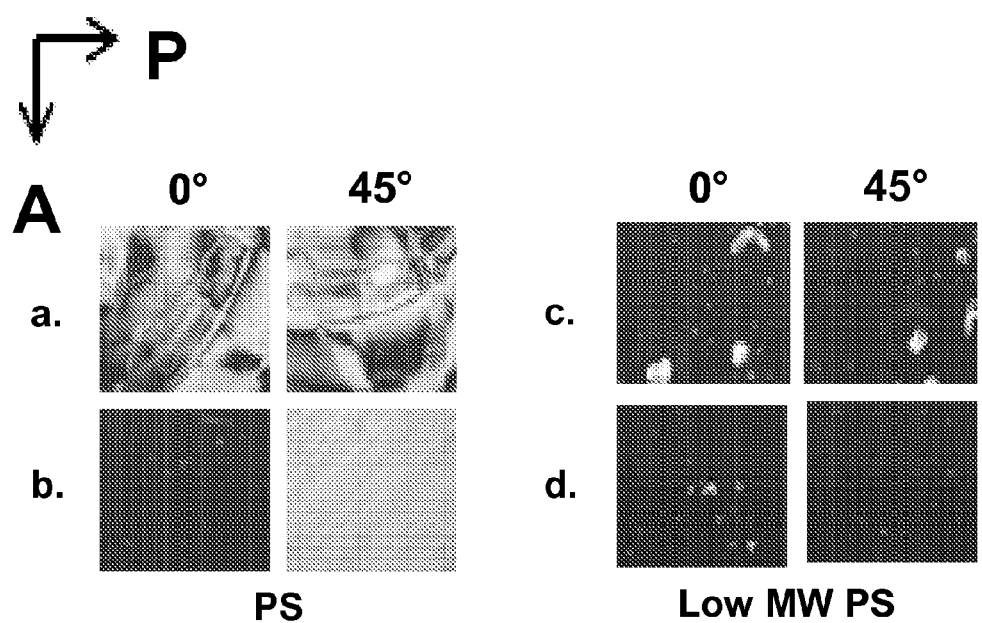
FIG. 42 shows optical images of LC cells prepared with polystyrene (PS) and low molecular weight PS (low MW PS) polymer coated on a glass surface by pairing with Tridecafluoro-1,1,2,2-tetrahydrooctylkrichlorosilane (OTS) coated substrates. The polymer coated substrates were un-rubbed (a and c) and rubbed (b and d). These images were taken with the LC cells between crossed polarizers (A: analyzer and P: polarizer) with the rubbing direction oriented at 0° (left) and 45° (right) with respect to the crossed polarizers In FIG. 43.

FIG. 42 shows microscope images of cells prepared with the rubbed or unrubbed polystyrene films and E7 viewed at different orientations of the cell with respect to the cross polarizers. FIG. 42b shows a change in light intensity (e.g., from dark to bright) through the optical cell made with rubbed polystyrene film when the cell was positioned at 0 and 45 degrees with respect to the crossed polarizers. This change indicates a homogeneous planar alignment of the LC on the rubbed polystyrene surface. Similar rubbing-induced homogeneous alignment was observed with PVAc, PiB, and SC-F103. Quite unexpectedly, the surface prepared with low MW PS from a 15 mg/ml toluene stock solution showed homeotropic alignment without any rubbing (FIG. 42c). As this surface aligned LC (E7) homeotropically with or without rubbing they were not further tested with toluene. However, the same low MW PS was used to test the dewetting induced orientation of LC (see below).

Figure 43:
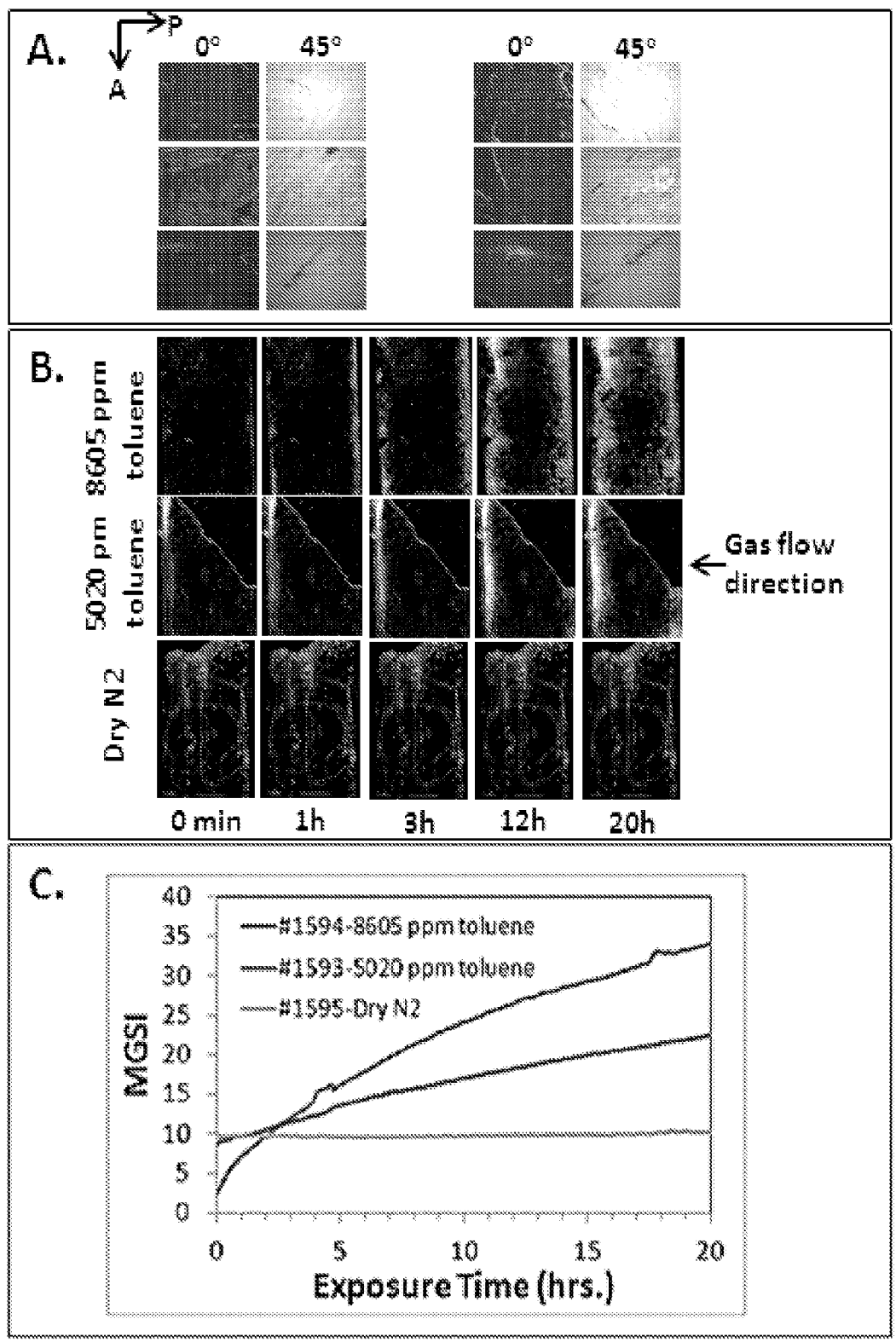
FIG. 43A shows optical images of LC sandwich cells prepared with rubbed polystyrene (PS) and OTS coated substrates "before" (left) and "after" (right) 20 hours of toluene exposure. The sandwich cells were exposed to 8605 ppm (top), 5020 ppm (middle), and 0 ppm (bottom) toluene, respectively. Optical images were taken with the rubbing direction at 0° (left) and 45° (right) with respect to the crossed polarizers.
FIG. 43B shows the raw images of LC sandwich cells that were collected at different time intervals while exposed to 8605 ppm (top), 5020 ppm (middle), and 0 ppm (bottom) toluene, respectively.
FIG. 43C shows the light intensity transmitted through the LC sandwich cells between crossed polarizers (mean gray scale intensity-MGSI) measured as a function of exposure time.

For toluene exposure studies, a series of optical cells were prepared using mechanically rubbed PS substrates coated on glass, an OTS-coated glass slide, and E7. The cells were exposed to nitrogen or toluene and images were collected at a regular time interval using the experimental set up shown in FIG. 40. The results of exposure experiments are summarized in FIG. 43. The data in FIG. 43a show that there was no change in the overall planar alignment in the LC cell due to toluene exposure when viewed under the microscope. However, the data in FIGS. 43b and 43c show a definitive change in the LC cells due to toluene exposure when compared to the cell exposed to nitrogen alone. A similar change of a smaller magnitude was observed when the LC cell was exposed to 2900 ppm toluene vapor.

In another test, a PS coated surface was used where the polymer surface was first exposed to a known concentration of toluene vapor followed by measuring the intensity of light passing through an optical cell made by combining the exposed polymer coated surface, LC (E7), and an OTS coated glass slide. A series of glass substrates were coated with PS films, the surfaces were mechanically rubbed, and then exposed to toluene. After toluene exposure, the surfaces were overlaid with LC (E7) to prepare an optical cell for measurement. A sandwich cell prepared in this manner was exposed to 5020 ppm toluene for 1 hour and was observed to have the same planar alignment as the cell made with unexposed surfaces. A similar cell made with a surface exposed to saturated toluene vapor initially showed a random alignment but slowly changed to a planar alignment. These observations suggest perhaps the change due to toluene exposure on rubbed PS surface is transient and quickly disappears as toluene supply was ceased.

Poly(Vinyl Acetate)

Figure 44:
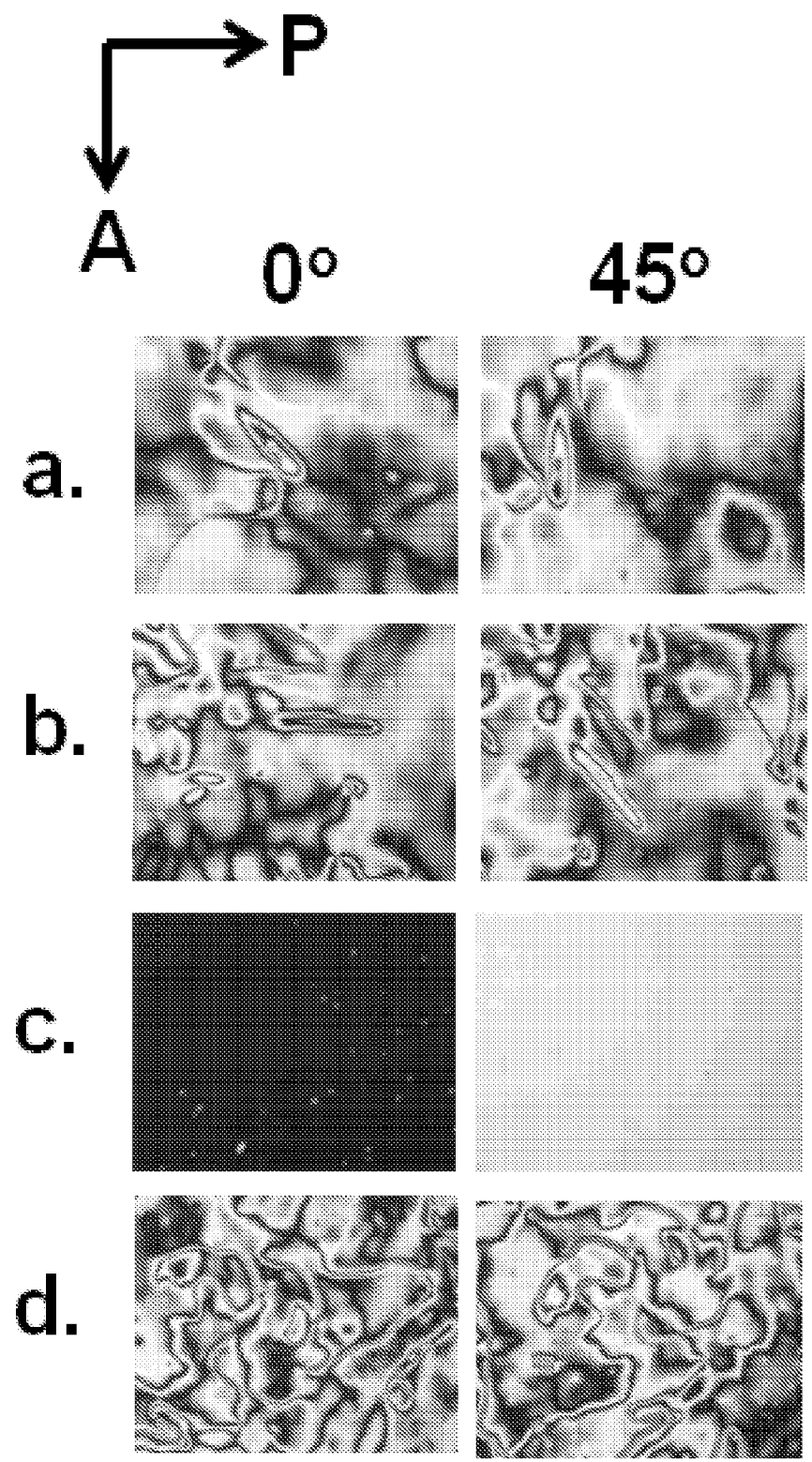
FIG. 44 shows optical images of LC cells prepared with poly(vinyl)acetate (PVAc) and OTS coated substrates. The PVAc coated substrates were (a) un-rubbed & unexposed, (b) un-rubbed & exposed, (c) rubbed & unexposed, and (d) rubbed & exposed. 28,680 ppm toluene was used for exposure prior to cell fabrication. Optical images were taken with rubbing direction at 0° and 45° with respect to crossed polarizers.

A series of glass substrates were coated with poly(vinyl acetate) [PVAc] films; then, the surfaces were mechanically rubbed, exposed to nitrogen or toluene, and then overlaid with LC (E7) to prepare an optical cell for measurement. Clean glass slides (1"×1") were coated with 100 µl of 16 mg/ml stock solution of the PVAc polymer in a toluene solution. It was observed that a surface coated with PVAc promoted a random alignment of LC. When this surface was exposed to a saturated vapor of toluene (e.g., at 28,680 ppm) followed by LC overlay no change was observed in the LC alignment. A homogeneous alignment of E7 on the PVAc-coated films was induced by rubbing the film surface with a piece of velvet cloth in one direction five times (e.g., as used for PS in the experiments described above). FIG. 44 shows images of LC cells prepared with PVAc-coated surfaces viewed at different azimuthal orientations of the rubbing directions with respect to the cross polarizers.

Figure 45:
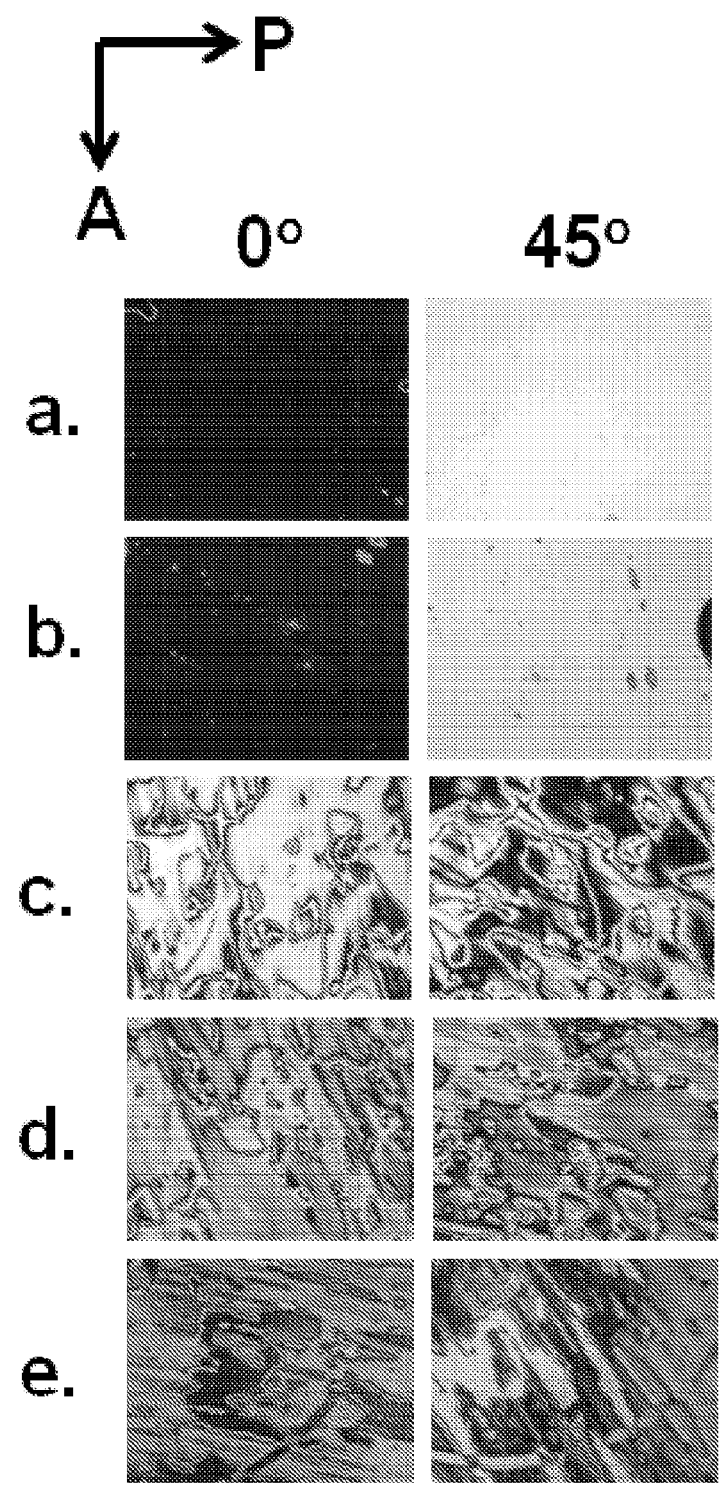
FIG. 45 shows optical images of LC cells prepared with rubbed PVAc and OTS coated substrates. The PVAc coated substrates were rubbed five times or only once and exposed to toluene prior to cell fabrication. (a) rubbed (5 times) & exposed (8605 ppm), (b) rubbed (1 time) & exposed (0 ppm), (c) rubbed (1 time) & exposed (8605 ppm), (d) rubbed (1 time) & exposed (5020 ppm), and (e) rubbed (1 time) & exposed (2868 ppm). Optical images were taken with rubbing direction at 0° and 45° with respect to crossed polarizers.

The data in FIG. 44 showed that a rubbed PVAc surface yielded a change in the LC alignment upon exposure to saturated toluene vapor (28,680 ppm). Unlike rubbed PS-coated surfaces, the random LC alignment did not revert to a planar alignment quickly. A reduction in the toluene concentration to 8605 ppm did not result in any difference in the LC alignment when compared to an unexposed surface. To avoid LC addition after toluene exposure an optical cell was prepared with a rubbed PVAc coated surface, LC (E7), and an OTS coated glass slide. The cell was exposed to 8605 ppm toluene for 20 hours but no detectable difference was observed due to toluene exposure. To examine the effect of rubbing on the toluene response at sub-saturation concentrations, a series of PVAc-coated surfaces were prepared using less rubbing and exposure experiments were conducted with sub-saturated concentrations of toluene vapor. FIG. 45 shows images of LC cells viewed at different azimuthal orientations of the rubbing directions with respect to the cross polarizers. The data in FIG. 45 showed that by reducing the rubbing the sensitivity towards toluene was significantly enhanced. Initial experiments suggested that a thinner polymer coating (e.g., coating from a 5 mg/ml polymer stock solution) and minimum rubbing improve the sensitivity of toluene detection using rubbed polymer surfaces. The images in FIG. 45 showed a very large change in the transmitted light intensity through the optical cells upon exposure to 8600-2900 ppm toluene vapor.

SC-F103

Figure 46:
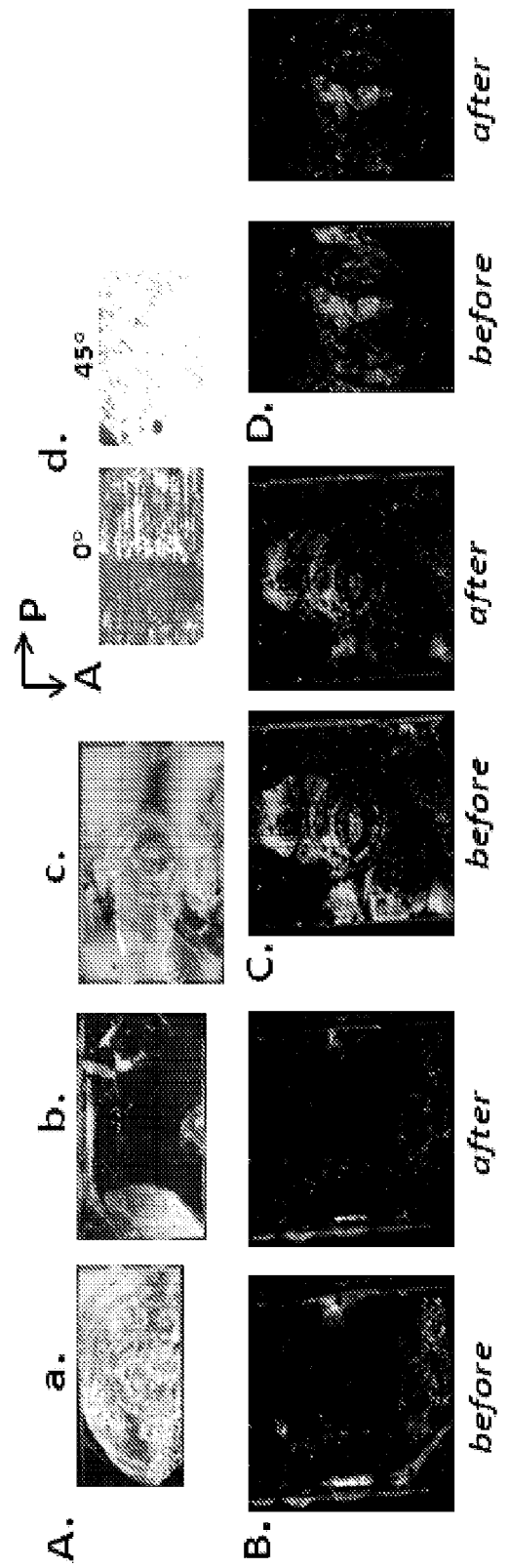
FIG. 46 shows images of LC(E7) alignment of the exposed and unexposed optical cells prepared using rubbed or unrubbed SC-F103 polymer (Seacoast Science Inc.) coated substrates. For rubbed polymer surfaces rubbing was done with a piece of velvet cloth rubbed one way for five times before LC addition. A) Images of unexposed sandwich cells made with different types of SC-F103 surfaces on glass, a) uncoated; b) unrubbed SC-F103; c) rubbed SC-F103; d) images of the rubbed SC-F103 cell taken with rubbing direction at 0° and 45° with respect to crossed polarizers. B) Images of a cell prepared with unrubbed SC-F103 coated surface before and after exposure to 5020 ppm toluene for 26 hours. Similar images were collected using the cells made with rubbed SC-F103 coated surface before and after 23 hours of exposure to C) 5020 ppm toluene and D) dry nitrogen, respectively.

SC-F103 is a hyperbranched fluoroalcohol polycarbosilane. Experiments were conducted to test SC-F103 in LC-based toluene detection. The polymer was spin coated on clean glass surfaces from a 16 mg/ml stock solution of 1:1 toluene and $CHCl_3$. Optical cells were then prepared with the polymer-coated surface and OTS as described before. Images of cells are shown in FIG. 46. As the glass surface was coated with the polymer, there was no visible indication that the polymer coating was formed on the glass. However, cells prepared with uncoated glass showed a different alignment pattern than the SC-F103 coated cells (FIG. 46A, a and b). This suggests the presence of a film of polymer after spin coating. Interestingly, the surface prepared with SC-F103 showed homeotropic alignment without any rubbing. This is similar to the observation made earlier with the cells prepared with low MW PS.

FIGS. 46B and 46C show images of SC-F103 cells before and after exposure to toluene. Only a small change was observed before and after exposure. However, a similar change (e.g., bright patches that turned darker upon exposure) was also observed when a similar SC-F103 cell was exposed to dry nitrogen alone. This change in part of the bright patch may arise as a result of the formation of LC-polymer homogeneous mixture over time to lower the phase transition temperature in LC.

Hydrocarbon Based Detection

Figure 47:
FIG. 47 shows long chain hydrocarbons tested in experiments described herein.
Figure 47:
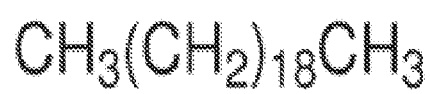
Figure 47:
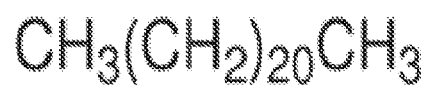
Figure 47:
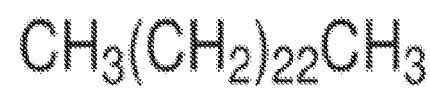

As the LC orientation is very sensitive to the surface composition it is likely that the dissolution of toluene-soluble materials coated onto the surface will initiate a change in the LC orientation. It was anticipated that the toluene solubility of materials coated as a thin film on a surface that is known to align LC in a pre-defined direction (e.g., rubbed polymer, OTS treated surface, etc.) would dewet the surface, thus locally exposing the underlying surface to the LC and leading to reorientation of the LC. Long chain aliphatic hydrocarbons (e.g., $C_{18}$ and higher) are solid at ambient temperature and possess a very high solubility (>100 mM) in toluene. Initially, four hydrocarbons as shown in FIG. 47 were chosen for these studies.

Figure 48:
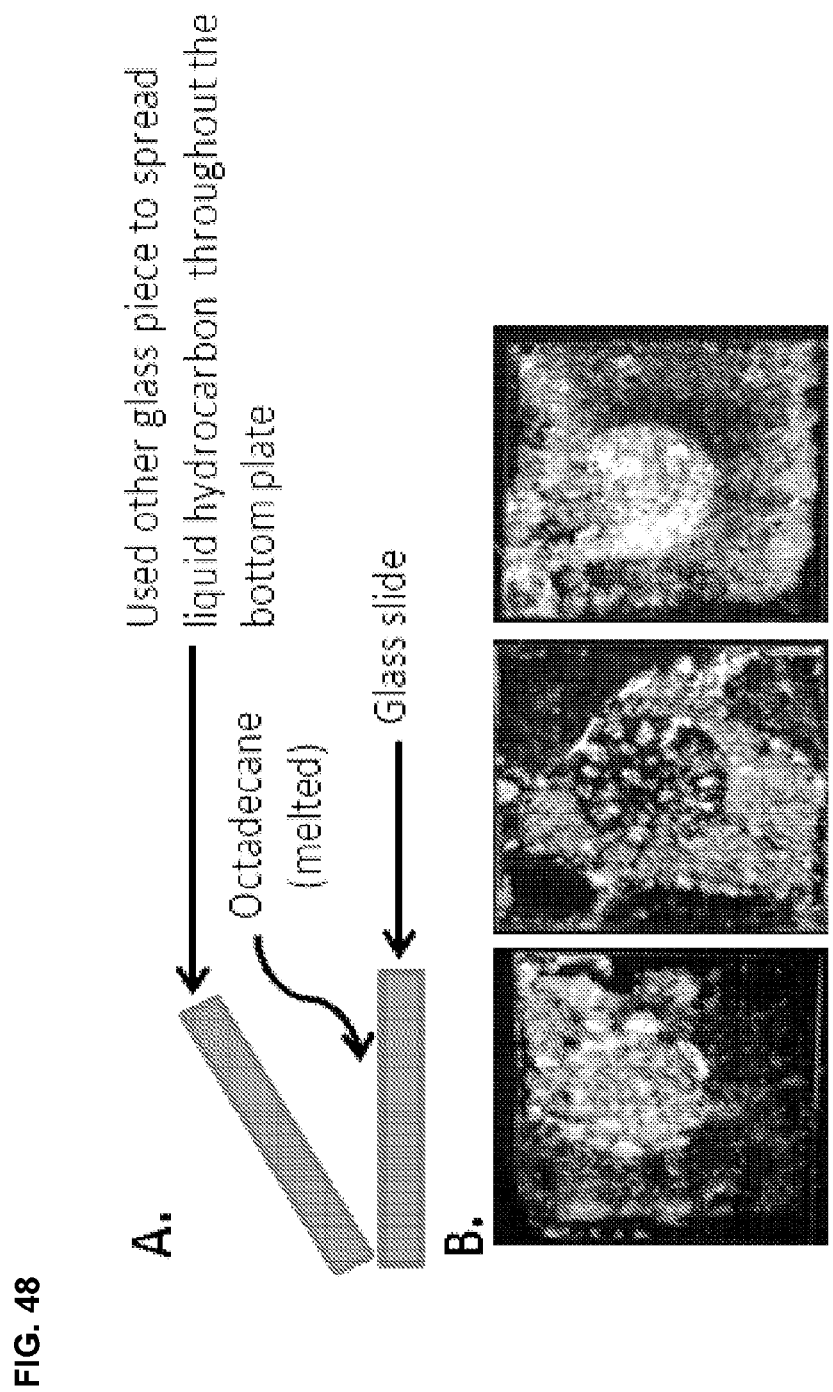
FIG. 48 shows in (A) a schematic for making a thin hydrocarbon film on a 3"×1" glass slide and in (B) the images of 1"×1" glass slides with LC (E7) coated on top of a hydrocarbon (C18) layer between crossed polarizers.

A glass piece was coated with the neat hydrocarbon for testing. Solid octadecane was first spread onto the glass piece (1"×3") with a spatula and then another glass piece was placed on it. The hydrocarbon sandwiched between the two glass pieces was heated to ~50° C. The melted octadecane spread into the cavity. The top glass slide was then dragged from one end to the other to spread the liquid on the base glass piece to form a thin film. Upon cooling, a white film was observed on the plate. The octadecane-coated glass surface was then cut into smaller 1"×1" pieces and E7 was spin coated on the hydrocarbon layer. Images are shown in FIG. 48.

Figure 40:
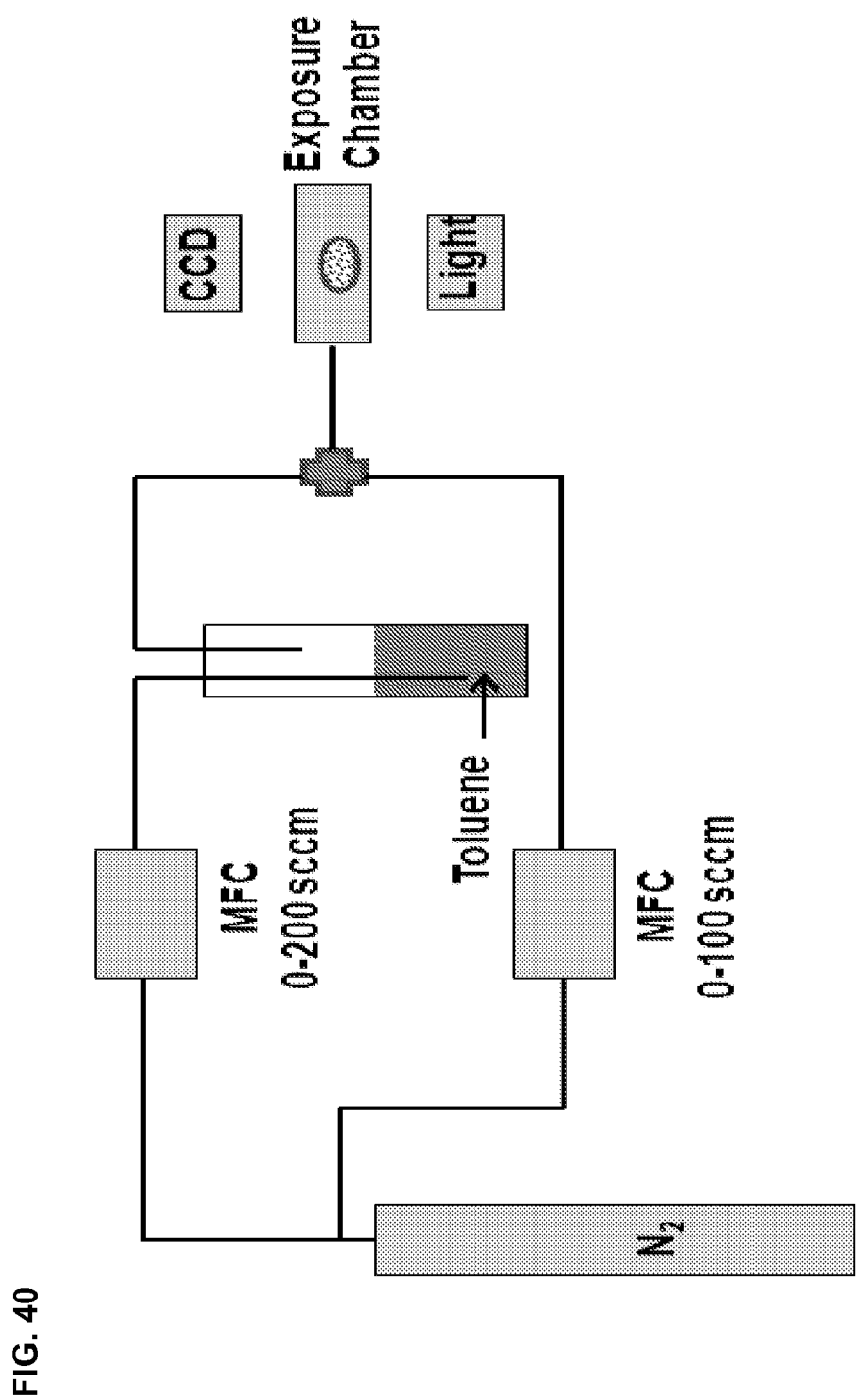
FIG. 40 is a schematic showing an experimental system for exposing sensors to VOC.
Figure 49:
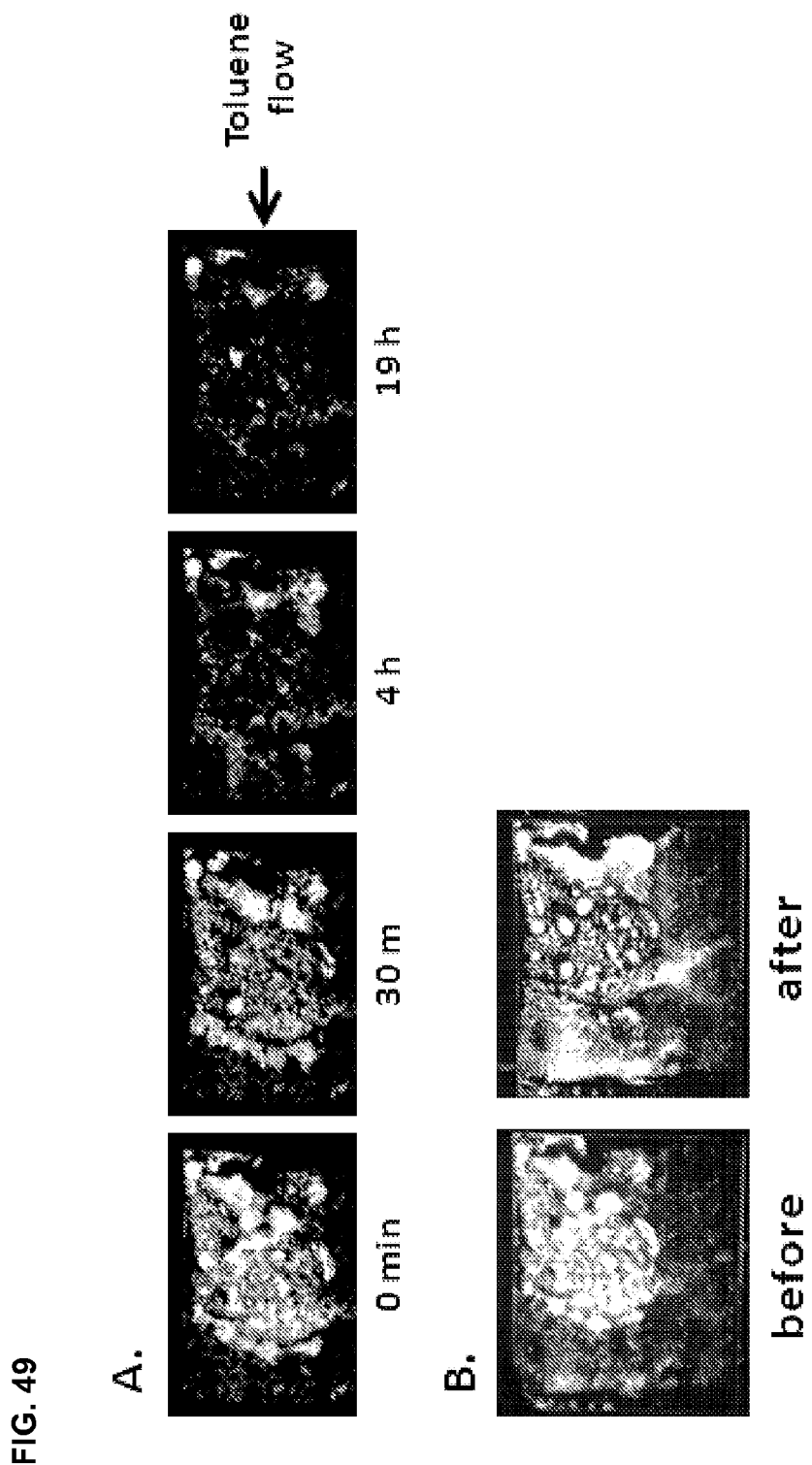
FIG. 49 shows (A) images of an LC sensor collected while exposed to 5020 ppm toluene vapor. (B) Images of the same sensor collected off line before and after 19 hours of toluene exposure.

One of the 1"×1" pieces with LC coated on a hydrocarbon layer was exposed to 5020 ppm toluene using the exposure system shown in FIG. 40. The result of this exposure experiment is shown in FIG. 49. The data shown in FIG. 49A indicated a change from bright to dark as exposure time increased. However, this change was transient, e.g., the exposed chip was gradually turned towards a brighter appearance as the toluene supply was ceased after 19 hours. Though the images acquired before exposure and after toluene exposure had been ceased for 19 hours (FIG. 49B) were not identical, the nature of the changes observed indicate an LC phase transition due to toluene exposure.

Figure 50:
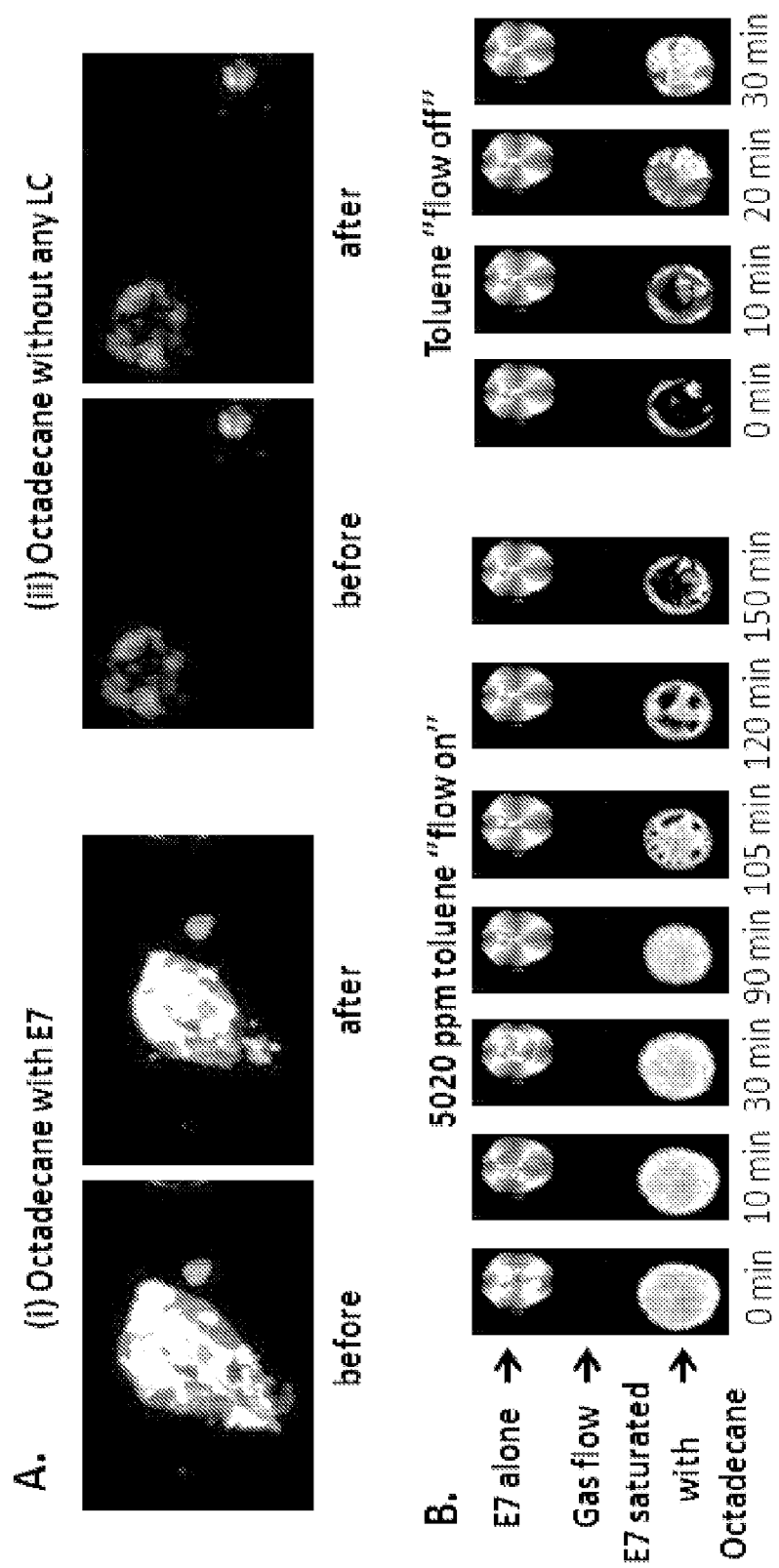
FIG. 50 shows images of A) a portion of the sandwich cells containing (i) octadecane and E7 and (ii) octadecane alone from 5 hours of 5020 ppm toluene exposure. B) 5020 ppm toluene exposure to the E7 and E7-octadecane mixture spotted on a glass piece.

To investigate the origin of this change, solid octadecane was deposited from its chloroform solution onto two OTS-coated glass slides and then paired with another OTS-coated piece to form optical cells. In one of the cells, the cavity between the OTS-coated pieces (2×35 µm=70 µm) was filled with E7 and the other cell was left untreated. Both of the cells were individually exposed to 5020 ppm toluene vapor and images were collected at a regular interval during a total period of 5 hours of exposure. The data from this exposure experiment are shown in FIG. 50A. The data in FIG. 50A(i) show that the areas where both LC and octadecane were present (the bright spots in the image) change to a darker appearance over time. However, the optical cell containing only octadecane spots (FIG. 50A(ii)) appear relatively less bright under similar conditions (FIG. 50A(i)) but undergoes no detectable changes upon 5020 ppm toluene exposure for 5 hours. This observation suggests the changes are associated where LC is in contact with the octadecane.

In another experiment, 10 µl of E7 and E7 mixed with octadecane were placed on a piece of glass piece to test the bulk properties of the octadecane-E7 mixture. The spotted glass piece was then placed inside the experimental chamber and exposed to 5020 ppm toluene for 2.5 hours and images were collected. At the end of toluene exposure the gas flow was turned off but the image collection was continued for another 0.5 hour. The data are shown in FIG. 50B. The data in FIG. 50B show that the dark appearance of the LC-octadecane mixture that resulted from 2.5 hours of 5020 ppm exposure begins to turn brighter quickly after the gas was turned off. Under the same conditions, the E7 spot remained unchanged throughout this 3-hour period indicating that the bright to dark transition associated with the E7-octadecane mixture is due to the lowering of the nematic to isotropic (N-I) phase transition temperature of the mixture. This lowering of the N-I transition temperature in E7 was the result of soluble octadencane in E7.

Figure 51:
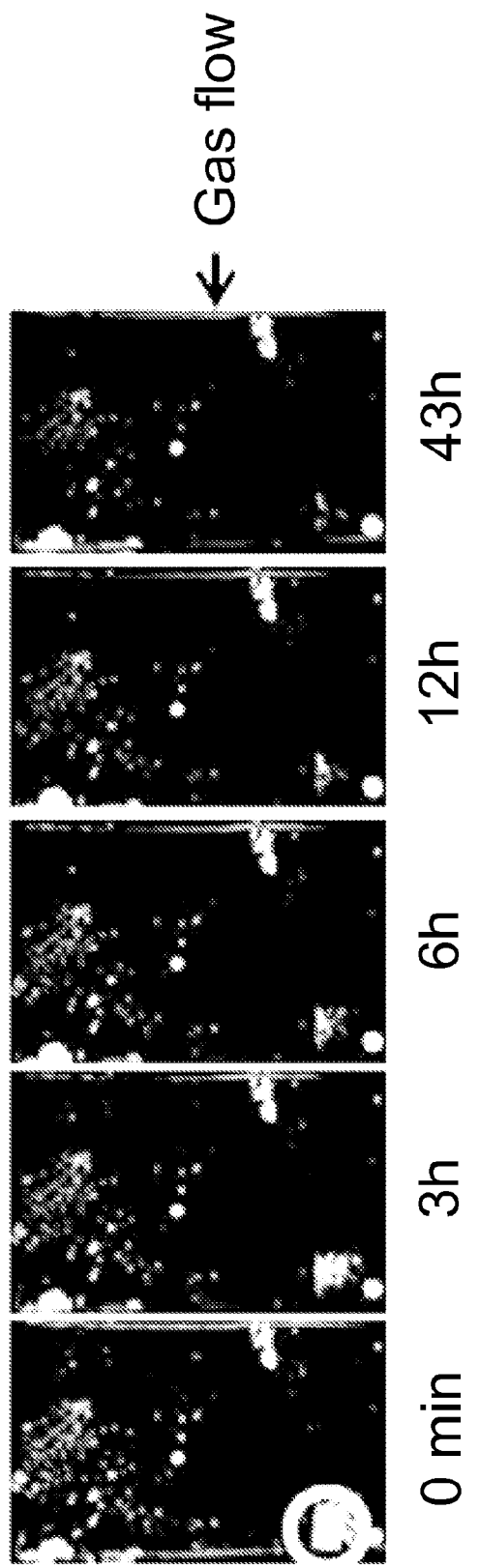
FIG. 51 shows images from experiments testing 5020 ppm toluene exposure to a sandwich cell prepared by pairing a substrate coated with C24 film and an OTS coated glass pieces. The gap between two substrates was filled with LC E7.

Another long chain hydrocarbon (tetracosane, C24) was also tested. An OTS-coated glass piece was first coated with the neat hydrocarbon following the similar procedure used in coating octadecane on glass (FIG. 48A). The tetracosane-coated surface was then cut into smaller pieces to make optical cells, paired with another uncoated OTS piece, and the cavity filled with LC (E7). The LC (E7) laid onto the hydrocarbon film sandwiched between two OTS pieces aligned LC homeotropic. However, the thickness of the hydrocarbon may not have been the same throughout the plate as suggested by the appearance of some bright patches that were observed in the cells. One such cell was exposed to 5020 ppm toluene for 43 hours (FIG. 51). The white patch under the yellow circle disappeared with long exposure to toluene. However, it started to reappear slowly as the cell was taken out of the exposure chamber indicating a phase transfer due to toluene exposure.

Summary

Experiments were conducted to test various LC films and LC alignments on polymer and other surfaces. The data provide an understanding of sensor substrate features and how they can be engineered to affect sensor response time for the detection of toluene. The LC phase transition offers a simple technique for the detection of toluene and other organic solvents. The detection threshold varies over a wide range of concentrations based on analyte characteristics and the LC used.

Polystyrene (PS) was identified as a suitable polymer for the detection of toluene using a change in LC orientation. It is contemplated that the technology will detect toluene in the range of from 50 ppm to 3000 ppm. The speed at which the sensors respond to toluene vapor can be controlled by fabricating sensors on polymer coated substrates with a defined thickness, controlled rubbing, and a cell configuration that allows unrestricted toluene flow. C18 and C24 hydrocarbons were tested to improve the sensitivity of toluene detection. These highly toluene-soluble hydrocarbons facilitate toluene detection by lowering the nematic-isotropic phase transition temperature of the LC used.

Example 9

Detection of Volatile Organic Compounds Using Polymer Dispersed Liquid Crystals

During the development of embodiment of the technology provided herein, experiments were performed to test feasibility of using a polymer dispersed liquid crystal (PDLC) system for detection of volatile organic compounds (e.g., toluene). The results from these preliminary experiments suggest that PDLCs detect VOCs such as toluene if the PDLCs are formed with a polymer that is known to adsorb VOCs. The sensitivity of detection depends on a number of parameters that influence the morphology of the PDLCs. Data collected show that toluene at 2000 ppm is detected using PDLCs prepared from LC E7 and polystyrene (PS) using solvent-induced phase separation. It is contemplated that detection will be more sensitive (e.g., detect lower amounts of VOC) with further optimization, e.g., optimizing parameters to improve the sensitivity of detection, and providing more precise PDLC morphology by better control of the fabrication process. To increase the dynamic range of detection, PDLCs were formed on rubbed polymer surfaces.

Background

Initial experiments with pure liquid crystals 5CB and E7 demonstrated a detection of ~5000 ppm and ~12,000 ppm, respectively (see Table 3). To improve the sensitivity of detection, a number of approaches have been discussed including confinement of LC in small cavities formed from polymeric materials that are known to adsorb toluene. The basic idea behind this approach relies on the fact that the LC confined inside a small cavity assumes some initial director configuration. Once this confined LC is exposed to VOC such as toluene, the polymer undergoes structural changes that will induce a change in the ordering of LC inside this cavity.

FIG. 34 shows a basic principle behind this approach of detection where a LC droplet is confined inside a polymer matrix that is known to adsorb the target VOC. The boundary condition is such that the orientation at the LC-polymer interface provides alignment of the LC in an orientation that is perpendicular to the interface. The polymer matrix is confined so that it can deform only along one direction. Upon exposure to the VOC, the polymer undergoes deformation that subsequently changes the shape of the LC droplet and the orientation of LC components. Different embodiments of the same basic principle are envisioned. One simple format that was tested made use of well-defined PDLC structures that deformed and/or changed upon exposure to toluene. Initial experiments with the PDLCs formed by mixing a UV-curable polymer (NOA-21) and E7 showed that the sensors respond to toluene but the response was not due to deformation of the polymer structure but was more related to the decrease in the nematic-isotropic transition temperature of the E7 as a result of dissolution of uncured monomer into the LC E7. Since NOA-21 forms a strong polymer upon exposure to UV light the polymer matrix did not deform upon exposure to toluene. However, the uncured monomers dissolved in the LC were sufficient to lower the phase transition temperature of E7 from ~65° C. to a temperature close to the phase transition temperature of 5CB (~35° C.). As such, the sensors demonstrated a response to ~5000 ppm toluene that was similar to the response of a pure 5CB sensor. In the experiments described below, PDLCs were formed using polymers that were known to dissolve in toluene (e.g., polymers such as polystyrene and polyvinylacetate that are known to adsorb toluene) to prepare PDLCs with the anticipation that they would deform upon exposure to toluene. Embodiments are envisioned in which PDLC is prepared in a strained configuration so that exposure to toluene will release the strained energy for sensitive detection of toluene.

High Molecular Weight Polystyrene

Figure 52:
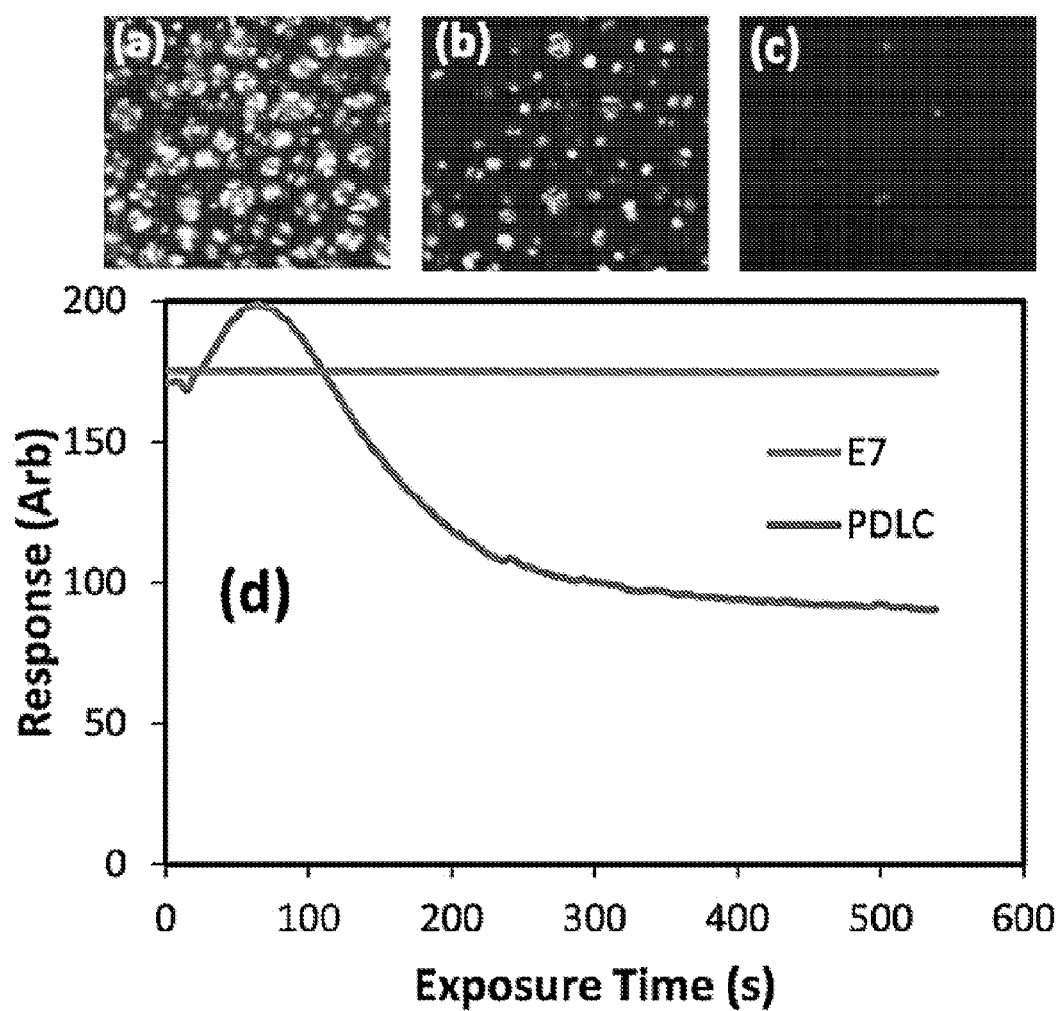
FIG. 52 shows the detection of toluene vapor using PDLCs. (a) to (c) Microscopic pictures of PDLCs (a) before, (b) during, and (c) after exposure to a high concentration of toluene. (d) The optical response of PDLC sensors to 8600 ppm toluene in comparison to pure E7 sensors.

A polystyrene (PS) solution of approximately 2% by weight in toluene was prepared by mixing PS (average MW 280,000, Sigma Aldrich #182427) in toluene, then vortexing and heating the solution to 70° C. in an oven. Similarly, a ~2% E7 solution was prepared by dissolving LC E7 in toluene and vortexing the solution. These two stock solutions were used to prepare PDLCs with different E7:PS ratios. Using the stock solutions, the PS:E7 solutions were mixed at a 1:2 ratio. Glass slides were coated with OTS with masked 7-mm diameter areas. These areas were cleaned and then 50 µl of the 1:2 PS:E7 mixture was deposited and the solvent was allowed to evaporate slowly by covering with a petri dish. After complete solvent evaporation, the LC separates from the polymer matrix forming well-defined droplets (FIG. 52a). These droplets scatter light and appear bright when viewed between crossed polarizers. When these droplets were exposed to toluene vapor generated by bubbling dry $N_2$ gas through liquid toluene (inside an exposure chamber at a flow rate of 200 ml/min using set up similar to FIG. 40) the toluene vapor thus produced induced phase transition in E7 and the PDLC film appeared dark (FIG. 52c). After establishing that the PDLC film gives a response to toluene vapor at a high concentration using an optical microscope, these sensors were then exposed to ~8600 ppm toluene vapor using the exposure system similar to FIG. 40. The optical response behavior of these sensors to toluene vapor is shown in FIG. 52d. The results indicate that the PDLC sensors are more sensitive to toluene vapor than pure E7 sensors. These findings suggest that by incorporating the polymer into the LC materials the partition of toluene vapor into the LC film is enhanced and therefore improves the sensitivity. However, the sensitivity of detection was suboptimal. Additionally, the PDLCs formed using this approach yielded spherical droplets without any stored elastic strain.

Low Molecular Weight Polystyrene

Lower molecular weight PS rapidly phase separate forming well-defined PDLCs. Polystyrene with a lower molecular weight (e.g., MW 20,000, Sigma Aldrich #327743) was tested to demonstrate the feasibility of detection of toluene using PDLCs. PDLC droplet were formed on 0.8 cm×0.8 cm glass substrates. The glass substrates were thoroughly rinsed with acetone and ethanol then dried in a stream of nitrogen. These substrates were subjected to a 2 minutes UV ozone treatment. PDLC droplets were formed on these substrates by depositing 15 microliter of 1:2 (PS: E7) mixture prepared by dissolving both PS and E7 in toluene forming 2% mixtures. To generate the PDLCs with ~2 micrometer diameter, the solvent was allowed to evaporate slowly. The size of the PDLC droplets was confirmed by using polarizing optical microscope.

Results

Effect of Thermal Annealing on the Morphology

Figure 53:
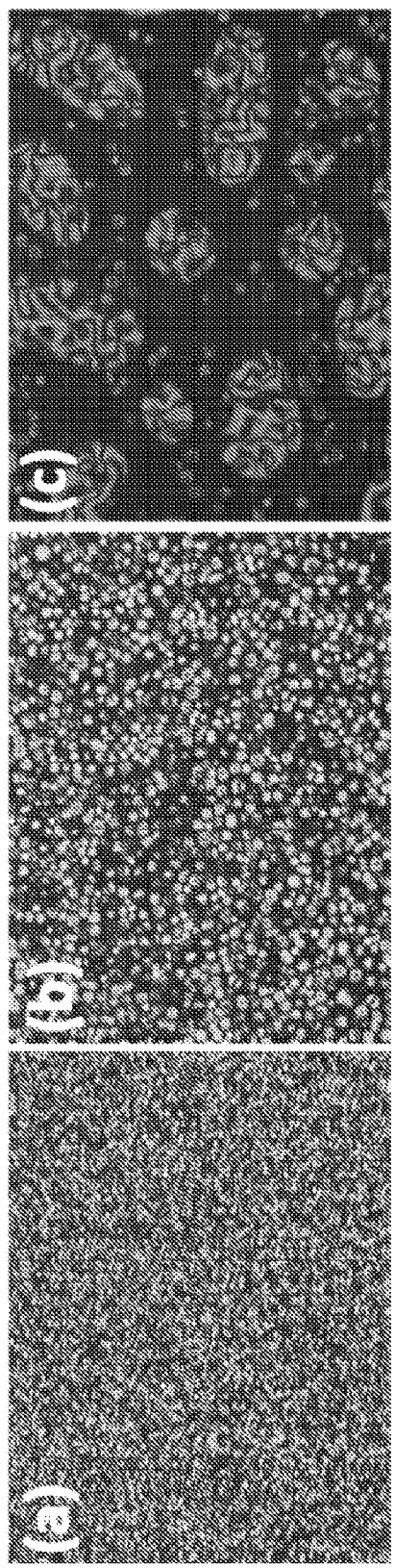
FIGS. 53A, 53B, and 53C are images showing the morphology of PDLC droplets.

As discussed above, the initial morphology of the PDLCs formed by SIP depends on a number of parameters. Among these, thermal annealing after formation of the PDLCs has an effect on the size of the droplets. For the LC:PS composition examined during these studies, the PDLC droplet size appears to increase after incubation. In these experiments, PDLCs were formed using the above protocol, and polarizing optical microscopic images were taken before incubation. After incubation at 60° C. for 4 minutes and equilibration at room temperature, the morphology of the PDLC was imaged. These sensors were then exposed to 8600 ppm toluene for 10 minutes and the morphology was imaged again. The results are shown in FIG. 53. The results show that the morphology of PDLCs can be controlled after formation. Additionally, the results also show that the droplets coalesce after exposure to toluene.

Effect of Toluene Concentration on Response

Figure 54:
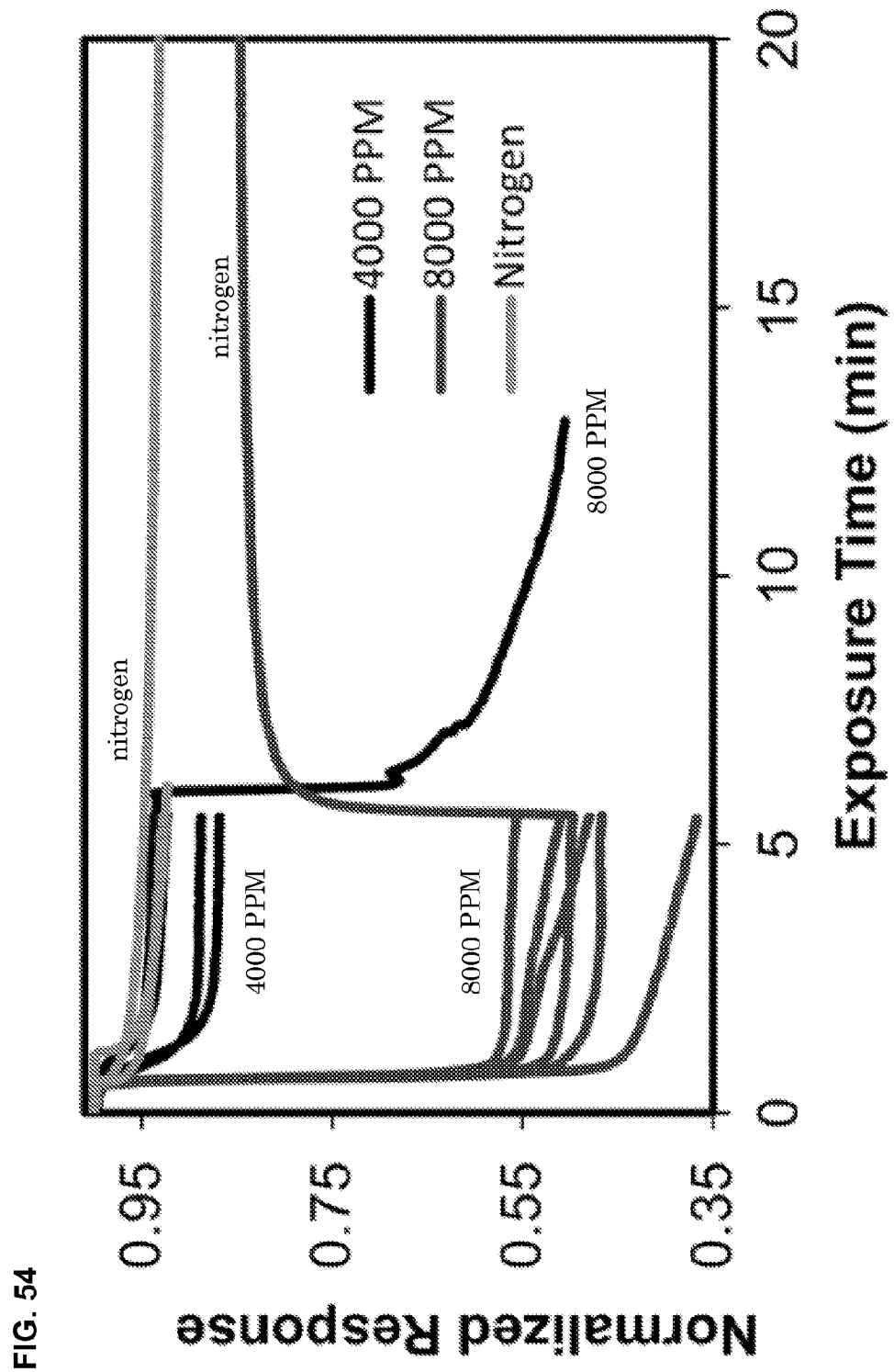
FIG. 54 is a plot showing optical response from PDLC sensors at different concentrations of toluene diluted in dry nitrogen. One sensor was exposed to nitrogen for long time. One sensor used exposed to 4000 PPM toluene was exposed to 8000 PPM toluene after 5 minutes. Similarly, one sensor exposed to 8000 PPM toluene was exposed to dry nitrogen after 5 minutes.

Identical sensors with 15-µl volume and 4-minute incubation at 65° C. were prepared following the protocol described above. These sensors were then exposed to toluene at different concentrations. Different concentrations of toluene were generated by mixing a saturated vapor of toluene (generated by bubbling dry $N_2$ through liquid toluene) at an appropriate ratio with dry $N_2$. Six sensors were first exposed to 4000 ppm toluene for 5 minutes. Before the 5-minute exposure to toluene, each sensor was placed inside the exposure chamber and was allowed to equilibrate for 30 seconds. After the sixth sensor was exposed for 5.5 minutes, the concentration of toluene was increased to 8000 ppm while the response was still measured. After a 1-hour equilibration, six more sensors were exposed to 8000 ppm in a similar fashion. After the 12th sensor (the sixth sensor exposed to 8000 ppm) was exposed to 8000 ppm for 5.5 minutes, the toluene vapor was turned off and the $N_2$ flow rate was increased to 200 sccm. The sensor was exposed to dry $N_2$ during this equilibration time. After a 45-minute equilibration, three sensors were exposed to dry $N_2$. FIG. 54 shows a normalized response as a function of exposure time. The results indicate that the sensors respond to 8000 ppm toluene. Although the sensors exposed to high concentration of toluene reverse back to some extent, there is some permanent change in the sensor. The response from 4000 ppm is very similar to the response from dry $N_2$. The small response to dry $N_2$ suggests that the PDLC droplets respond to air flow.

Figure 55:
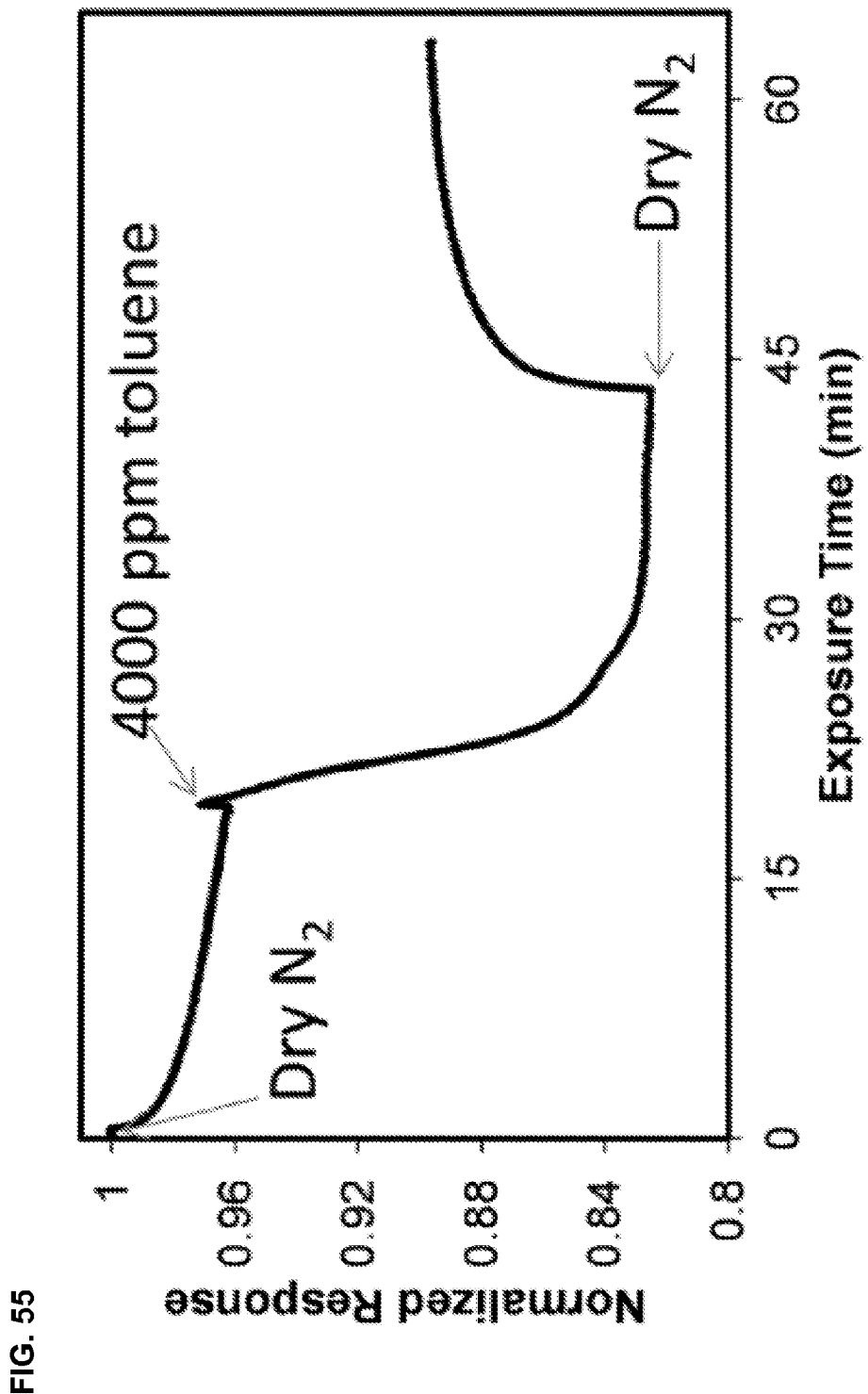
FIG. 55 is a plot showing optical response from PDLC sensor upon sequential exposure to 4000 ppm toluene and dry $N_2$.

To determine whether the small response of the sensor to dry $N_2$ was a result of flow, multiple experiments that included sequential exposure to dry $N_2$ and 4000 ppm toluene were performed under different conditions. One representative exposure result is shown in FIG. 55. In this experiment, the sensor was first equilibrated inside the exposure chamber for 30 seconds and then exposed to dry $N_2$ for ~20 minutes followed by a ~20 minute exposure to 4000 ppm toluene. Finally, the sensor was exposed again to dry $N_2$. The results suggest that the sensor responds to dry $N_2$ alone. However, the response induced by dry $N_2$ is relatively smaller than that from 4000 ppm toluene. This result suggests that this particular embodiment of the sensor has a limit of detection for toluene that is around 4000 ppm.

PDLCs on Rubbed Polymer Films:

The LC directors inside the PDLCs formed on an untreated surface are randomly distributed before exposure to toluene and they remain randomly distributed after they coalesce to form larger droplets. This indicates that the PDLCs undergo a transformation from a higher scattering state to a lower scattering state. If small PDLC droplets are formed on a rubbed surface they scatter light (e.g., appearing bright). Additionally, these droplets coalesce and form larger domains that are aligned by the underlying rubbed surface. To test this hypothesis surfaces were coated with nylon (Evalmide 8061, Dupont Chemicals) and mechanically rubbed. PDLC droplets were formed as described below.

A solution of 0.2% Evalmide 8061 (Dupont Chemicals) was prepared by dissolving an appropriate amount in methanol. The 1"×1" aluminosilicate glass substrate was prescribed to 0.8 cm×0.8 cm and was thoroughly rinsed with acetone and ethanol then dried in a stream of nitrogen. The substrate was subjected to a 2-minute UV ozone treatment. A film of Evalmide was formed by spin coating the Evalmide solution on to this substrate. After evaporation of the solvent, the film was mechanically rubbed 10 times using the weight of the rubbing cloth by placing the substrate between two AlSi glass slides. A mixture of 2:1 LC-polystyrene was prepared by mixing 2% solution of E7 and polymer at an appropriate ratio. 180 microliters of LC-polymer mixture was dispensed on the rubbed substrate. The evaporation rate of the tolune was controlled by covering the substrate with a petri dish with a small (~5 mm) opening. After complete solvent evaporation the sensors were broken into individual pieces and imaged using polarizing optical microscope to determine the size of droplet. In some embodiments, the sizes of the droplets were controlled by incubating these sensor chips at different temperatures as described above.

Results

Morphological Changes Upon Exposure to Toluene

Figure 56:
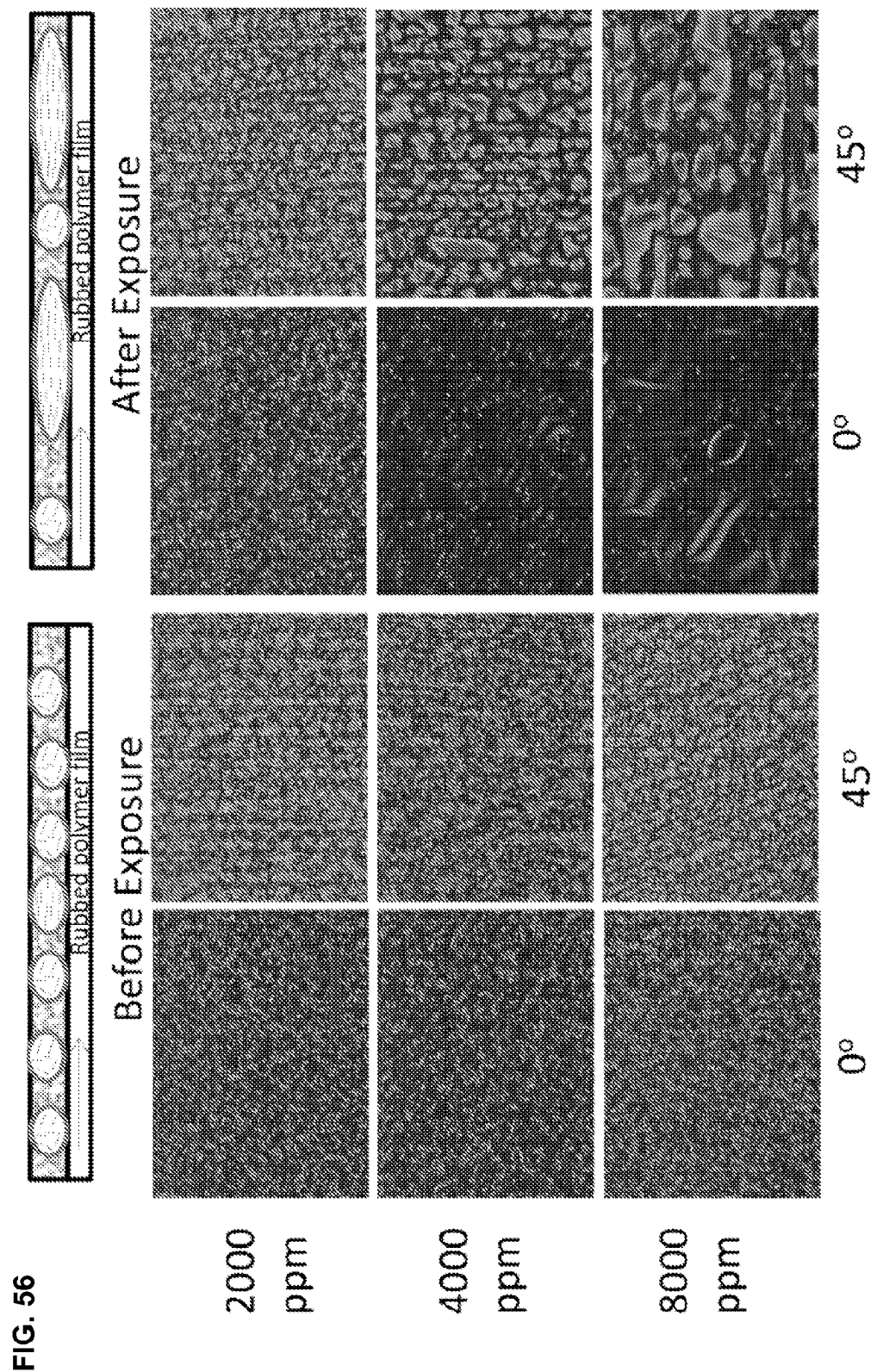
FIG. 56 is a schematic and series of images showing change in the PDLC droplets supported on rubbed polymer film. The images show the appearance of PDLC droplets formed on rubbed surfaces before and after exposure to toluene at different concentrations. All these exposure experiments were performed at 45% relative humidity.

Sensor chips were prepared following the above protocol. The sensors were then exposed to different concentrations of toluene (2000, 5000, and 8000 ppm at 45% RH) for ~10 minutes while the dynamic response was recorded. The morphological appearance of PDLC droplets were imaged before and after exposure at both 0° and 45° orientations using a polarizing optical microscope. FIG. 56 shows the optical images of PDLC droplets before and after exposure. The images show that before exposure to toluene vapor small "domains" of LC are aligned along the rubbing direction. In addition, most droplets are separated and scatter light. As a result, the brightness does not significantly change upon rotation of the sensor chip between crossed polarizers. When the sensors are exposed to toluene vapor, the PDLC microdroplets coalesce to form larger "domains" that are aligned along the rubbing direction of the underlying surface. As a consequence, there is less scattering and the sensor appears much darker if the rubbing direction is parallel to the transmission axis of the polarizers. The images also show that the droplets coalesce more efficiently at a higher concentration than at a lower concentration. As a consequence, the domains are larger at a higher concentration than at a lower concentration. A prolonged exposure to a high concentration leads to formation of isolated droplets on the surface or dewetting of the LC film on the surface (see below).

Figure 57:
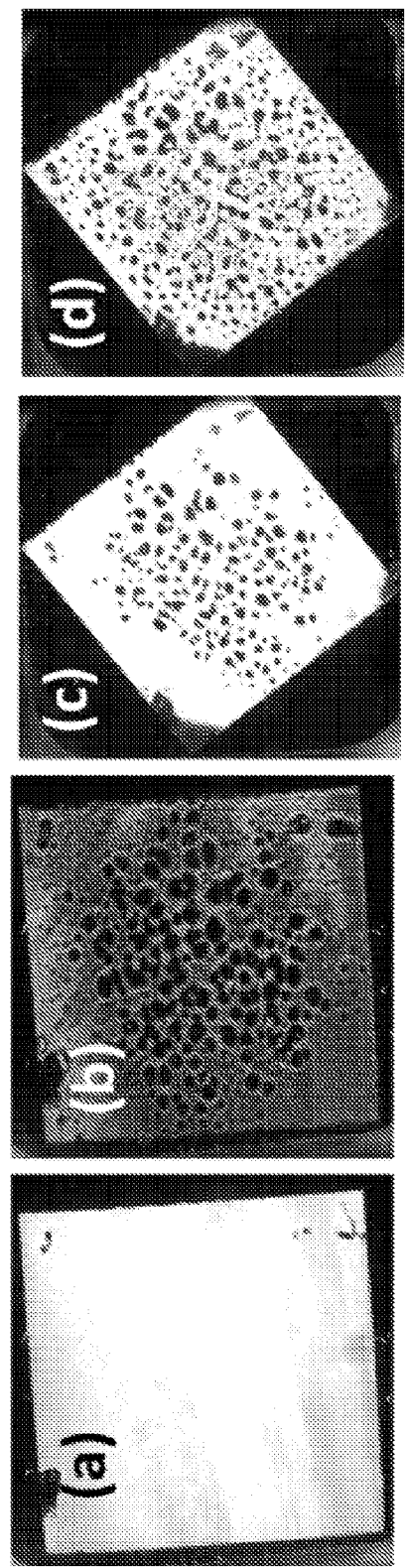
FIG. 57 is a series of images showing the macroscopic appearance of PDLC droplets (a) before exposure, (b) after exposure to 8000 ppm toluene for 8 minutes, (c) same sensor chip rotated by 45°, and (d) rotated chip exposed to 8000 ppm toluene after 8 minutes. All these exposure experiments were performed at 45% relative humidity.

To establish that the sensor response did not result from a lowering of the phase transition temperature due to dissolved PS molecules in the LC host, a sensor chip was first exposed (with the rubbing direction parallel to the transmission axis of the polarizer) to 8000 ppm toluene for 8 minutes until the sensor appeared dark between crossed polarizers. The exposure chamber was then opened and the sensor was rotated by 45° so that the rubbing direction was at a 45° orientation with respect to the polarizers. Since the LC domains were aligned along the rubbing direction the sensor appears bright. In this orientation, the sensor was exposed to 8000 ppm toluene for 8 minutes. Upon exposure, the sensor became darker and more dark spots reappeared. However, the majority of the sensor still remains bright indicating that the LC within these bright domains is still in a nematic phase and the response seen in the first exposure is not due to lowering of the phase transition. The response is indeed due to merging of the microdroplets that subsequently were aligned along the rubbing direction that produced the dark appearance (FIG. 57). In fact, one of the sensors was heated on a hot plate and the morphological changes were observed in real time as the temperature was raised. Although the PDLCs seem to disappear at 54° C., no phase transition was observed until the sensor chip was heated to 65° C. This observation indicated that the change in the optical appearance of the PDLC droplets upon exposure to toluene is not a result of lowering the phase transition temperature.

Optical Response

Figure 58:
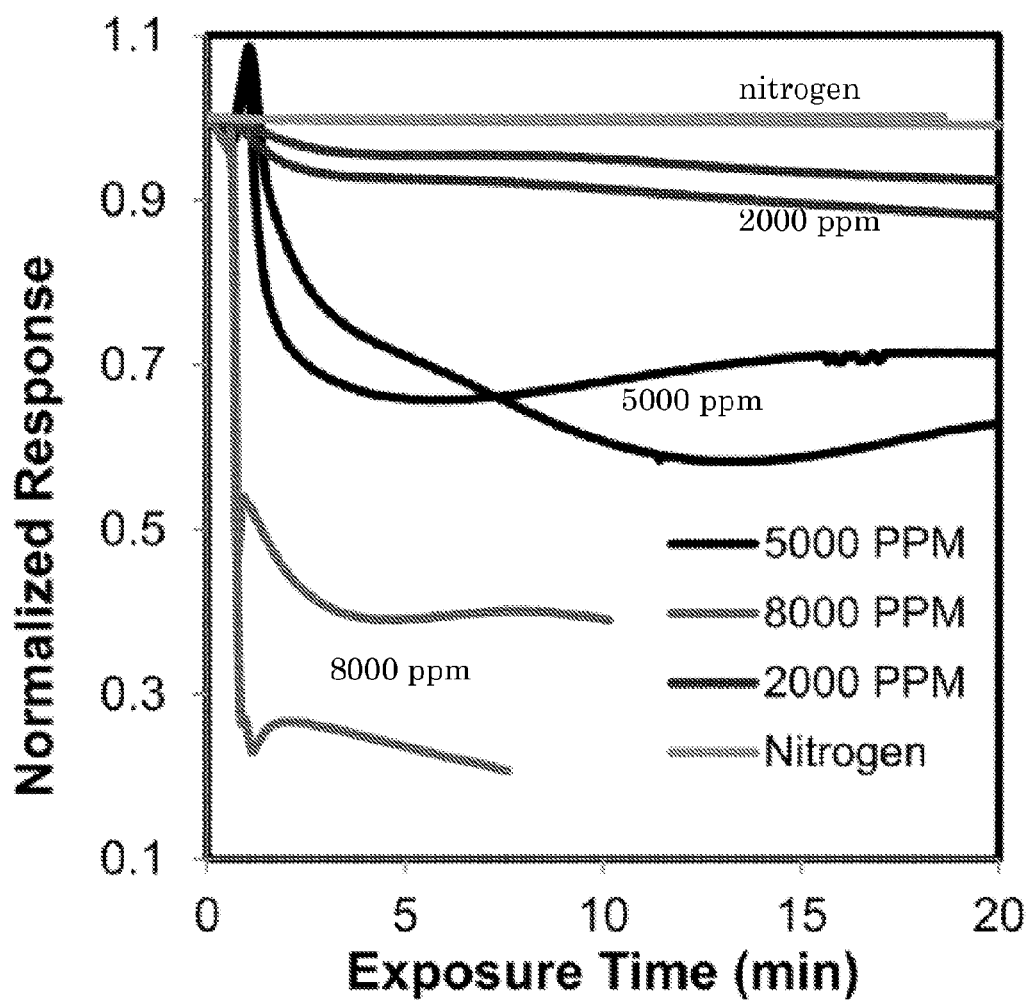
FIG. 58 is a plot showing the optical response from PDLC droplets formed on rubbed surface to toluene at different concentrations.

Multiple sensors were exposed to different concentrations of toluene and nitrogen both at 45% RH. The optical responses for some representative sensors are shown in FIG. 58. The data show that these sensors detect toluene at a concentration as low as 2000 ppm. The response time (the time it takes for the sensor response to "equilibrate") depends on the concentration of toluene. It should be noted that the sensors show a higher contrast ratio (e.g., a large change in the optical response) compared to those prepared without rubbed surface (see FIG. 58). Some inconsistency of the sensor response may have resulted from differences amongst the 9 different sensor ships produced from the same 1"×1" substrate. For example, the evaporation pattern of toluene may have been slightly different among different sensor chips produced from the same substrate.

These results indicate that the E7 PDLCs supported on a rubbed surface are more sensitive than pure E7. The presence of the underlying rubbed surface aligns the LC domains formed after exposure to toluene. This approach of forming PDLCs on a rubbed surface provides for the detection of toluene at concentrations as low as 2000 ppm at 50% RH.

As these initial experiments suggest, humidity has some effect on the sensor response. Finally, it is contemplated that the sensitivity may be improved by using low molecular weight polymers that facilitate morphological changes of the PDLC droplets at lower concentration.

Example 10

Detection of Volatile Organic Compounds Using De-Wetting Induced Orientational Transition of LCs Various approaches have been contemplated to detect volatile organic compounds (VOCs) such as toluene. Some embodiments comprise detecting the dewetting of a thin polymer film upon exposure to an analyte by using liquid crystals (LCs). To test this approach, experiments were performed to demonstrate that a polymer film such as a polystyrene (PS) formed on a glass substrate absorbs toluene and dewets the surface upon exposure to toluene. This dewetting of the PS film is reported in some embodiments using an LC film supported on the PS. Using this approach, detection of toluene at 2000 ppm was demonstrated using a micropillared substrate cleaned with oxygen plasma. It is contemplated that additional experiments and optimization will result in establishing a lower limit of detection and further characterizing this method of detection of VOCs.

Background

The stability of a polymer film on a substrate depends on a number of parameters such as the surface energy of the substrate, the physical and chemical structure of polymer material, the thickness of the film, etc. Some polymer materials such as polystyrene form a stable film on solid surfaces such as such as glass or silicon. PS films dewet if the thickness of the film is below a critical value or the temperature is elevated above a critical temperature. Exposure to VOCs (e.g., toluene) and heat affect a polymer film similarly—e.g., exposure to toluene lowers the glass transition temperature of the polymer or it can induce an orientational change of LC supported on rubbed polymer films. As such, it was anticipated that exposure to toluene would induce the detwetting of the film. Then, if the orientation of LC on the polymer film and on the substrate is different, then exposure to VOCs would lead to a change in the orientation of the LC and therefore provide a means to detect the presence of VOCs. This approach is particularly useful when the polymer material to be used not only provides a LC orientation different than the underlying substrate, but also absorbs VOCs. These experiments are based on the earlier findings that showed low molecular weight PS (MW ~10000) films coated on glass substrates align LC such as E7 perpendicularly to the surface and that the polymer dispersed liquid crystal droplets formed with PS start dewetting the surface when exposed to a high concentration (~8000 ppm) of toluene for prolonged time. The basic principle behind the dewetting-induced orientational transition is shown in FIG. 35. The main difference between an analyte-induced orientational transition and this approach is that in the analyte-induced orientational transition approach the LC remains in contact with the chemically functionalized surface that gets modified upon exposure to target analytes. In this approach, the chemically functionalized surface (in this case polymer) is modified and physically dewets the substrate and, as a result, the LC comes in contact with the underlying surface.

Alignment of LC on PS Coated Surfaces and Effect of Thermal Annealing

A PS solution (~2% by weight) was prepared by dissolving PS (MW ~10,000, Sigma 81406-1 G) in of toluene at appropriate ratio. The solution was then repeatedly heated at 70° C. and vortexed until all the PS was completely dissolved to give a clear solution. This solution was used as a stock solution to coat different substrates forming PS films.

Surfaces coated with polymers such as polyimide (PI) and PS are widely studied for LC alignment. While PI-coated surfaces are widely used in display industries to give planar and homeotropic alignment, PS coated surfaces are studied because of their uniqueness in LC alignment properties. Untreated surfaces coated with high molecular weight PS are well known for their ability to promote random planar alignment. However, these surfaces, when mechanically rubbed, provide LC alignment that is perpendicular to the rubbing direction. PS coated surfaces, although not stable for display applications, are widely studied because of this unusual alignment behavior. Rubbed polyimide surfaces, in contrast to rubbed PS surfaces, provide a uniform alignment along the rubbing direction. While most studies on rubbed PS surfaces have been performed with high molecular weight PS, systematic studies of LC alignment on surfaces treated with PS with different (e.g., lower) molecular weights have recently started to emerge (see, e.g., Seung Woo Lee, et al. (2003), "Effect of Molecular Weight on the Surface Morphology, Molecular Reorientation, and Liquid Crystal Alignment Properties of Rubbed Polystyrene Films", *Macromolecules* 36: 9905-9916).

Figure 60:
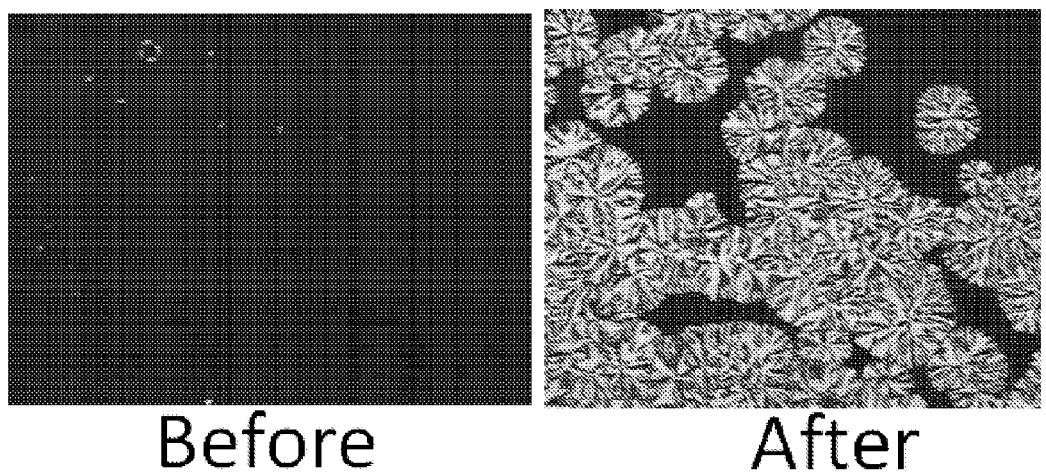
FIG. 60 comprises images showing the microscopic (4×) change in appearance of a LC cell upon thermal treatment. The formation of the microscopic domains resemble a typical pattern observed in dewetting of polymer films.

Experiments performed during the development of embodiments of the present technology suggested that surfaces coated with low molecular weight (MW ~10,000) PS promotes alignment perpendicular to the surface, that is, homeotropic alignment. To confirm this observation, several 1"×1" glass substrates (Fisher Scientific) were cleaned by rinsing with acetone and ethanol. The substrates were then dried in a stream of nitrogen. Dry surfaces were UV-ozone cleaned for 2 minutes. Some substrates were set aside to prepare LC cells with untreated glass, while other substrates were coated with a film of PS by spin coating the stock PS solution at 2000 rpm. After spin coating, the solvent was allowed to evaporate and the substrates were broken into 0.5"×1" pieces. These substrates were used to assemble LC cells with different substrate combinations:

1. PS-OTS: PS coated substrate paired with OTS treated substrate; cell gap ~30 micron
 2. PS-PS: PS coated substrate paired with PS coated substrate; cell gap ~25 micron defined by mylar
 3. Glass-OTS: Clean glass substrate paired with OTS treated substrate; cell gap ~30 micron
 4. Glass-Glass: Clean glass substrate paired with clean glass substrate; cell gap ~25 micron defined by mylar A 10-microliter droplet of E7 was placed at the center of one of the substrates and the top substrate was overlaid to form a LC cell by holding the two substrates together (e.g., with binder clips). These cells were then imaged between crossed polarizers using a digital camera and then using the polarizing optical microscope (POM) to determine the alignment of the LC. Conoscopic images of the cells were also recorded to confirm the homeotropic alignment of the LC. After imaging, these cells were incubated (e.g., inside an oven) at 60° C. for 10 minutes. The cells were them imaged for LC alignment. FIG. 60 shows the camera and POM images of the LC cells fabricated with different surface treatment conditions.

The optical images show that the clean glass substrates, whether paired with another clean glass substrate or with an OTS-treated surface, provide a planar alignment (bright image) on the surface and the alignment remains unchanged upon thermal annealing. A surface treated with PS (MW ~10,000) provides homeotropic alignment (dark images) independent of whether it is paired with an OTS treated surface or a PS coated surface. The "Maltese Cross" shape observed in the conoscopic image confirms homeotropic alignment. Unlike other high molecular weight PS films, this PS provides homeotropic alignment. When these LC cells were incubated at 60° C. for 10 minutes, the cells prepared with PS film appeared bright between crossed polarizers. However, the LC cells prepared with the clean glass substrates remain unchanged (stayed bright). This indicates that the LC alignment behavior on the PS treated surface changes after thermal annealing.

Figure 59:
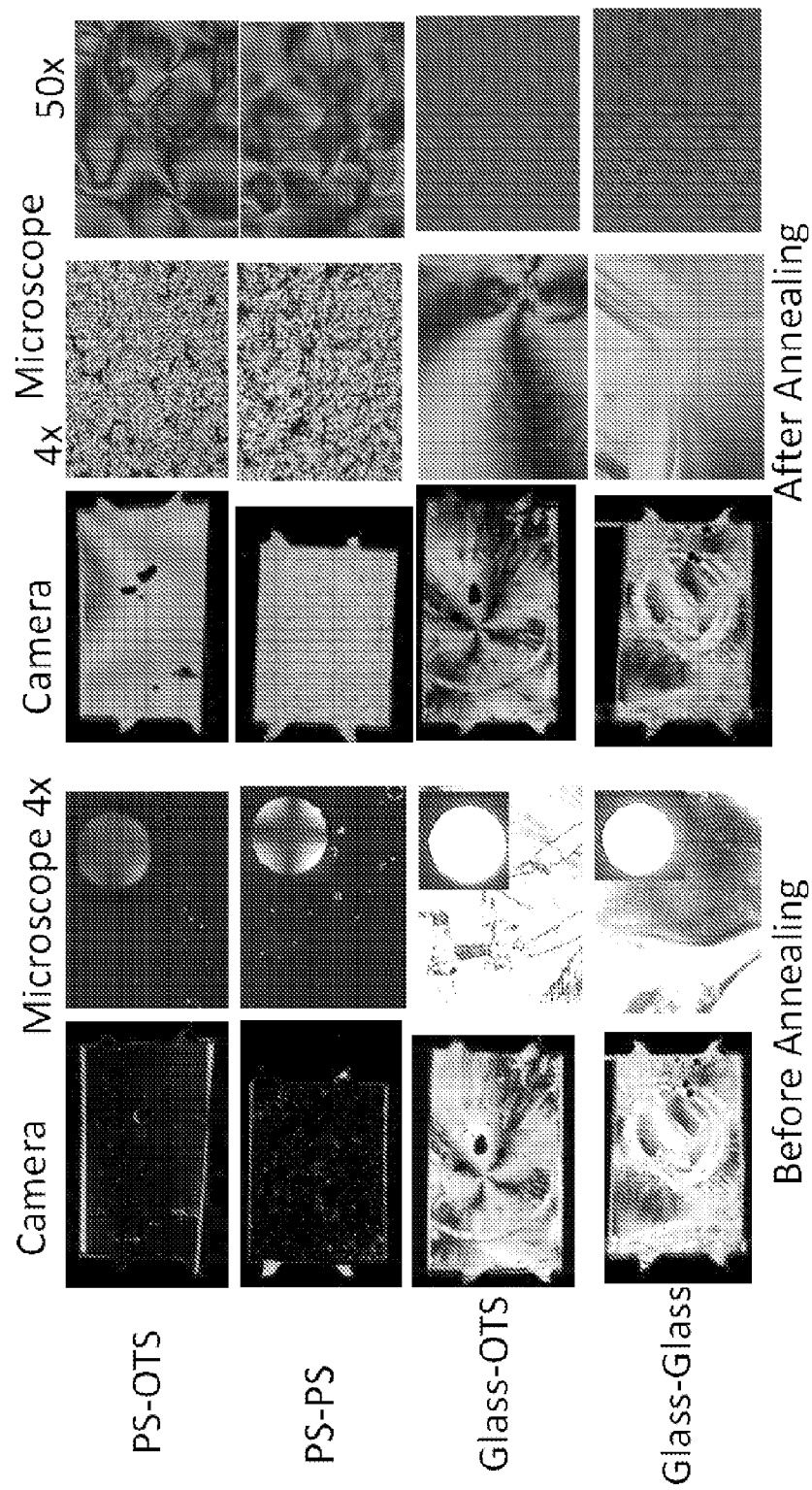
FIG. 59 is a series of images showing the alignment of LC on untreated glass surfaces and surfaces coated with PS paired with different top surfaces. The images were taken with polarizing optical microscopic with 4× and 50× magnifications (as shown) and a camera before and after annealing the LC cells for 10 minutes inside an oven at 70° C. The insets on the second column show conoscopic images.

A closer look at the microscopic images reveals that small islands of LC domains form on the LC cell after thermal annealing (FIG. 59). The size and number of these domains depend on the extent of thermal annealing. The planarly aligned patterns randomly originate from nucleation sites, very similar to the patterns observed in typical dewetting of a polymer film on a solid surface. Formation of these domains during thermal annealing indicates that the LC reorientation observed in these experiments is a consequence of PS film dewetting on the surface and is not from molecular reorganization within the film itself. When these PS coated films were mechanically rubbed, the cells appear bright. The brightness of the LC cell depends on the rubbing strength and relative orientation of the cell with respect to transmission axes of the crossed polarizers, indicating that the rubbed PS film can provide uniform planar alignment if the surface is rubbed. However, after annealing, the cells remain bright and the microscopic images show random planar alignment (FIG. 60).

Exposure to Toluene

Figure 61:
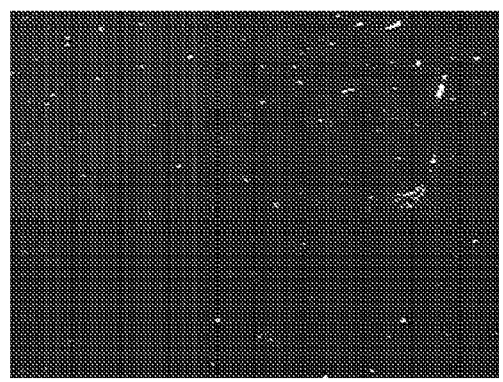
FIG. 61 provides images showing the appearance of a sensor upon exposure to saturated vapor of toluene.
Figure 61:
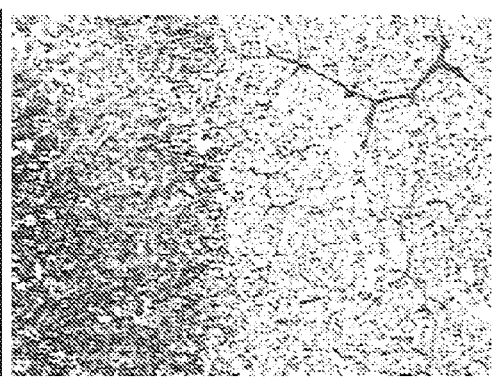

To test whether these observations of thermal annealing apply to sensing toluene vapor, a 1"×1" glass substrate was pre-scribed into 9 0.8 cm×0.8 cm pieces. The scribed side of the substrate was then cleaned and coated with a 2% PS solution as described above. After solvent evaporation, the substrate was broken into 9 individual 0.8 cm×0.8 cm pieces. Each piece was then coated with 20 microliters of LC E7 to fabricate a sensor chip. The sensor chip was then imaged using the POM. After imaging, the sensor was exposed to saturated toluene vapor by holding it for ~30 seconds in the head space above a 1-ml volume of toluene at the bottom of an 8-ml vial. The sensor was imaged again using the POM. As shown in FIG. 61, the sensor appeared bright upon exposure to saturated vapor of toluene. This result shows that the PS coated surface can be used to detect toluene based on dewetting-induced orientational transition of LC.

Figure 62:
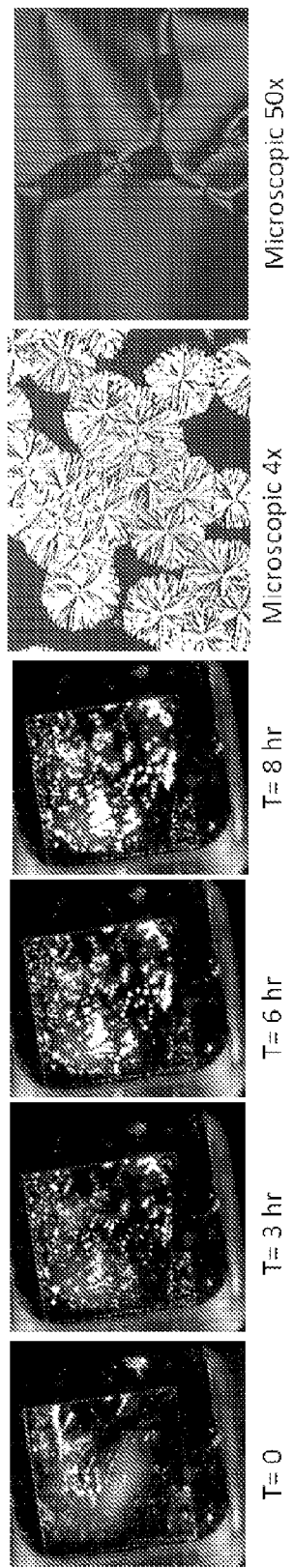
FIG. 62 is a series of images showing the macroscopic appearance of sensor upon exposure to 5000 ppm toluene (at 50% RH) for different durations. The last two images show the microscopic appearance after overnight exposure to 5000 ppm toluene (50% RH) at 4× and 50× magnification, respectively.

To test detection toluene concentrations lower than a saturated concentration of toluene, an identical chip was exposed to 5000 ppm toluene at 50% RH using the exposure system. A toluene concentration of 5000 ppm was generated by mixing a saturated concentration of toluene with wet nitrogen to provide the appropriate ratio. The sensor was exposed inside a small exposure chamber at a flow rate of 200 ml/min while the optical appearance of the sensor chip was recorded in real time. FIG. 62 shows the macroscopic and POM images of the sensor chip after exposure to 5000 ppm toluene. These results indicate that there is a noticeable change in the LC alignment upon exposure to 5000 ppm toluene. The microscopic images also show that the texture of the defects induced by exposure to toluene is very similar to that induced by thermal annealing. This suggests that the mechanism responsible for the change in the optical appearance due to thermal annealing is very similar to that due to exposure to toluene.

Sensors on Micropillared Substrates

Micro-pillared sensor substrates with 4 sensors (plasma cleaned using 100 W energy for 30 seconds) were rinsed briefly with acetone and ethanol. The chips were then dried in a stream of nitrogen. These chips were cleaned using UV-ozone for 2 minutes. The chips were coated with 2% PS using the same protocol described above. After solvent evaporation, the sensors were filled with a small amount of LC E7 using a tip of a paper clip until the sensor was filled with LC.

Figure 63:
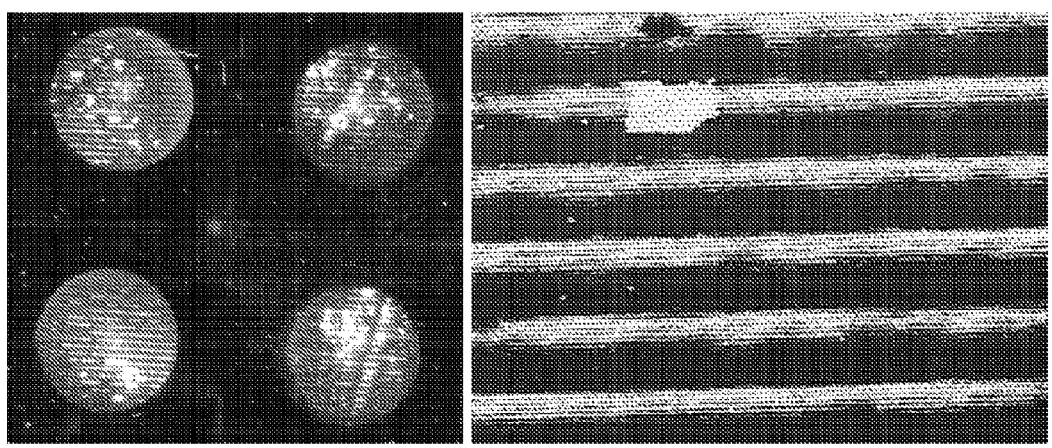
FIG. 63 shows the macroscopic (camera) and microscopic appearance of sensor fabricated on micropillared substrate. The polarizing optical microscopic (POM) image on the left shows the bright lines due to planar alignment of LC.
Figure 64:
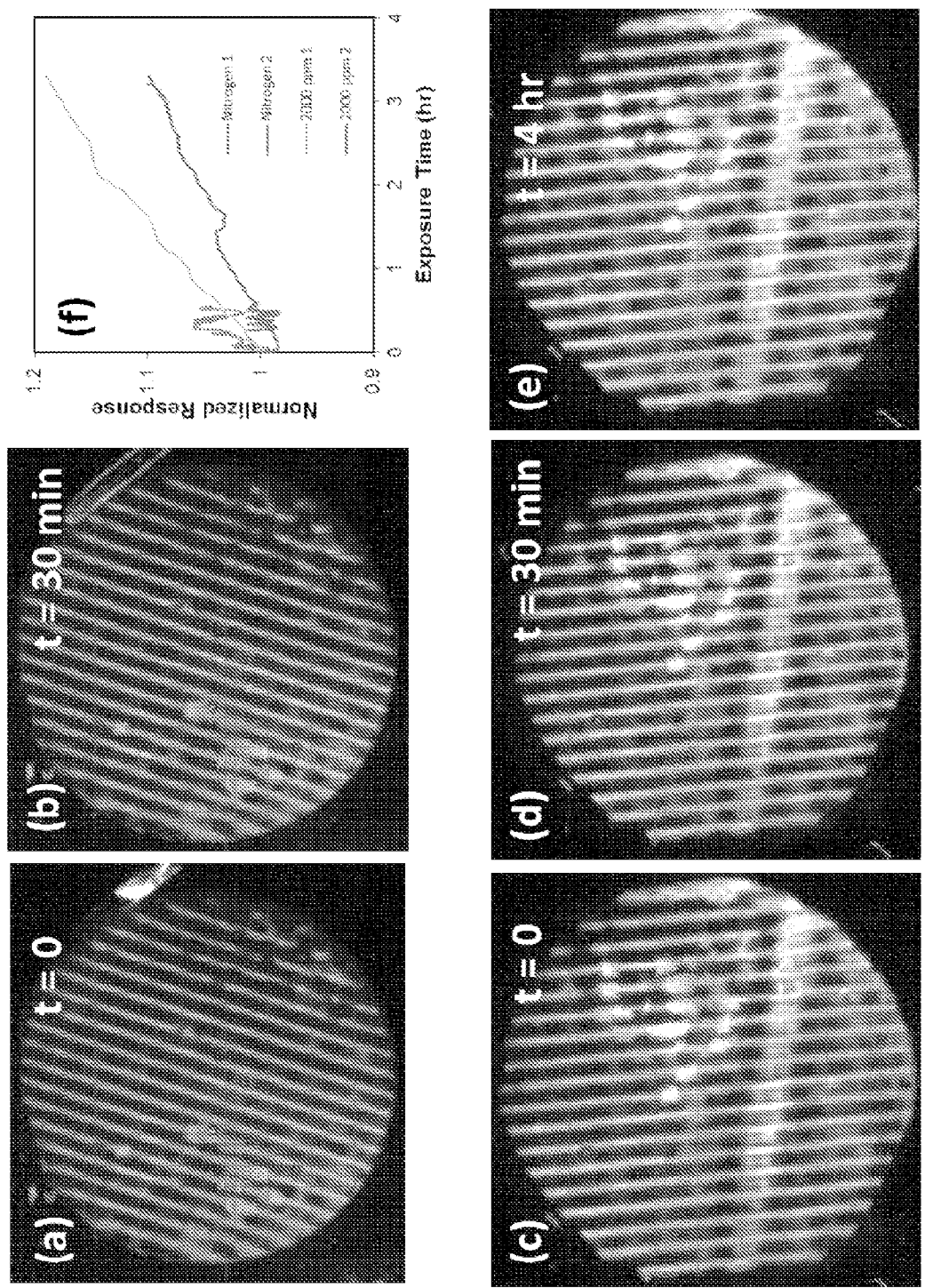
FIG. 64 shows the appearance of micro-pillared sensor before and after exposure to nitrogen (a: before exposure) and (b: after 30 minutes exposure) and 2000 ppm toluene (c: before exposure), (d: 30 minutes exposure) and (e: after 4 hour exposure). Plot (f) shows a quantitative measurement of the response.

The alignment of LC on these sensor chips was weakly homeotropic in the sense that there were few white lines with planar alignment in an otherwise homeotropic dark background (FIG. 63). After storing the sensors overnight, they were exposed to nitrogen (at 50% RH for 30 minutes) and 2000 ppm toluene (at 50% RH for 4 hours) at 200 ml/min inside a small exposure chamber. During the 30 minute exposure, no significant change was observed in the appearance of the sensor exposed to nitrogen. However, the sensor exposed to 2000 ppm exhibited a detectable change in the appearance at 30 minutes. To confirm that the change resulted from exposure to toluene at 2000 ppm, the sensors were exposed for a total of 4 hours. At the end of 4-hour exposure, the sensor clearly appeared different. These images were also analyzed to quantitate the sensor response. The plot in FIG. 64(*f*) shows that the sensors respond to 2000 ppm toluene.

Summary

Experiments performed with a thin film of LC supported on surfaces coated with low molecular weight PS confirmed that the LC E7 adopts a homeotropic alignment on these surfaces. This orientation of LC is independent of the nature of the second interface (PS, OTS, or air) used. Results show that when a LC film supported on a PS coated surface is exposed to saturated toluene vapor, it undergoes an orientational transition and the film appears bright between crossed polarizers. This behavior is similar to that observed upon a thermal annealing of polystyrene film. At a lower concentration, the film shows a partial orientational transition that appears as a randomly aligned domain originating from nucleation sites in a homeotropic background. These results suggest that the orientational transition is associated with the dewetting of the PS film on the glass substrate. Using plasma cleaned micropillared substrates, 2000 ppm of toluene was detected. To exploit this mechanism of detection of toluene and other VOCs, it is contemplated that parameters such as the surface properties and the thickness of the PS film, etc. will have a role in improving the sensor sensitivity and response.

Example 11

Comparison of Microfluidic Cells Fabricated with Different Metal Salts

During the development of embodiments of the technology provided herein, experiments were conducted to test the detection of analyte (e.g., $H_2S$) by an LC sensor comprising various metal salts. In particular, data were collected in experiments using metal salts other than lead perchlorate.

"Open-faced" LC sensors were prepared as described for the microfluidic cells of Example 1 except the cells did not comprise the top cover. Sensors were exposed to $H_2S$ using the exposure system as described above and the response times were recorded as a function of exposure to various concentration of $H_2S$ (Table 5). For these experiments, the response time was defined as the change in LC alignment that was visually observed by a change from dark to bright when viewed through crossed polarizers.

TABLE 5

Detection of $H_2S$ by LC sensors comprising metal salts

| Metal Salt | $H_2S$ Concentration (ppm) | Response Time (min) |
|---|---|---|
| Lead Perchlorate | 1 | 3 |
| Lead Perchlorate | 0.1 | 25 |
| Zinc Perchlorate | 1 | 1 |
| Zinc Perchlorate | 0.1 | 10 |
| Manganese Perchlorate | 1 | 1.5 |
| Chromium Perchlorate | 1 | 7 |
| Indium Perchlorate | 1 | 5 |
| Gallium Perchlorate | 1 | 5 |

These data indicate that the choice of metal salt provides for tuning the performance (e.g., sensitivity, response time, etc.) of the dosimeter. Further, one of skill in the art would realize that responses could be further tuned by mixing metal salts, or, more generally, by adjusting the surface functionalities.

Example 12

Direct Detection of $NO_2$

During the development of embodiments of the technology, "open-faced" LC sensors were fabricated using a micropillar surface as described above that was coated with titanium and gold. The gold surface was functionalized with 4-Aminothiophenol (ATP), whose amine group reacts irreversibly with $NO_2$. The LC thin film layered over the ATP for this sensor was 6CB. When the open-faced sensors were exposed to 2 ppm $NO_2$, a response (defined in this experiment as a change from dark to bright as observed visually through crossed polarizers) was observed within approximately ten minutes.

In some embodiments of NO$_2$ sensors (e.g., as described above), NO$_2$ at 20 ppb is detected by first exposing the sensor to the target gas then adding liquid crystal to read the sensor. In contrast, the embodiment of the device tested in these experiments is a sensor that is fabricated with the liquid crystal in place so that the LC realignment occurring upon exposure to NO$_2$ is directly observed without further additions. These data further indicate that the sensor designs can be modified to provide performance characteristics suitable for widely varying applications.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in the art or related fields are intended to be within the scope of the following claims.

We claim:

1. A method for detecting an analyte in a gaseous phase, the method comprising:
   1) providing a liquid crystal assay device comprising:
      a) a first surface contacting a composition comprising a liquid crystal so that the liquid crystal forms a liquid crystal film on the first surface;
      b) a second surface;
      c) a headspace between the liquid crystal film on the first surface and the second surface;
   2) exposing the liquid crystal assay device to a sample suspected of comprising an analyte; and
   3) detecting the presence of the analyte,
      wherein a change in a property of the liquid crystal composition in the liquid crystal assay device caused by an interaction of the analyte with the liquid crystal assay device is indicative of the presence of the analyte.

2. The method of claim 1 wherein the first surface comprises a functional group and an interaction of the analyte with the functional group causes the change in the property of the liquid crystal composition.

3. The method of claim 2 wherein the functional group is specific for the analyte.

4. The method of claim 2 wherein the functional group is 4-aminothiophenol.

5. The method of claim 1 wherein the headspace is 5 to 50 microns.

6. The method of claim 1, wherein said headspace is variable.

7. The method of claim 1, wherein said first and second surfaces form a compartment having first and second open ends, wherein the headspace at said first end is from 1 to 20 microns above the liquid crystal film and the headspace at the second end is from 21 to 100 microns above the liquid crystal film.

8. The method of claim 1 wherein the first surface further comprises micro-pillars.

9. The method of claim 1 wherein the second surface is functionalized with (Tridecafluoro-1,1,2,2-tetrahydrooctyl)-trichlorosilane.

10. The method of claim 1 wherein the first surface is functionalized with a lead salt, a zinc salt, a manganese salt, a chromium salt, an indium salt, a gallium salt, or a mixture thereof.

11. The method of claim 1 wherein the analyte is H$_2$S, HCHO, or NO$_2$.

12. The method of claim 1 wherein the detecting comprises measuring a change in a property of the liquid crystal composition selected from the group consisting of optical appearance, optical absorbance, optical anisotropy, magnetic anisotropy, dielectric anisotropy, and phase transition temperature.

13. The method of claim 1 wherein exposing the liquid crystal assay device to a sample suspected of comprising an analyte causes a phase transition in the liquid crystal composition from a first phase selected from the group consisting of an isotropic phase, a nematic phase, or a smectic phase to a second phase selected from the group consisting of an isotropic phase, a nematic phase, and a smectic phase.

14. The method of claim 1 wherein the liquid crystal composition undergoes an orientational transition in the presence of the analyte.

15. The method of claim 1 further comprising quantifying an analyte concentration by measuring brightness of a reacted area of the liquid crystal device.

16. The method of claim 1 further comprising quantifying an analyte concentration by measuring a size of a reacted area of the liquid crystal device.

17. The method of claim 1 further comprising quantifying an analyte concentration by measuring a distance of a birefringent front from a site of exposure of the liquid crystal assay device to the sample suspected of comprising the analyte.

18. The method of claim 1 wherein the detecting comprises measuring a reflection or a transmission of polarized light from the liquid crystal assay device.

19. The method of claim 1 further comprising exposing the liquid crystal assay device to a sub-responsive amount of the analyte before exposing the liquid crystal assay device to a sample suspected of comprising the analyte.

* * * * *